US009764006B2

(12) United States Patent
Wang et al.

(10) Patent No.: US 9,764,006 B2
(45) Date of Patent: Sep. 19, 2017

(54) BIVALENT IL-2 FUSION TOXINS

(71) Applicant: The General Hospital Corporation, Boston, MA (US)

(72) Inventors: Zhirui Wang, Maiden, MA (US); Christene A. Huang, Dover, DE (US); David H. Sachs, Auburndale, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/650,699

(22) PCT Filed: Dec. 9, 2013

(86) PCT No.: PCT/US2013/073916
§ 371 (c)(1),
(2) Date: Jun. 9, 2015

(87) PCT Pub. No.: WO2014/093240
PCT Pub. Date: Jun. 19, 2014

(65) Prior Publication Data

US 2016/0030526 A1 Feb. 4, 2016

Related U.S. Application Data

(60) Provisional application No. 61/735,497, filed on Dec. 10, 2012.

(51) Int. Cl.
| | |
|---|---|
| *C07K 14/55* | (2006.01) |
| *C12N 15/09* | (2006.01) |
| *C12N 15/63* | (2006.01) |
| *A61K 38/20* | (2006.01) |
| *A61K 38/45* | (2006.01) |
| *A61K 45/06* | (2006.01) |
| *C12N 15/81* | (2006.01) |
| *C12N 9/10* | (2006.01) |
| *C07K 14/21* | (2006.01) |
| *A61K 38/00* | (2006.01) |

(52) U.S. Cl.
CPC .......... *A61K 38/45* (2013.01); *A61K 38/2013* (2013.01); *A61K 45/06* (2013.01); *C07K 14/55* (2013.01); *C12N 9/1077* (2013.01); *C12N 15/63* (2013.01); *C12N 15/815* (2013.01); *A61K 38/00* (2013.01); *C07K 14/21* (2013.01); *C07K 2319/55* (2013.01); *C12N 15/09* (2013.01); *C12Y 204/02036* (2013.01)

(58) Field of Classification Search
None
See application file for complete search history.

(56) References Cited

U.S. PATENT DOCUMENTS

| | | | |
|---|---|---|---|
| 4,545,985 A | 10/1985 | Pastan et al. | |
| 4,892,827 A | 1/1990 | Pastan et al. | |
| 5,458,878 A | 10/1995 | Pastan et al. | |
| 5,843,711 A | 12/1998 | Collier et al. | |
| 6,803,225 B2 | 10/2004 | Contreras et al. | |
| 7,029,872 B2 | 4/2006 | Gerngross | |
| 7,252,933 B2 | 8/2007 | Contreras et al. | |
| 7,314,632 B1 | 1/2008 | Fitzgerald | |
| 7,326,681 B2 | 2/2008 | Gerngross | |
| 7,449,308 B2 | 11/2008 | Gerngross et al. | |
| 7,507,573 B2 | 3/2009 | Contreras et al. | |
| 7,585,942 B2 | 9/2009 | Harrison et al. | |
| 7,696,338 B2 | 4/2010 | Neville, Jr. et al. | |
| 2008/0166375 A1 | 7/2008 | Leppla et al. | |
| 2009/0010966 A1 | 1/2009 | Davis et al. | |
| 2009/0041797 A1 | 2/2009 | Davis et al. | |
| 2009/0221500 A1* | 9/2009 | Davis et al. | C07K 14/34 514/1.1 |

OTHER PUBLICATIONS

Pastan et al, Nature 2006, vol. 6, p. 559-565.*
Anderson W, Nature, 1998. vol. 392, pp. 25-30.*
Verma et al. Nature, 1997. Volume 389, p. 239-242, col. 3, paragraph 2.*
Crystal R, Science, 1995. vol. 270, pp. 404-410.*
Gabor M. Rubanyi , Mol Aspects Med , 2001 vol. 22, pp. 113-142.*
Marshall (1995) Science, vol. 269, p. 1054, col. 3, paragraph 2, and page.*
Eck et al. (Goodman & Gilman's the Pharmacological Basis of Therapeutics (1996), 9th Edition, Chapter 5, McGraw-Hill, NY, pp. 77-101).*
Marshall, Science, 1995, vol. 269, pp. 1050-1055.*
Juengst et al, British Medical Journal; 2003, vol. 326, pp. 1410-1411.*
Peraino et al, The Journal of Immunological Methods, Sep. 18, 2013, vol. 389-399, pp. 33-43.*
Wei et al, Protein Engineering, Design & Selection, 204, Vol: 27; No. 9, pp. 289-295.*
Peraino et al, The Journal of Immunological Methods, Aug. 4, 2014; 405: 57-66.*
Knutson et al, The Journal of Immunology, 2006; vol. 177, pp. 84-91.*
Tai-You Ha; Immune Network, 2009, vol. 9, No. 6, pp. 209-235.*
Chaudhary, Vaccine, 2016; vol. 4, No. 28, pp. 1-25.*
Johnson et al, Journal of immunotherapy, 2007, vol. 30, No. 2, pp. 203-214.*
Abi-Habib et al., "A urokinase-activated recombinant diphtheria toxin targeting the granulocyte-macrophage colony-stimulating factor receptor is selectively cytotoxic to human myeloid leukemia blasts," Blood., Oct. 1, 2004, 104(7):2143-2148.
Attia et al., "Inability of a Fusion Protein of IL-2 and Diphtheria Toxin (Denileukin Diftitox, DAB389IL-2, Ontak) to Eliminate Regulatory T Lymphocytes in Patients With Melanoma," J Immunother., 2005, 28(6):582-592.
Aullo et al., "A recombinant diphtheria toxin related human CD4 fusion protein specifically kills HIV infected cells which express gp120 but selects fusion toxin resistant cells which carry HIV, " EMBO Journal, 1992, 11(2):575-83.

(Continued)

*Primary Examiner* — Bridget E Bunner
*Assistant Examiner* — Fozia Hamud
(74) *Attorney, Agent, or Firm* — Fish & Richardson P.C.

(57) ABSTRACT

IL-2 fusion toxins, e.g., bivalent-IL2 fusion toxins, and methods of use thereof.

20 Claims, 27 Drawing Sheets

(56) References Cited

OTHER PUBLICATIONS

Barnett et al., "Regulatory T Cells in Ovarian Cancer: Biology and Therapeutic Potential," Am. J Reprod. Immunol, Dec. 2005, 54(6):369-377.

Bollok et al., "Recent Patents on the Pichia Pastoris Expression System: Expanding the Toolbox for Recombinant Protein Production," Recent Patents on Biotechnology, 2009, 3:192-201.

Chaudhary et al., "Pseudomonas exotoxin contains a specific sequence at the carboxyl terminus that is required for cytotoxicity," Proc. Natl. Acad. Sci., Jan. 1990, 87:308-312.

Cho et al., "Establishment of transplantable porcine tumor cell lines derived from MHC-inbred miniature swine," Blood, Dec. 2007; 110: 3996-4004.

Collins, "Species specificity of interleukin 2 binding to individual receptor components," Aug. 1989, 19(8): 1517-1520.

Debinski et al., "Substitution of Foreign Protein Sequences into a Chimeric Toxin Composed of Transforming Growth Factor a and Pseudomonas Exotoxin," Mol Cell Biol., Mar. 1991, 11(3):1751-1753.

Foss, "Interleukin-2 Fusion Toxin: Targeted Therapy for Cutaneous T Cell Lymphoma," Ann. NY Acad Sci., 2001, 941:166-76.

Gritzapis et al., "Ontak reduces the immunosuppressive tumor environment and enhances successful therapeutic vaccination in HER-2/neu-tolerant mice," Cancer Immunol Immunother., 2012, 61:397407.

Heimbrook et al., "Transforming growth factor a-Pseudomonas exotoxin fusion protein prolongs survival of nude mice bearing tumor xenografts," Proc NatlAcad Sci , Jun. 1990, 87(12):4697-4701.

Hermanrud et al., "Expression and purification of soluble murine CD40L monomers and polymers in yeast Pichia pastoris," Protein Expr. Purif , Mar. 2011, 76(1): 115-20.

International Preliminary Report on Patentability in International Application No. PCT/US2013/073916, dated Jun. 25, 2015, 6 pages.

Kelley et al., "Interleukin 2-diphtheria toxin fusion protein can abolish cell-mediated immunity in vivo," Proc. Natl. Acad. Sci., Jun. 1988, 85:3980-3984,.

Kim et al., "A fold-back single-chain diabody format enhances the bioactivity of an anti-monkey CD3 recombinant diphtheria toxin-based immunotoxin," Protein Eng. Des. Sel., Aug. 10, 2007, 20(9):425-432.

Kreitman et al., "Immunotoxins for Targeted Cancer Therapy," AAPS Journal. 2006; 8(3):E532- E551.

Litzinger, et al., "IL-2 immunotoxin denileukin diftitox reduces regulatory T cells and enhances vaccine-mediated T-cell immunity," Blood, Nov. 1, 2007, 110(9):3192-3201.

Liu et al., "Targeted introduction of a diphtheria toxin resistant mutation into the chromosomal EF-2 locus of Pichia pastoris and expression of immunotoxin in the EF-2 mutants," Protein Expr Purif., Aug. 2003, 30(2):262-274.

Liu et al., "Expression of an Anti-CD3 Single-Chain Immunotoxin with a Truncated Diptheria Toxin in a Mutant Cho Cell Line," Protein Expr. Purif., 2000, 19:304-311.

Mahnke et al., "Depletion of CD4+CD25+ human regulatory T Cells in vivo: Kinetics of Treg depletion and alterations in immune functions in vivo and in vitro," Int. J. Cancer, 2007, 120:272333.

Morse et al., "Depletion of human regulatory T cells specifically enhances antigen-specific immune responses to cancer vaccines," Blood, Aug. 2008, 112(3):610-618.

Neville et al., "Anti-T cell immunotoxins: a look at post-endocytotic receptor-mediated routing," J Contr Rel, May 1993, 24:133-141.

Peraino et al. "Expression and purification of soluble porcine Ctla-4 in yeast Pichia pastoris," Protein Expr Purif., Apr. 2012, 82(2):270-278.

Perentesis et al., "Expression of diphtheria toxin fragment a and hormone-toxin fusion proteins in toxin-resistant yeast mutants," Proc. Natl. Acad. Sci., Nov. 1988, 85:8386-8390.

Salagianni et al., "NK cell adoptive transfer combined with Ontak-mediated regulatory T cell elimination induces effective adaptive antitumor immune responses," J. Immunol., Mar. 15, 2011,.

Song et al., "Preparation and characterization of fusion protein truncated Pseudomonas Exotoxin a (PE38KDEL) in Escherichia coli," Protein Expression and Purification, Nov. 2005, 44(1):5257.

Telang et al., "Phase Ii trial of the regulatory T cell-depleting agent, denileukin diftitox, in patients with unresectable stage Iv melanoma," Bmc, Cancer, 2011, 11:515.

Theuer et al., "A Recombinant Form of Pseudomonas Exotoxin Directed at the Epidermal Growth Factor Receptor That Is Cytotoxic without Requiring Proteolytic Processing," J. Biol. Chem., Aug. 25, 1992, 267(24):16872-16877.

Vallera, "Immunotoxins: Will Their Clinical Promise Be Fulfilled?," Blood, Jan. 15, 1994,.

Vitetta et al., "Immunotoxins: magic bullets or misguided missiles?," Immunology Today, May 1993, 14:148-154.

Wang et al., "Development of a diphtheria toxin based anti-porcine CD3 recombinant immunotoxin," Bioconjug Chem., Oct. 19, 2011, 22(10):2014-2020,.

Williams et al., "Diphtheria toxin receptor binding domain substitution with interleukin-2: genetic.construction and properties of a diphtheria toxin-related interleukin-2 fusion protein," Protein Engineering, 1987, 1(6):493-498.

Woo et al., "Gene optimization is necessary to express a bivalent anti-human anti-T cell immunotoxin in Pichia pastoris," Protein Expr. Purif., 2002, 25:270-282.

Yamada et al.,"Differential Effects of Denileukin Diftitox IL-2 Immunotoxin on NK and Regulatory T Cells in Nonhuman Primates," J. Immunol., 2012, 188:6063-70.

Zettlemeissl et al., "Expression of immunogenically reactive diphtheria toxin fusion proteins under the control of the PR promoter of bacteriophage lambda," Gene, 1986, 41(1):103-111.

Zhang et al., "Compatibility of porcine and human interleukin 2: implications for xenotransplantation," Xenotransplantation, Sep. 2006, 13(5):423-32.

International Search Report and Written Opinion mailed Apr. 24, 2014 in international application no. PC/US2013/073916, 9 pgs.

Sygmund et al. "Simple and efficient expression of *Agaricus meleagris*pyranose dehydrogenase in *Pichia pastoris*". Appl Microbiol Biotechnol., May 2012; 94(3):695-704.

Vallera et al. "Molecular modification of a recombinant, bivalent anti-human CD3 immunotoxin (Bic3) results in reduced in vivo toxicity in mice", Leuk. Res., Mar. 2005;29(3):331-41.

* cited by examiner

Figure 2

```
pIL-2-Gly        GCTCCAACTTCTTCCTCTACTAAGAACACTAAGAAGCAATTGGAGCCATTGTTGTTGGAC 60
pIL-2-Non-N-Gly  GCTCCAACTTCTTCCTCTACTAAGAACACTAAGAAGCAATTGGAGCCATTGTTGTTGGAC 60
                 ************************************************************ pIL-2-Gly        TTGCAATTGTTGTTGAAGGAGGTTAAGAACTACGAGAACGCTGACTTGTCTAGAATGTTG 120
pIL-2-Non-N-Gly  TTGCAATTGTTGTTGAAGGAGGTTAAGAACTACGAGAACGCTGACTTGTCTAGAATGTTG 120
                 ************************************************************ pIL-2-Gly        ACTTTCAAGTTCTACATGCCAAAGCAAGCTACTGAGTTGAAGCACTTGCAATGTTTGGTT 180
pIL-2-Non-N-Gly  ACTTTCAAGTTCTACATGCCAAAGCAAGCTACTGACTTGAACCACTTGCAATGTTTGCTT 180
                 *********************************  *  ******** pIL-2-Gly        GAGGAATTGAAGGCTTTGGAGGGTGTTTTGAACTTGGGTCAATCTAAGAACTCTGACTCC 240
pIL-2-Non-N-Gly  GAGGAATTGAAGGCTTTGGAGGGTGTTTTGAACTTGGGTCAATCTAAGAACTCTGACTCC 240
                 ************************************************************ pIL-2-Gly        GCTAACATTAAGGAGTCTATGAACAACATTAACGTTACTGTTTTGGAGTTGAAGGGTTCT 300
pIL-2-Non-N-Gly  GCTAACATTAAGGAGTCTATGAACAACATTGCTGTTACTGTTTTGGAGTTGAAGGGTTCT 300
                 ****************************   ************************* pIL-2-Gly        GAGACTTCTTTCAAGTGTGAGTACGACGACGAGACTGTTACTGCTGTTGAGTTCTTGAAC 360
pIL-2-Non-N-Gly  GAGACTTCTTTCAAGTGTGAGTACGACGACGAGACTGTTACTGCTGTTGAGTTCTTGAAC 360
                 ************************************************************ pIL-2-Gly        AAGTGGATTACTTTCTGTCAATCTATTTACTCTACTTTGACTCACCACCACCACCACCAC 420
pIL-2-Non-N-Gly  AAGTGGATTACTTTCTGTCAATCTATTTACTCTACTTTGACTCACCACCACCACCACCAC 420
                 ************************************************************
```

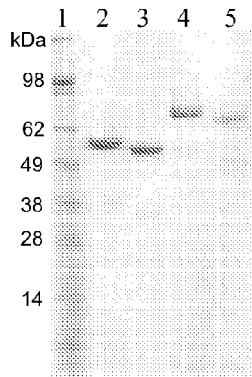

```
gctccaacttcttcctctacttcttcctctactgctgaggctcaacaacaacaacaa
 A  P  T  S  S  S  T  S  S  S  T  A  E  A  Q  Q  Q  Q  Q  Q
caacaacaacaacaacaacacttggagcaattgttgatggacttgcaagagttgttgtct
 Q  Q  Q  Q  Q  Q  H  L  E  Q  L  L  M  D  L  Q  E  L  L  S
agaatggagaactacagaaacttgaagttgccaagaatgttgactttcaagttctacttg
 R  M  E  N  Y  R  N  L  K  L  P  R  M  L  T  F  K  F  Y  L
ccaaagcaagctactgagttgaaggacttgcaatgtttggaggacgagttgggtccattg
 P  K  Q  A  T  E  L  K  D  L  Q  C  L  E  D  E  L  G  P  L
agacacgttttggacttgactcaatctaagtctttccaattggacgacgctgagaacttc
 R  H  V  L  D  L  T  Q  S  K  S  F  Q  L  E  D  A  E  N  F
atttctaacattagagttactgttgtcaagttgaagggttctgacaacactttcgagtgt
 I  S  N  I  R  V  T  V  V  K  L  K  G  S  D  N  T  F  E  C
caattcgacgacgagtctgctactgttgtcgacttcttgagaagatggattgctttctgt
 Q  F  D  D  E  S  A  T  V  V  D  F  L  R  R  W  I  A  F  C
caatctattatctctacttctccacaa
 Q  S  I  I  S  T  S  P  Q
```

Figure 11

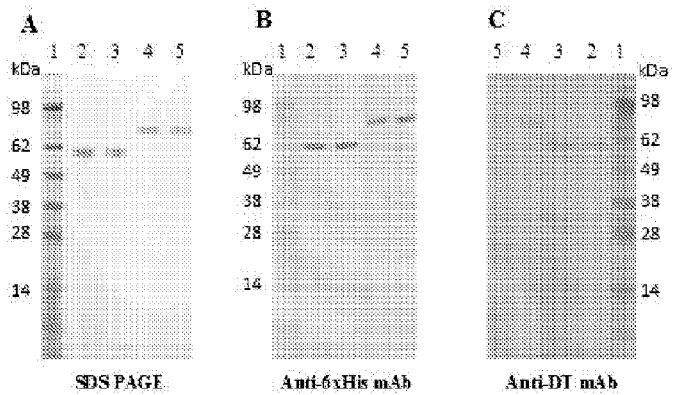

Figure 18

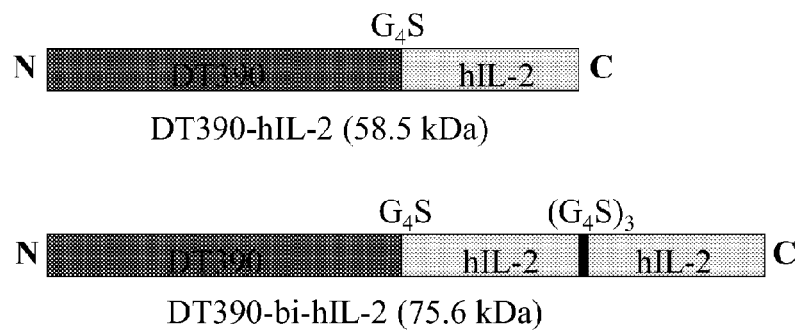

Figure 19

```
gctccaacttcttcttctactaagaagactcaattgcaattggagcacttgttgttggac
 A  P  T  S  S  S  T  K  K  T  Q  L  Q  L  E  H  L  L  L  D
ttgcaaatgatttgaacggtattaacaactacaagaacccaaagttgactagaatgttg
 L  Q  M  I  L  N  G  I  N  N  Y  K  N  P  K  L  T  R  M  L
actttcaagttctacatgccaaagaaggctactgagttgaagcacttgcaatgtttggag
 T  F  K  F  Y  M  P  K  K  A  T  E  L  K  H  L  Q  C  L  E
gaggaattgaagccattggaggaagttttgaacttggctcaatctaagaacttccacttg
 E  E  L  K  P  L  E  E  V  L  N  L  A  Q  S  K  N  F  H  L
agaccaagagacttgatttctaacattaacgttattgttttggagttgaagggttctgag
 R  P  R  D  L  I  S  N  I  N  V  I  V  L  E  L  K  G  S  E
actactttcatgtgtgagtacgctgacgagactgctactattgttgagttcttgaacaga
 T  T  F  M  C  E  Y  A  D  E  T  A  T  I  V  E  F  L  N  R
tggattactttctgtcaatctattatctctactttgact
 W  I  T  F  C  Q  S  I  I  S  T  L  T
```

Figures 20A-C
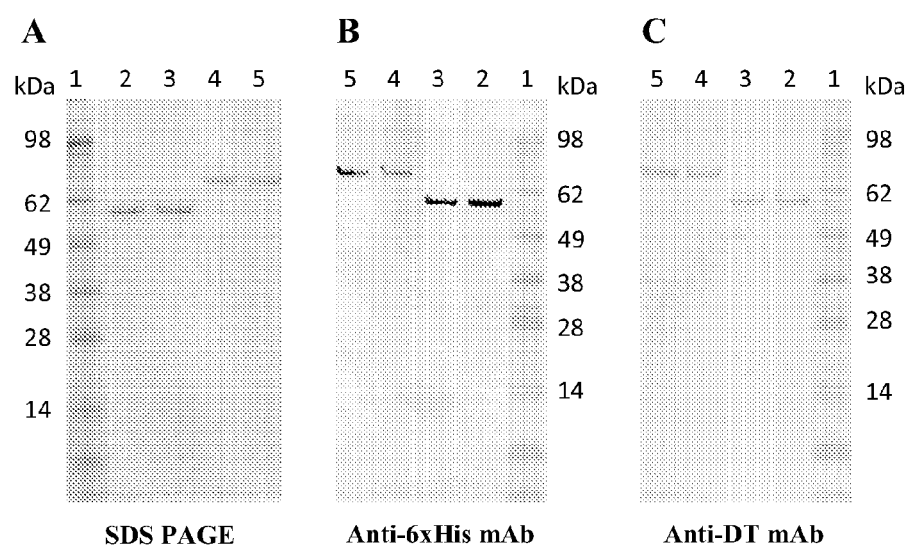

SEQUENCE LISTING

```
<160> NUMBER OF SEQ ID NOS: 31

<210> SEQ ID NO 1
<211> LENGTH: 153
<212> TYPE: PRT
<213> ORGANISM: Homo sapiens

<400> SEQUENCE: 1

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 2
<211> LENGTH: 399
<212> TYPE: DNA
<213> ORGANISM: Artificial Sequence
<220> FEATURE:
<223> OTHER INFORMATION: yeast codon-optimized sequence encoding human
      IL-2

<400> SEQUENCE: 2
gctccaactt cttcttctac taagaagact caattgcaat tggagcactt gttgttggac      60
ttgcaaatga ttttgaacgg tattaacaac tacaagaacc caaagttgac tagaatgttg     120
actttcaagt tctacatgcc aaagaaggct actgagttga agcacttgca atgtttggag     180
```

```
gaggaattga agccattgga ggaagttttg aacttggctc aatctaagaa cttccacttg    240
agaccaagag acttgatttc taacattaac gttattgttt tggagttgaa gggttctgag    300
actactttca tgtgtgagta cgctgacgag actgctacta ttgttgagtt cttgaacaga    360
tggattactt tctgtcaatc tattatctct actttgact                          399
```

<210> SEQ ID NO 3
<211> LENGTH: 133
<212> TYPE: PRT
<213> ORGANISM: Homo sapiens

<400> SEQUENCE: 3

```
Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 4
<211> LENGTH: 447
<212> TYPE: DNA
<213> ORGANISM: Artificial Sequence
<220> FEATURE:
<223> OTHER INFORMATION: yeast codon-optimized sequence encoding mouse
      IL-2

<400> SEQUENCE: 4

```
gctccaactt cttcctctac ttcttcctct actgctgagg ctcaacaaca acaacaacaa     60
caacaacaac aacaacaaca cttggagcaa ttgttgatgg acttgcaaga gttgttgtct    120
agaatggaga actacagaaa cttgaagttg ccaagaatgt tgactttcaa gttctacttg    180
ccaaagcaag ctactgagtt gaaggacttg caatgtttgg aggacgagtt gggtccattg    240
agacacgttt tggacttgac tcaatctaag tctttccaat ggaggacgc tgagaacttc    300 atttctaaca ttagagttac tgttgtcaag ttgaagggtt ctgacaacac tttcgagtgt    360
caattcgacg acgagtctgc tactgttgtc gacttcttga agatggat tgctttctgt    420 caatctatta tctctacttc tccacaa                                        447
```

<210> SEQ ID NO 5
<211> LENGTH: 149
<212> TYPE: PRT
<213> ORGANISM: Mus musculus

<400> SEQUENCE: 5

```
Ala Pro Thr Ser Ser Ser Thr Ser Ser Ser Thr Ala Glu Ala Gln Gln
```

```
              1               5              10              15
            Gln Gln Gln Gln Gln Gln Gln Gln Gln His Leu Glu Gln Leu Leu
                           20                  25                  30

Met Asp Leu Gln Glu Leu Leu Ser Arg Met Glu Asn Tyr Arg Asn Leu
                           35                  40                  45

Lys Leu Pro Arg Met Leu Thr Phe Lys Phe Tyr Leu Pro Lys Gln Ala
                           50                  55                  60

Thr Glu Leu Lys Asp Leu Gln Cys Leu Glu Asp Glu Leu Gly Pro Leu
            65                  70                  75                  80

Arg His Val Leu Asp Leu Thr Gln Ser Lys Ser Phe Gln Leu Glu Asp
                                85                  90                  95

Ala Glu Asn Phe Ile Ser Asn Ile Arg Val Thr Val Val Lys Leu Lys
                               100                 105                 110

Gly Ser Asp Asn Thr Phe Glu Cys Gln Phe Asp Asp Glu Ser Ala Thr
                               115                 120                 125

Val Val Asp Phe Leu Arg Arg Trp Ile Ala Phe Cys Gln Ser Ile Ile
                               130                 135                 140

Ser Thr Ser Pro Gln
            145
```

<210> SEQ ID NO 6
<211> LENGTH: 420
<212> TYPE: DNA
<213> ORGANISM: Artificial Sequence
<220> FEATURE:
<223> OTHER INFORMATION: yeast Codon-optimized glycosylated porcine IL-2

<400> SEQUENCE: 6

```
gctccaactt cttcctctac taagaacact aagaagcaat ggagccatt gttgttggac      60
ttgcaattgt tgttgaagga ggttaagaac tacgagaacg ctgacttgtc tagaatgttg    120
actttcaagt tctacatgcc aaagcaagct actgagttga agcacttgca atgtttggtt    180
gaggaattga aggctttgga gggtgttttg aacttgggtc aatctaagaa ctctgactcc    240
gctaacatta aggagtctat gaacaacatt aacgttactg ttttggagtt gaagggttct    300
gagacttctt tcaagtgtga gtacgacgac gagactgtta ctgctgttga gttcttgaac    360
aagtggatta cttttctgtca atctatttac tctactttga ctcaccacca ccaccaccac    420
```

<210> SEQ ID NO 7
<211> LENGTH: 420
<212> TYPE: DNA
<213> ORGANISM: Artificial Sequence
<220> FEATURE:
<223> OTHER INFORMATION: non-N-glycosylated porcine IL-2

<400> SEQUENCE: 7

```
gctccaactt cttcctctac taagaacact aagaagcaat ggagccatt gttgttggac      60
ttgcaattgt tgttgaagga ggttaagaac tacgagaacg ctgacttgtc tagaatgttg    120
actttcaagt tctacatgcc aaagcaagct actgagttga agcacttgca atgtttggtt    180
gaggaattga aggctttgga gggtgttttg aacttgggtc aatctaagaa ctctgactcc    240
gctaacatta aggagtctat gaacaacatt gctgttactg ttttggagtt gaagggttct    300
gagacttctt tcaagtgtga gtacgacgac gagactgtta ctgctgttga gttcttgaac    360
aagtggatta cttttctgtca atctatttac tctactttga ctcaccacca ccaccaccac    420
```

<210> SEQ ID NO 8

```
<211> LENGTH: 8
<212> TYPE: PRT
<213> ORGANISM: Artificial Sequence
<220> FEATURE:
<223> OTHER INFORMATION: epitope tag

<400> SEQUENCE: 8

Asp Tyr Lys Asp Asp Asp Asp Lys
 1               5

<210> SEQ ID NO 9
<211> LENGTH: 6
<212> TYPE: PRT
<213> ORGANISM: Artificial Sequence
<220> FEATURE:
<223> OTHER INFORMATION: epitope tag

<400> SEQUENCE: 9

Tyr Pro Tyr Asp Val Pro
 1               5

<210> SEQ ID NO 10
<211> LENGTH: 10
<212> TYPE: PRT
<213> ORGANISM: Artificial Sequence
<220> FEATURE:
<223> OTHER INFORMATION: epitope tag

<400> SEQUENCE: 10

Ile Leu Lys Lys Ala Thr Ala Tyr Ile Leu
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: epitope tag

<400> SEQUENCE: 11

Glu Gln Lys Leu Ile Ser Glu Glu Asp Leu
 1               5                  10

<210> SEQ ID NO 12
<211> LENGTH: 36
<212> TYPE: DNA
<213> ORGANISM: Artificial Sequence
<220> FEATURE:
<223> OTHER INFORMATION: synthetically generated primer

<400> SEQUENCE: 12
ccgctcgagc catgggctcc aacttcttcc tctact                            36

<210> SEQ ID NO 13
<211> LENGTH: 63
<212> TYPE: DNA
<213> ORGANISM: Artificial Sequence
<220> FEATURE:
<223> OTHER INFORMATION: synthetically generated primer

<400> SEQUENCE: 13
ccggaattcg gatccaccac caccagaacc accaccacca gtcaaagtag agtaaataga    60
ttg                                                               63

<210> SEQ ID NO 14
<211> LENGTH: 51
```

```
<212> TYPE: DNA
<213> ORGANISM: Artificial Sequence
<220> FEATURE:
<223> OTHER INFORMATION: synthetically generated primer

<400> SEQUENCE: 14
ccgctcgagg gatccggtgg tggtggttct gctccaactt cttcctctac t          51

<210> SEQ ID NO 15
<211> LENGTH: 54
<212> TYPE: DNA
<213> ORGANISM: Artificial Sequence
<220> FEATURE:
<223> OTHER INFORMATION: synthetically generated primer

<400> SEQUENCE: 15
ccggaattct tagtggtggt ggtggtggtg agtcaaagta gagtaaatag attg       54

<210> SEQ ID NO 16
<211> LENGTH: 45
<212> TYPE: DNA
<213> ORGANISM: Artificial Sequence
<220> FEATURE:
<223> OTHER INFORMATION: synthetically generated primer

<400> SEQUENCE: 16
aaggagtcta tgaacaacat tgctgttact gttttggagt tgaag                 45

<210> SEQ ID NO 17
<211> LENGTH: 45
<212> TYPE: DNA
<213> ORGANISM: Artificial Sequence
<220> FEATURE:
<223> OTHER INFORMATION: synthetically generated primer

<400> SEQUENCE: 17
cttcaactcc aaaacagtaa cagcaatgtt gttcatagac tcctt                 45

<210> SEQ ID NO 18
<211> LENGTH: 51
<212> TYPE: DNA
<213> ORGANISM: Artificial Sequence
<220> FEATURE:
<223> OTHER INFORMATION: synthetically generated primer

<400> SEQUENCE: 18
ccgctcgagc catggggtgg tggtggttct gctccaactt cttcctctac t          51

<210> SEQ ID NO 19
<211> LENGTH: 66
<212> TYPE: DNA
<213> ORGANISM: Artificial Sequence
<220> FEATURE:
<223> OTHER INFORMATION: synthetically generated primer

<400> SEQUENCE: 19
ccggaattcc gccgcggatc caccaccacc agaaccacca ccaccttgtg gagaagtaga  60
gataat                                                            66

<210> SEQ ID NO 20
<211> LENGTH: 57
<212> TYPE: DNA
<213> ORGANISM: Artificial Sequence
<220> FEATURE:
<223> OTHER INFORMATION: synthetically generated primer
```

<400> SEQUENCE: 20
ccgctcgagc ggcgcggatc cggtggtggt ggttctgctc caacttcttc ctctact    57

<210> SEQ ID NO 21
<211> LENGTH: 54
<212> TYPE: DNA
<213> ORGANISM: Artificial Sequence
<220> FEATURE:
<223> OTHER INFORMATION: synthetically generated primer

<400> SEQUENCE: 21
ccggaattct tagtggtggt ggtggtggtg ttgtggagaa gtagagataa taga    54

<210> SEQ ID NO 22
<211> LENGTH: 51
<212> TYPE: DNA
<213> ORGANISM: Artificial Sequence
<220> FEATURE:
<223> OTHER INFORMATION: synthetically generated primer

<400> SEQUENCE: 22
ccgctcgagc catggggtgg tggtggttct gctccaactt cttcttctac t    51

<210> SEQ ID NO 23
<211> LENGTH: 69
<212> TYPE: DNA
<213> ORGANISM: Artificial Sequence
<220> FEATURE:
<223> OTHER INFORMATION: synthetically generated primer

<400> SEQUENCE: 23
ccggaattcc gccgcggatc caccaccacc agaaccacca ccaccagtca aagtagagat    60
aatagattg    69

<210> SEQ ID NO 24
<211> LENGTH: 57
<212> TYPE: DNA
<213> ORGANISM: Artificial Sequence
<220> FEATURE:
<223> OTHER INFORMATION: synthetically generated primer

<400> SEQUENCE: 24
ccgctcgagc gggcgggatc cggtggtggt ggttctgctc caacttcttc ttctact    57

<210> SEQ ID NO 25
<211> LENGTH: 54
<212> TYPE: DNA
<213> ORGANISM: Artificial Sequence
<220> FEATURE:
<223> OTHER INFORMATION: synthetically generated primer

<400> SEQUENCE: 25
ccggaattct tagtggtggt ggtggtggtg agtcaaagta gagataatag attg    54

<210> SEQ ID NO 26
<211> LENGTH: 447
<212> TYPE: DNA
<213> ORGANISM: Artificial Sequence
<220> FEATURE:
<223> OTHER INFORMATION: cDNA encoding mouse il-2

<400> SEQUENCE: 26
gctccaactt cttcctctac ttcttcctct actgctgagg ctcaacaaca acaacaacaa    60
caacaacaac aacaacaaca cttggagcaa ttgttgatgg acttgcaaga gttgttgtct    120

```
agaatggaga actacagaaa cttgaagttg ccaagaatgt tgactttcaa gttctacttg      180
ccaaagcaag ctactgagtt gaaggacttg caatgtttgg aggacgagtt gggtccattg      240
agacacgttt tggacttgac tcaatctaag tctttccaat ggaggacgc tgagaacttc       300 atttctaaca ttagagttac tgttgtcaag ttgaagggtt ctgacaacac tttcgagtgt      360
caattcgacg acgagtctgc tactgttgtc gacttcttga agatggat tgctttctgt        420 caatctatta tctctacttc tccacaa                                          447

<210> SEQ ID NO 27
<211> LENGTH: 399
<212> TYPE: DNA
<213> ORGANISM: Artificial Sequence
<220> FEATURE:
<223> OTHER INFORMATION: cDNA encoding human il-2

<400> SEQUENCE: 27
gctccaactt cttcttctac taagaagact caattgcaat ggagcacttg ttgttggac       60 ttgcaaatga ttttgaacgg tattaacaac tacaagaacc caaagttgac tagaatgttg     120
actttcaagt tctacatgcc aaagaaggct actgagttga agcacttgca atgtttggag     180
gaggaattga agccattgga ggaagttttg aacttggctc aatctaagaa cttccacttg     240
agaccaagag acttgatttc taacattaac gttattgttt tggagttgaa gggttctgag     300
actactttca tgtgtgagta cgctgacgag actgctacta tgttgagtt cttgaacaga      360 tggattactt tctgtcaatc tattatctct actttgact                            399

<210> SEQ ID NO 28
<211> LENGTH: 553
<212> TYPE: PRT
<213> ORGANISM: Artificial Sequence
<220> FEATURE:
<223> OTHER INFORMATION: monovalent murine IL-2 fusion toxin

<400> SEQUENCE: 28

Ala Gly Ala Asp Asp Val Val Asp Ser Ser Lys Ser Phe Val Met Glu
  1               5                  10                  15

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Phe His Gln Thr Ala Leu
            245                 250                 255

Glu His Pro Glu Leu Ser Glu Leu Lys Thr Val Thr Gly Thr Asn Pro
        260                 265                 270

Val Phe Ala Gly Ala Asn Tyr Ala Ala Trp Ala Val Asn Val Ala Gln
    275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
            325                 330                 335

Ser Ser Leu Met Val Ala Gln Ala Ile Pro Leu Val Gly Glu Leu Val
        340                 345                 350

Asp Ile Gly Phe Ala Ala Tyr Asn Phe Val Glu Ser Ile Ile Asn Leu
    355                 360                 365

Phe Gln Val Val His Asn Ser Tyr Asn Arg Pro Ala Tyr Ser Pro Gly
    370                 375                 380

His Lys Thr Gln Pro Phe Leu Pro Trp Gly Gly Gly Ser Ala Pro
385                 390                 395                 400

Thr Ser Ser Ser Thr Ser Ser Thr Ala Glu Ala Gln Gln Gln Gln
            405                 410                 415

Gln Gln Gln Gln Gln Gln Gln His Leu Glu Gln Leu Leu Met Asp
        420                 425                 430

Leu Gln Glu Leu Leu Ser Arg Met Glu Asn Tyr Arg Asn Leu Lys Leu
    435                 440                 445

Pro Arg Met Leu Thr Phe Lys Phe Tyr Leu Pro Lys Gln Ala Thr Glu
450                 455                 460

Leu Lys Asp Leu Gln Cys Leu Glu Asp Glu Leu Gly Pro Leu Arg His
465                 470                 475                 480

Val Leu Asp Leu Thr Gln Ser Lys Ser Phe Gln Leu Glu Asp Ala Glu
            485                 490                 495

Asn Phe Ile Ser Asn Ile Arg Val Thr Val Val Lys Leu Lys Gly Ser
        500                 505                 510

Asp Asn Thr Phe Glu Cys Gln Phe Asp Asp Glu Ser Ala Thr Val Val
    515                 520                 525

Asp Phe Leu Arg Arg Trp Ile Ala Phe Cys Gln Ser Ile Ile Ser Thr
    530                 535                 540

Ser Pro Gln His His His His His
545                 550

<210> SEQ ID NO 29
<211> LENGTH: 717
<212> TYPE: PRT
<213> ORGANISM: Artificial Sequence
<220> FEATURE:

-continued

<223> OTHER INFORMATION: Bivalent murine IL-2 fusion toxin

<400> SEQUENCE: 29

```
Ala Gly

```
Thr Ser Ser Ser Thr Ser Ser Thr Ala Glu Ala Gln Gln Gln Gln
                405                 410                 415
Gln Gln Gln Gln Gln Gln Gln Gln His Leu Glu Gln Leu Leu Met Asp
            420                 425                 430
Leu Gln Glu Leu Leu Ser Arg Met Glu Asn Tyr Arg Asn Leu Lys Leu
        435                 440                 445
Pro Arg Met Leu Thr Phe Lys Phe Tyr Leu Pro Lys Gln Ala Thr Glu
    450                 455                 460
Leu Lys Asp Leu Gln Cys Leu Glu Asp Glu Leu Gly Pro Leu Arg His
465                 470                 475                 480
Val Leu Asp Leu Thr Gln Ser Lys Ser Phe Gln Leu Glu Asp Ala Glu
                485                 490                 495
Asn Phe Ile Ser Asn Ile Arg Val Thr Val Val Lys Leu Lys Gly Ser
            500                 505                 510
Asp Asn Thr Phe Glu Cys Gln Phe Asp Asp Glu Ser Ala Thr Val Val
        515                 520                 525
Asp Phe Leu Arg Arg Trp Ile Ala Phe Cys Gln Ser Ile Ile Ser Thr
    530                 535                 540
Ser Pro Gln Gly Gly Gly Ser Gly Gly Gly Ser Gly Gly Gly
545                 550                 555                 560
Gly Ser Ala Pro Thr Ser Ser Thr Ser Ser Thr Ala Glu Ala
                565                 570                 575
Gln Gln Gln Gln Gln Gln Gln Gln Gln Gln His Leu Glu Gln
            580                 585                 590
Leu Leu Met Asp Leu Gln Glu Leu Leu Ser Arg Met Glu Asn Tyr Arg
        595                 600                 605
Asn Leu Lys Leu Pro Arg Met Leu Thr Phe Lys Phe Tyr Leu Pro Lys
    610                 615                 620
Gln Ala Thr Glu Leu Lys Asp Leu Gln Cys Leu Glu Asp Glu Leu Gly
625                 630                 635                 640
Pro Leu Arg His Val Leu Asp Leu Thr Gln Ser Lys Ser Phe Gln Leu
                645                 650                 655
Glu Asp Ala Glu Asn Phe Ile Ser Asn Ile Arg Val Thr Val Val Lys
            660                 665                 670
Leu Lys Gly Ser Asp Asn Thr Phe Glu Cys Gln Phe Asp Asp Glu Ser
        675                 680                 685
Ala Thr Val Val Asp Phe Leu Arg Arg Trp Ile Ala Phe Cys Gln Ser
    690                 695                 700
Ile Ile Ser Thr Ser Pro Gln His His His His His
705                 710                 715

<210> SEQ ID NO 30
<211> LENGTH: 537
<212> TYPE: PRT
<213> ORGANISM: Artificial Sequence
<220> FEATURE:
<223> OTHER INFORMATION: Monovalent human IL-2 fusion toxin

<400> SEQUENCE: 30

Ala Gly Ala Asp Asp Val Val Asp Ser Ser Lys Ser Phe Val Met Glu
1               5                   10                  15
Asn Phe Ala Ser Tyr His Gly Thr Lys Pro Gly Tyr Val Asp Ser Ile
            20                  25                  30
Gln Lys Gly Ile Gln Lys Pro Lys Ser Gly Thr Gln Gly Asn Tyr Asp
        35                  40                  45
```

```
Asp Asp Trp Lys Gly Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
             100                 105                 110

Glu Pro Leu Met Glu Gln Val Gly Thr Glu Glu Phe Ile Lys Arg Phe
         115                 120                 125

Gly Asp Gly Ala Ser Arg Val Val Leu Ser Leu Pro Phe Ala Glu Gly
130                 135                 140

Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr Gln Pro Phe Leu Pro Trp Gly Gly Gly Ser Ala Pro
385                 390                 395                 400

Thr Ser Ser Ser Thr Lys Lys Thr Gln Leu Gln Leu Glu His Leu Leu
                405                 410                 415

Leu Asp Leu Gln Met Ile Leu Asn Gly Ile Asn Asn Tyr Lys Asn Pro
            420                 425                 430

Lys Leu Thr Arg Met Leu Thr Phe Lys Phe Tyr Met Pro Lys Lys Ala
        435                 440                 445

Thr Glu Leu Lys His Leu Gln Cys Leu Glu Glu Glu Leu Lys Pro Leu
450                 455                 460

Glu Glu Val Leu Asn Leu Ala Gln Ser Lys Asn Phe His Leu Arg Pro
```

```
              465                 470                 475                 480

Arg Asp Leu Ile Ser Asn Ile Asn Val Ile Val Leu Glu Leu Lys Gly
                    485                 490                 495

Ser Glu Thr Thr Phe Met Cys Glu Tyr Ala Asp Glu Thr Ala Thr Ile
                500                 505                 510

Val Glu Phe Leu Asn Arg Trp Ile Thr Phe Cys Gln Ser Ile Ile Ser
            515                 520                 525

Thr Leu Thr His His His His His His
        530                 535

<210> SEQ ID NO 31
<211> LENGTH: 685
<212> TYPE: PRT
<213> ORGANISM: Artificial Sequence
<220> FEATURE:
<223> OTHER INFORMATION: Bivalent human IL-2 fusion toxin

<400> SEQUENCE: 31

Ala Gly Ala Asp Asp Val Val Asp Ser Ser Lys Ser Phe Val Met Glu
  1               5                  10                  15

Asn Phe Ala Ser Tyr His Gly Thr Lys Pro Gly Tyr Val Asp Ser Ile
             20                  25                  30

Gln Lys Gly Ile Gln Lys Pro Lys Ser Gly Thr Gln Gly Asn Tyr Asp
         35                  40                  45

Asp Asp Trp Lys Gly Phe Tyr Ser Thr Asp Asn Lys Tyr Asp Ala Ala
     50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Ala Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

```
Val Ile Asp Ser Glu Thr Ala Asp Asn Leu Glu Lys Thr Ala Ala
    290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
    370                 375                 380
His Lys Thr Gln Pro Phe Leu Pro Trp Gly Gly Gly Ser Ala Pro
385                 390                 395                 400
Thr Ser Ser Ser Thr Lys Lys Thr Gln Leu Gln Leu Glu His Leu Leu
                405                 410                 415
Leu Asp Leu Gln Met Ile Leu Asn Gly Ile Asn Asn Tyr Lys Asn Pro
            420                 425                 430
Lys Leu Thr Arg Met Leu Thr Phe Lys Phe Tyr Met Pro Lys Lys Ala
        435                 440                 445
Thr Glu Leu Lys His Leu Gln Cys Leu Glu Glu Glu Leu Lys Pro Leu
    450                 455                 460
Glu Glu Val Leu Asn Leu Ala Gln Ser Lys Asn Phe His Leu Arg Pro
465                 470                 475                 480
Arg Asp Leu Ile Ser Asn Ile Asn Val Ile Val Leu Glu Leu Lys Gly
                485                 490                 495
Ser Glu Thr Thr Phe Met Cys Glu Tyr Ala Asp Glu Thr Ala Thr Ile
            500                 505                 510
Val Glu Phe Leu Asn Arg Trp Ile Thr Phe Cys Gln Ser Ile Ile Ser
        515                 520                 525
Thr Leu Thr Gly Gly Gly Gly Ser Gly Gly Gly Gly Ser Gly Gly Gly
    530                 535                 540
Gly Ser Ala Pro Thr Ser Ser Ser Thr Lys Lys Thr Gln Leu Gln Leu
545                 550                 555                 560
Glu His Leu Leu Leu Asp Leu Gln Met Ile Leu Asn Gly Ile Asn Asn
                565                 570                 575
Tyr Lys Asn Pro Lys Leu Thr Arg Met Leu Thr Phe Lys Phe Tyr Met
            580                 585                 590
Pro Lys Lys Ala Thr Glu Leu Lys His Leu Gln Cys Leu Glu Glu Glu
        595                 600                 605
Leu Lys Pro Leu Glu Glu Val Leu Asn Leu Ala Gln Ser Lys Asn Phe
    610                 615                 620
His Leu Arg Pro Arg Asp Leu Ile Ser Asn Ile Asn Val Ile Val Leu
625                 630                 635                 640
Glu Leu Lys Gly Ser Glu Thr Thr Phe Met Cys Glu Tyr Ala Asp Glu
                645                 650                 655
Thr Ala Thr Ile Val Glu Phe Leu Asn Arg Trp Ile Thr Phe Cys Gln
            660                 665                 670
Ser Ile Ile Ser Thr Leu Thr His His His His His
        675                 680                 685
```

BIVALENT IL-2 FUSION TOXINS

CLAIM OF PRIORITY

This application is a U.S. National Phase Application under 35 U.S.C. §371 of International Patent Application No. PCT/US2013/073916, filed on Dec. 9, 2013, which claims the benefit of U.S. patent application Ser. No. 61/735,497, filed on Dec. 10, 2012. The entire contents of the foregoing are hereby incorporated by reference.

TECHNICAL FIELD

This invention relates to bivalent-IL2 fusion toxins, and methods of use thereof.

BACKGROUND

Regulatory T cells (Tregs) have been recognized as an important subset of T cells, and modulation of Tregs has been used in transplantation tolerance induction, autoimmune disease treatment, and cancer treatment. Antigen-specific immune responses such as those targeted against tumors are suppressed by Tregs characterized by $CD4^+CD25^{high}FoxP3^+$ expression. $CD25^+$Treg depletion combined with tumor vaccination is a potentially promising approach to improve cancer treatment.

SUMMARY

At least in part, the present invention is based on the discovery that a bivalent-IL2 fusion toxin has improved activity as compared to a monovalent IL-2 fusion toxin. In in vitro protein synthesis inhibition assays and cell proliferation assays, the bivalent version was superior to monovalent versions. In vivo functional analysis demonstrated that a bi-porcine IL2 fusion toxin prolonged the average life-span of tumor-bearing animals significantly using a porcine CD25-expressing B-cell lymphoma NOD/SCID IL-2 receptor $\gamma^{-/-}$ (NSG) mouse model. This recombinant protein can be used for in vivo T-reg depletion to relieve repression of anti-tumor immune responses to treat cancer; and as a research tool to study immune regulation, tolerance induction, and autoimmune disease.

Thus, in a first aspect, the invention provides bivalent IL-2 fusion toxins comprising a first part comprising a cytotoxic protein, and a second part comprising at least two Interleukin 2 (IL-2) sequences, e.g., two human IL-2 sequences comprising amino acids 21-153 of SEQ ID NO:1, optionally with one or both of a linker between the two IL-2 sequences, and a linker between the first and second parts. In some embodiments, the fusion toxin comprises SEQ ID NO:31. In some embodiments, the fusion toxin is at least 80%, 90%, 95%, or 99% identical to SEQ ID NO:31; such a fusion toxin that is at least 80% identical to SEQ ID NO:31 will retain the ability to bind CD25+ cells and reduce protein synthesis and/or cell proliferation using an assay as described herein.

In some embodiments, the cytotoxic protein comprises diphtheria toxin, *Pseudomonas* exotoxin, or cytotoxic portions or variants thereof.

In some embodiments, the fusion toxins include a linker between the first and second parts.

In another aspect, the invention provides nucleic acid molecules, e.g., codon-optimized nucleic acid molecules (e.g., optimized for expression in a methylotropic yeast, e.g., of the species *Pichia Pastoris*), that encode the fusion toxins described herein, as well as vectors comprising the nucleic acid molecules, and host cells comprising and/or expressing the nucleic acid molecules.

In some embodiments, the host cell is a methylotropic yeast.

In some embodiments, the host cell is a cell of the species *Pichia Pastoris*.

In another aspect, the invention provides pharmaceutical compositions comprising the fusion toxins described herein, and a physiologically acceptable carrier.

In a further aspect, the invention provides methods for treating a subject who has a cancer, the method comprising administering to the subject a therapeutically effective amount of a fusion toxin described herein.

In some embodiments, the cancer comprises cancer cells that express CD25, e.g., is selected from the group consisting of B-cell neoplasms, acute nonlymphocytic leukemias, neuroblastomas, tumor infiltrating lymphocytes, and cutaneous T cell lymphoma.

In some embodiments, the methods include administering an immunotherapy to the subject. In some embodiments, the immunotherapy comprises administration of one or more of: dendritic cells or peptides with adjuvant; DNA-based vaccines; cytokines (e.g., IL-2); cyclophosphamide; anti-interleukin-2R immunotoxins; antibodies; virus-based vaccines (e.g., adenovirus); formulations of Toll-like Receptor or RIG-I-like receptor ligands; or adoptive T cell therapy or other cell therapy.

In another aspect, the invention provides the fusion toxins described herein, or nucleic acid molecules encoding the fusion toxins, for use in the treatment of a cancer comprising cancer cells that express CD25. In some embodiments, the cancer is selected from the group consisting of B-cell neoplasms, acute nonlymphocytic leukemias, neuroblastomas, tumor infiltrating lymphocytes, and cutaneous T cell lymphoma.

Also provided herein are methods for depleting CD25-expressing (CD25+) regulatory T cells in a subject. The methods include administering to the subject an effective amount of a fusion toxin as described herein, or a nucleic acid encoding the fusion toxin.

In some embodiments, the subject has cancer, or is an experimental model of autoimmune disease or transplant rejection.

In a further aspect, the invention provides methods for producing bivalent IL-2 fusion toxins. The methods include expressing a codon-optimized nucleic acid molecule encoding the fusion toxin of claims 1-3 in a methylotropic yeast; and substantially purifying the fusion toxin, thereby producing the composition. In some embodiments, the methylotropic yeast is of the species *Pichia Pastoris*.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2. Codon-optimized glycosylated (SEQ ID NO:6) and non-N-glycosylated (SEQ ID NO:7) porcine IL-2 DNA sequence. The asparagine at position 91 (unique N-linked glycosylation site) was replaced with alanine (N91A, AAC→GCT) for non-N-glycosylated porcine IL-2. The * denotes the same nucleotide sequence between porcine IL-2-Gly and porcine IL-2-Non-N-Gly.

FIG. 3. SDS PAGE Gel (4-12% NuPAGE) Analysis of the Four Porcine IL-2 Fusion Toxins. Lane 1: Protein marker; Lane 2: DT390-pIL-2-Gly (58.7 kDa); Lane 3: DT390-pIL-2-Non-N-Gly (58.7 kDa); Lane 4: DT390-bi-pIL-2-Gly (75 kDa); Lane 5: DT390-bi-pIL-2-Non-N-Gly (75 kDa). The weak bands in lanes 2-5 at the lower positions are the break-down products between the diphtheria toxin (DT) A chain and the DT B chain which are linked by disulfide-bonds. The weak bands in lanes 2-5 at ~21 kDa are the DT A chains; the weak band in lane 2 at ~38 kDa is DT B chain-pIL-2-Gly; the weak band in lane 3 at ~33 kDa is DT B chain-pIL-2-Non-N-Gly; the weak band in lane 4 at ~54 kDa is DT B-chain-bi-pIL-2-Gly; the weak band in lane 5 at ~49 kDa is DT-B chain-bi-pIL-2-Non-N-Gly.

FIG. 10. Codon-optimized murine IL-2 DNA sequence (SEQ ID NO:26) and encoded murine IL-2 protein (SEQ ID NO:5).

FIGS. 11A-C. SDS PAGE and Western blot analysis of the murine IL-2 fusion toxins. A) SDS PAGE analysis (4-12% NuPAGE, Invitrogen); B) Western blot analysis using mouse anti-His mAb (clone #: 4A12E4, Invitrogen). C) Western blot analysis using mouse anti-diphtheria toxin mAb (clone #: 3B6, Meridian). Lane 1: Protein marker; Lane 2-3: DT390-mIL-2 (61.11 kDa); Lane 4-5: DT390-bi-mIL (79.27 kDa).

FIG. 18. Schematic representation of the monovalent and bivalent human IL-2 fusion toxins.

FIG. 19. Codon-optimized human IL-2 cDNA sequence (SEQ ID NO: 27) and encoded human protein sequence (SEQ ID NO:3).

FIGS. 20A-C. SDS PAGE and Western blot of the human IL-2 fusion toxins. A) SDS PAGE analysis (4-12% NuPAGE, Invitrogen); B) Western blot analysis using a mouse anti-His mAb (clone #: 4A12E4, Invitrogen); C) Western blot analysis using a mouse anti-diphtheria toxin mAb (clone #3B6, Meridian). Lane 1: Protein marker; Lane 2-3: DT390-hIL-2 (58.5 kDa); Lane 4-5: DT390-bi-hIL (75.6 kDa).

DETAILED DESCRIPTION

Figure 1:
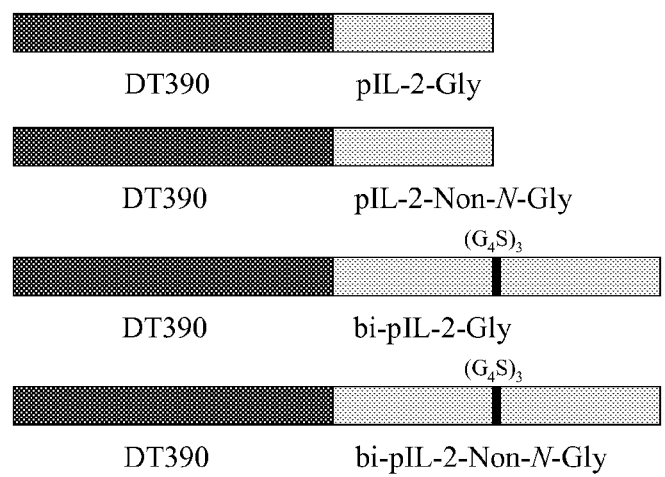
FIG. 1. Schematic Representation of Four exemplary Porcine IL-2 Fusion Toxins.

Regulatory T cells (Tregs) have been widely recognized as crucial players in controlling immune responses. Because their major role is to ensure that the immune system is not over reactive, Tregs have been the focus of multiple research studies including those investigating transplantation tolerance, autoimmunity and cancer treatment. An effective reagent capable of depleting Treg in vivo would facilitate better cancer treatment and allow mechanistic studies of the role of Treg in transplantation tolerance and the development of autoimmune disease.

On their surface, Tregs constitutively express high levels of the high affinity interleukin-2 receptor (IL-2R) consisting of IL-2Rα (CD25) together with IL-2Rβ (CD122) and the common γ-chain (CD132). Described herein are a novel bivalent human IL-2 fusion toxin and a monovalent human IL-2 fusion toxin, and the functional activity of these reagents in vitro. As shown in Example 3, genetically linking two human IL-2 domains in tandem, thereby generating a bivalent fusion toxin, results in significantly improved capacity in targeting human CD25$^+$ cells in vitro. Binding analysis by flow cytometry showed that the bivalent human IL-2 fusion toxin has notably increased affinity for human CD25$^+$ cells. In vitro functional analysis demonstrated that the bivalent isoform has an increased potency of approximately 2 logs in inhibiting cellular proliferation and protein synthesis in human CD25$^+$ cells compared to the monovalent human IL-2 fusion toxin. Additionally, two inhibition assays were performed in order to verify that the fusion toxins target the cells specifically through binding of the human IL-2 domain of the fusion toxin to the human IL-2 receptor on the cell surface. These results demonstrated that 1) both monovalent and bivalent human IL-2 fusion toxins are capable of blocking the binding of biotinylated human IL-2 to human CD25 by flow cytometry; and 2) human IL-2 blocked the fusion toxins from inhibiting protein synthesis and cellular proliferation in vitro, thus confirming that the human IL-2 fusion toxins target the cells specifically through binding to the human IL-2 receptor. Thus the bivalent human IL-2 fusion toxin is expected to be a more potent, and therefore more optimal, agent than the current clinically-used monovalent fusion toxin (denileukin diftitox, Ontak®) for in vivo depletion of Tregs.

The exemplary reagents constructed in this study were generated by genetically linking one, two or more, preferably two, IL-2 polypeptides to a toxin, e.g., the truncated diphtheria toxin (DT390). Without wishing to be bound by theory, this reagent is believed to function by first binding to the cell surface via the IL-2/CD25 interaction, then the toxin, e.g., DT390 domain, is internalized followed by inhibition of protein synthesis resulting in cell death. Monovalent and bivalent human, murine, and porcine fusion toxins were created. Human and murine IL-2 amino acid sequences have 64% homology, which explains the observation of difference in cross-species reactivity between human IL-2 and murine IL-2 (Collins 1989). Human IL-2 is 10 times less effective than murine IL-2 in stimulation of murine T cells (Collins 1989). Therefore it is hypothesized that a species-specific murine IL-2 fusion toxin will deplete murine Treg in vivo more effectively.

In some of the present exemplary constructs, porcine IL-2 was used; as the porcine version includes an N-linked glycosylation site, a version in which that site was mutated was also used. Thus, four versions of the porcine IL-2 fusion toxin were designed in an interest to find the most effective isoform: 1) monovalent glycosylated IL-2 fusion toxin (Gly); 2) monovalent non-N-glycosylated IL-2 fusion toxin (NonGly); 3) bivalent glycosylated IL-2 fusion toxin (Bi-Gly); 4) bivalent non-N-glycosylated IL-2 fusion toxin (Bi-NonGly). Using a porcine CD25+ B cell lymphoma cell line (LCL13271), in vitro analysis of the fusion toxins' ability to inhibit protein synthesis demonstrated that the Bi-NonGly fusion toxin is the most efficient reagent. These in vitro results are consistent with binding affinity as the Bi-NonGly fusion toxin binds strongest to CD25 on the same LCL13271 cells. The Bi-Gly fusion toxin significantly prolonged the survival (p=0.028) of tumor-bearing NOD/SCID IL-2 receptor γ−/− (NSG) mice injected with LCL13271 cells compared with untreated controls. The recombinant proteins described herein also have great potential as a useful tool for in vivo depletion of CD25+ cells for studying immune regulation, e.g., in murine and porcine animal models.

The United States Federal Drug Administration-approved truncated diphtheria toxin based human IL-2 fusion toxin, ONTAK (Denileukin diftitox, DAB389IL-2, Eisai Medical Research, Inc.) has been shown to deplete Tregs in both pre-clinical and clinical settings thereby facilitating improved cancer treatment (Morse et al., Blood 112:610-618 (2008); Mahnke et al., Int. J. Cancer 120:2723-33. (2007); Litzinger, et al., Blood 110:3192-3201 (2007); Gritzapis et al., Cancer Immunol Immunother. 61:397-407 (2012)). Natural killer (NK) cells are a very important component of the innate immune system as their functions include fighting pathogenic infections and cancer (Salagianni et al., J. Immunol. 186:3327-35 (2011)). While it is somewhat effective in depleting Tregs during cancer treatment, ONTAK also creates unwanted side effects as it has been shown to completely deplete NK cells for a prolonged period in a cynomolgus monkey model (Yamada et al., J. Immunol. 188: 6063-70 (2012)). However, this *E. coli* expressed, monovalent human IL-2 fusion toxin was unable to achieve optimal levels of Treg depletion (Morse et al., 2008; Barnett et al., Am. J Reprod. Immunol 54, 369 (2005); Telang et al., BMC. Cancer 11, 515 (2011); Attia et al., J Immunother. 28, 582 (2005); Yamada et al., J Immunol 188, 6063 (2012)) and its production has been discontinued since 2011. Endotoxin is another common concern when using *E. coli* expression system. The present study utilized a diphtheria toxin-resistant yeast *Pichia Pastoris* expression system (Liu et al., Protein Expr Purif 30, 262 (2003)), which offers greatly enhanced protein expression levels, purification and yield. Moreover, two human IL-2 domains were genetically linked to generate a bivalent fusion toxin with increased affinity for the IL-2 receptor. This bivalent human IL-2 fusion toxin showed significantly higher efficacy for human CD25$^+$ cells compared to the Ontak®-like monovalent isoform. Linking two human IL-2 domains in tandem may increase the fusion toxins' affinity for the human IL-2 receptor, subsequently facilitating a more efficient internalization, and causing a notable increase in potency. Producing the recombinant IL-2 fusion toxins in yeast rather than *E. coli* and generating a bivalent, more potent isoform augments the potential for clinical application of this reagent. In addition, this bivalent human IL-2 fusion toxin could serve as an ideal replacement for the clinically used and discontinued Ontak® for direct treatment of human CD25+ tumors such as cutaneous lymphoma. It may also prove valuable to investigators for depleting CD25+ cells found to contribute to post transplantation lymphoproliferative disorder (PTLD). Murine, porcine and human specific bivalent IL-2 fusion toxin reagents are available through our self-managed MGH-DF/HCC Recombinant Protein Expression and Purification Core facility for preclinical development and translational research.

IL-2 Immunotoxins

The truncated diphtheria toxin DT390 has been used to build recombinant immunotoxins (Woo et al., Protein Expr. Purif 25, 270-282 (2002); Kim et al., Protein Eng. Des. Sel. 20, 425-432 (2007); Wang et al., Bioconjug Chem. 22, 2014-2020 (2011)). DT390 lacks the cell-surface binding domain and consists of the catalytic and translocation domains of the diphtheria toxin. In this study each of the glycosylated and non-N-glycosylated porcine IL-2 proteins were linked to DT390 through genetic engineering yielding porcine IL-2 fusion toxins. The ability of these reagents to deplete target cells was assessed using an in vitro assay which monitored the inhibition of protein synthesis. Binding specificity and affinity to the target cells was analyzed by flow cytometry. In vivo target cell depletion was assessed using a porcine CD25+ B-cell lymphoma (LCL13271) NOD/SCID IL-2 receptor γ-/- (NSG) mouse model. In addition, depletion of Tregs in vivo was demonstrated in a porcine model.

IL-2

IL-2 binds to its cell surface receptor with notably strong affinity. The IL-2 receptor is a trimer composed of three subunits, α-β-γ. The α-subunit of this receptor, also known as CD25, is constitutively expressed on Tregs and has very high affinity for IL-2. There are species differences, including between human and porcine IL-2, which affect CD25 binding and subsequent target cell proliferation and differentiation (Zhang et al., Xenotransplantation. 13:423-32 (2006)), thus it is important to match the IL-2 sequence used to the species of the subject to be treated (i.e., use the human IL-2, or a variant thereof that binds the human IL-2 receptor, to treat human subjects).

The fusion proteins described herein comprise an IL-2 sequence, and preferably two IL-2 sequences, optionally with a short intervening linker therebetween to enable both of the sequences to retain binding function. A number of IL-2 sequences are known in the art and can be used in the constructs described herein. For example, all or part of the soluble human IL-2 sequence can be used, e.g., as set forth at GenBank Acc. Nos. NM_000586.3 (nucleic acid) and NP_000577.2 (amino acid); that amino acid sequence is as follows:

2001 September; 941:166-76; and Kelley et al., Proc. Natl. Acad. Sci. USA 85:3980-3984, 1988, all of which are incorporated by reference herein for their relevant teachings.

Additional sequences of IL-2, e.g., from other species, are known in the art; porcine IL-2 is described herein, and others are as follows; in general, portions of the sequences that do not include signal sequences can be used:

| IL-2 Sequences | |
|---|---|
| Species | GenBank Acc. No. |
| H. sapiens | NP_000577.2 |
| P. troglodytes | XP_003310513.1 |
| M. mulatta | NP_001040595.1 |
| C. lupus | NP_001003305.1 |
| B. taurus | NP_851340.1 |
| M. musculus | NP_032392.1 |
| R. norvegicus | NP_446288.1 |
| S. scrofa | NP_999026.1 |

Codon optimization is necessary to express DT390-based fusion toxins in the *Pichia pastoris* expression system (Woo et al., Protein Expr. Purif. 25, 270-282, 2002). A codon-optimized DT390 nucleotide sequence (Woo et al., 2002) was used for the DT390 domain. The DT390 has been modified to include an NH2 terminal alanine (A) and double mutations (dm) to prevent glycosylation in the eukaryotic expression system, *Pichia pastoris* (Woo et al., 2002, Liu et al., Protein Expr. Purif. 19, 304-311, 2000; Liu et al., Protein Expr. Purif. 30, 262-274, 2003). The codon-optimized glycosylated or non-N-glycosylated soluble porcine IL-2 nucleotide sequences described herein were used for the porcine IL-2 domain.

In some embodiments, the methods include altering the IL-2 sequence to remove an N-linked glycosylation site. The consensus sequence for N-linked glycosylation is Asn-Xaa-[Ser/Thr]; disruption can be achieved by mutation of the Asn, or the Ser/Thr. Referring to the porcine sequence, there is an N-linked glycosylation consensus site at N91; disruption of these sites can be achieved by mutating amino acids 91 or 93. A mutation at 91 can be to any amino acid other than N, and a mutation at 93 can be to any amino acid other than T or S, so long as the mutation substantially preserves the IL-2 Receptor (IL-2R) binding ability, i.e., the mutant retains at least 20% of the affinity of the wild type molecule, e.g., at least 30%, 40%, 50%, 60%, 70%, 80%, 90%, 95%, or more of the function of the wild type molecule, e.g., in an in vitro assay as known in the art or described herein. In some embodiments, the mutations include N91A.

In some embodiments, the mutation is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and

```
                                                              (SEQ ID NO: 1)
  1  myrmqllsci alslalvtns aptssstkkt qlqlehllld lqmilnginn yknpkltrml 61  tfkfympkka telkhlqcle eelkpleevl nlaqsknfhl rprdlisnin vivlelkgse 121  ttfmceyade tativeflnr witfcqsiis tlt
```

In some embodiments, only the mature protein, e.g., amino acids 7-150, 7-152, 20-150, 20-153, or 21-153, of SEQ ID NO:1 are used; amino acids 1-20 have been identified as a possible signal sequence. See, e.g., Williams et al., Protein Engineering 1(6):493-498, 1987; Foss, Ann NY Acad Sci.

vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III of US20110201052; pages 13-15 "Biochemistry" 2nd ED. Stryer ed (Stanford University); Henikoff et al., PNAS 1992 Vol 89 10915-10919; Lei et al., J Biol Chem 1995 May 19; 270(20):11882-6). In some embodiments, the protein includes a mutation at N91 to alanine or glycine. In some embodiments, the protein includes a mutation at N91 to a glutamine. In some embodiments, the protein includes a mutation at N91 to an aspartate or glutamate.

In some embodiments, instead of or in addition to a mutation at N91, the mutant includes a mutation at 93 to any amino acid other than serine or threonine, thereby disrupting the N-linked glycosylation consensus site. In some embodiments, the mutation at 93 is to alanine or glycine.

In some embodiments, the methods include introducing one or more additional mutations into the IL-2 sequence, e.g., the "IL-2 superkine" as described in Levin et al, 2012, Nature 484:529-533. Thus, in some embodiments, the sequence can be at least 80%, 85%, 90%, 95%, or 99% identical to at least 60%, 70%, 80%, 90%, or 100% of a human IL-2 sequence, e.g., SEQ ID NO:1; e.g., the sequence can include 1, 2, 3, 4, 5, 6, 7, 8, 9, 10, 11, 12, 13, 14, 15, 16, 17, 18, 19, or 20 mutations.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is typically at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

As noted above, the fusion proteins described herein includes at least two IL-2 sequences, preferably linked by a short intervening linker, e.g., 1-50 amino acids in length. The linker can have any composition so long as it (1) does not interfere with binding of the IL-2 to CD25; and (2) separates the two IL-2 to avoid interference with each other (e.g., steric or other interference). Preferably the linker does not encode another protein. In some embodiments, the linker is comprised of serine, alanine and glycine residues, e.g., is at least 50% alanine, glycine, or serine. In some embodiments, the linker comprises one or more $G_4S$ repeats, e.g., $G_4S$, $(G_4S)_2$, or $(G_4S)_3$.

The exemplary $(G_4S)_3$ linker used herein has been successfully used in following immunotoxins: anti-porcine CD3 immunotoxins (Wang et al, 2011, Bioconjug Chem. 22:2014-2020); anti-human CD3 immunotoxin (Woo et al. 2002, Protein Expr Purif. 25:270-282); anti-monkey CD3 immunotoxin (Kim et al., 2007, Protein Eng Des Sel. (PEDS). 20:425-432).

A linker as described herein may also be present between the IL-2 and the toxin.

Fusion Proteins

The recombinant IL-2 fusion proteins described herein include a non-IL-2 sequence fused to the N or C terminal of the IL-2. In some embodiments, the non-IL-2 sequence is a cytotoxic protein, e.g., Idarubicin; CRM9 (e.g., FN18-CRM9, Knechtle et al., Transplantation 1997; 63:1-6); or pokeweed antiviral protein. In some embodiments, the cytotoxic protein is a bacterial toxin, e.g., diphtheria toxin (DT) or portions or variants thereof, e.g., Met1-Thr387, e.g., as described in Aullo et al., EMBO J. 11(2):575-83 (1992); Abi-Habib et al., Blood. 104(7):2143-2148 (2004); Perentesis et al., Proc. Natl. Acad. Sci. USA 85:8386-8390 (1988); Zettlemeissl et al., Gene. 41(1):103-111 (1986); US 2009/0010966; US20090041797; U.S. Pat. No. 5,843,711; U.S. Pat. No. 7,585,942; U.S. Pat. No. 7,696,338; or US20080166375; or *Pseudomonas* exotoxin (PE), or portions or variants thereof, e.g., as described in U.S. Pat. Nos. 4,545,985; 4,892,827; 5,458,878; 7,314,632; Song et al., Protein Expression and Purification 44(1):52-57 (2005); Theuer et al., J. Biol. Chem. 267(24):16872-16877 (1992); Heimbrook et al., Proc Natl Acad Sci USA. 87(12):4697-4701 (1990); Debinski et al., Mol Cell Biol. 11(3):1751-1753 (1991); Chaudhary et al., Proc. Nadl. Acad. Sci. USA 87:308-312 (1990). In some embodiments, the cytotoxic protein is a plant toxin, e.g., a plant holotoxin (e.g., class II ribosome-inactivating proteins such as ricin (e.g., deglycosylated ricin A chain (dgA)), abrin, mistletoe lectin, or modeccin) or hemitoxin (class I ribosome-inactivating proteins, e.g., PAP, saporin, bryodin 1, bouganin, or gelonin), or fragments or variants thereof that retain cytotoxic activity. See, e.g., Neville et al., J Contr Rel 1993; 24:133-141; Vallera, Blood 1994; 83:309-317; Vitetta et al., Immunology Today 1993; 14:252-259; Kreitman et al., AAPS Journal. 2006; 8(3):E532-E551). Suitable sequences are known in the art.

Peptide Tags

In some embodiments, the proteins or fusion proteins further include a peptide tag useful for purification. In some embodiments, the tag comprises histidines, e.g., two or more, e.g., three, four, five or six histidine residues at the C-terminus (i.e., as shown at positions 403-420 of SEQ ID NOs:7 or 6, FIG. 2), and purification is achieved by binding to a nickel or cobalt column. In some embodiments, the tag comprises glutathione-S-transferase (GST) and recovery is by affinity to substrate glutathione bound to a column, e.g., glutathione sepharose. In some embodiments, the tag comprises a FLAG peptide (e.g., N-DYKDDDDK-C(SEQ ID NO:8) or a variant thereof) and protein is recovered with specific antibody to the peptide. In some embodiments, the tag comprises an epitope derived from the Influenza protein haemagglutinin (HA) (e.g., N-YPYDVP-C(SEQ ID NO:9)) and protein is recovered using an anti-HA antibody that binds the epitope. In some embodiments, the tag comprises an epitope derived from the human proto-oncoprotein myc (e.g., N-ILKKATAYIL-C(SEQ ID NO:10), or N-EQKLI-SEEDL-C(SEQ ID NO:11)), and recovery is performed with an anti-myc antibody.

In some embodiments, the protein further comprises a proteolytic cleavage site between the purification tag and the CTLA-4 sequence, and after purification the protein is treated with the protease to remove the purification tag. Examples include the PreScission protease, thrombin, and factor Xa. Enterokinase sites that enable tag cleavage without leaving behind extra amino acids are preferred. In some embodiments, an exopeptidase is used to remove N-terminal His-tags (e.g., Qiagen TAGZyme). See, e.g., *The Recombinant Protein Handbook, Protein Amplification and Simple Purification*, Amersham Biosciences, available online at 130.15.90.245/methods/hand-books%20and%20manuals/the%20recombinant%20protein%20handbook.pdf.

Codon Optimization

In addition, the nucleic acid sequences used in the present methods are preferably codon-optimized for expression in a selected expression system, e.g., in *Pichia pastoris* (See, e.g., Woo et al., Protein Expr. Purif. 25, 270-282, 2002). In order to optimize expression in non-mammalian cells, codon optimization specific for a selected host organism can be used. For example, in embodiments where *P. pastoris* is used as a host organism, the following Table 1 (source: kazusa.or.jp) can be used to select codons:

TABLE 1

Codon Optimization Table for *Pichia Pastoris*

| triplet | UUU | UCU | UAU | UGU |
|---|---|---|---|---|
| amino acid | F | S | Y | C |
| fraction | 0.54 | 0.29 | 0.47 | 0.64 |
| frequency: per 1000 | 24.1 | 24.4 | 16.0 | 7.7 |
| (number) | (1963) | (1983) | (1300) | (626) |
| triplet | UUC | UCC | UAC | UGC |
| amino acid | F | S | Y | C |
| fraction | 0.46 | 0.20 | 0.53 | 0.36 |
| frequency: per 1000 | 20.6 | 16.5 | 18.1 | 4.4 |
| (number) | (1675) | (1344) | (1473) | (356) |
| triplet | UUA | UCA | UAA | UGA |
| amino acid | L | S | * | * |
| fraction | 0.16 | 0.18 | 0.51 | 0.20 |
| frequency: per 1000 | 15.6 | 15.2 | 0.8 | 0.3 |
| (number) | (1265) | (1234) | (69) | (27) |
| triplet | UUG | UCG | UAG | UGG |
| amino acid | L | S | * | W |
| fraction | 0.33 | 0.09 | 0.29 | 1.00 |
| frequency: per 1000 | 31.5 | 7.4 | 0.5 | 10.3 |
| (number) | (2562) | (598) | (40) | (834) |
| triplet | CUU | CCU | CAU | CGU |
| amino acid | L | P | H | R |
| fraction | 0.16 | 0.35 | 0.57 | 0.17 |
| frequency: per 1000 | 15.9 | 15.8 | 11.8 | 6.9 |
| (number) | (1289) | (1282) | (960) | (564) |
| triplet | CUC | CCC | CAC | CGC |
| amino acid | L | P | H | R |
| fraction | 0.08 | 0.15 | 0.43 | 0.05 |
| frequency: per 1000 | 7.6 | 6.8 | 9.1 | 2.2 |
| (number) | (620) | (553) | (737) | (175) |
| triplet | CUA | CCA | CAA | CGA |
| amino acid | L | P | Q | R |
| fraction | 0.11 | 0.42 | 0.61 | 0.10 |
| frequency: per 1000 | 10.7 | 18.9 | 25.4 | 4.2 |
| (number) | (873) | (1540) | (2069) | (340) |
| triplet | CUG | CCG | CAG | CGG |
| amino acid | L | P | Q | R |
| fraction | 0.16 | 0.09 | 0.39 | 0.05 |
| frequency: per 1000 | 14.9 | 3.9 | 16.3 | 1.9 |
| (number) | (1215) | (320) | (1323) | (158) |
| triplet | AUU | ACU | AAU | AGU |
| amino acid | I | T | N | S |
| fraction | 0.50 | 0.40 | 0.48 | 0.15 |
| frequency: per 1000 | 31.1 | 22.4 | 25.1 | 12.5 |
| (number) | (2532) | (1820) | (2038) | (1020) |
| triplet | AUC | ACC | AAC | AGC |
| amino acid | I | T | N | S |
| fraction | 0.31 | 0.26 | 0.52 | 0.09 |
| frequency: per 1000 | 19.4 | 14.5 | 26.7 | 7.6 |
| (number) | (1580) | (1175) | (2168) | (621) |
| triplet | AUA | ACA | AAA | AGA |
| amino acid | I | T | K | R |
| fraction | 0.18 | 0.24 | 0.47 | 0.48 |
| frequency: per 1000 | 11.1 | 13.8 | 29.9 | 20.1 |
| (number) | (906) | (1118) | (2433) | (1634) |

TABLE 1-continued

Codon Optimization Table for *Pichia Pastoris*

| triplet | AUG | ACG | AAG | AGG |
|---|---|---|---|---|
| amino acid | M | T | K | R |
| fraction | 1.00 | 0.11 | 0.53 | 0.16 |
| frequency: per 1000 | 18.7 | 6.0 | 33.8 | 6.6 |
| (number) | (1517) | (491) | (2748) | (539) |
| triplet | GUU | GCU | GAU | GGU |
| amino acid | V | A | D | G |
| fraction | 0.42 | 0.45 | 0.58 | 0.44 |
| frequency: per 1000 | 26.9 | 28.9 | 35.7 | 25.5 |
| (number) | (2188) | (2351) | (2899) | (2075) |
| triplet | GUC | GCC | GAC | GGC |
| amino acid | V | A | D | G |
| fraction | 0.23 | 0.26 | 0.42 | 0.14 |
| frequency: per 1000 | 14.9 | 16.6 | 25.9 | 8.1 |
| (number) | (1210) | (1348) | (2103) | (655) |
| triplet | GUA | GCA | GAA | GGA |
| amino acid | V | A | E | G |
| fraction | 0.15 | 0.23 | 0.56 | 0.33 |
| frequency: per 1000 | 9.9 | 15.1 | 37.4 | 19.1 |
| (number) | (804) | (1228) | (3043) | (1550) |
| triplet | GUG | GCG | GAG | GGG |
| amino acid | V | A | E | G |
| fraction | 0.19 | 0.06 | 0.44 | 0.10 |
| frequency: per 1000 | 12.3 | 3.9 | 29.0 | 5.8 |
| (number) | (998) | (314) | (2360) | (468) |

For example an exemplary sequence of a codon-optimized human IL-2 cDNA (without signal peptide) is as follows:

```
                                          (SEQ ID NO: 2)
GCT CCA ACT TCT TCT TCT ACT AAG AAG ACT

CAA TTG CAA TTG GAG CAC TTG TTG TTG GAC

TTG CAA ATG ATT TTG AAC GGT ATT AAC AAC

TAC AAG AAC CCA AAG TTG ACT AGA ATG TTG

ACT TTC AAG TTC TAC ATG CCA AAG AAG GCT

ACT GAG TTG AAG CAC TTG CAA TGT TTG GAG

GAG GAA TTG AAG CCA TTG GAG GAA GTT TTG

AAC TTG GCT CAA TCT AAG AAC TTC CAC TTG

AGA CCA AGA GAC TTG ATT TCT AAC ATT AAC

GTT ATT GTT TTG GAG TTG AAG GGT TCT GAG

ACT ACT TTC ATG TGT GAG TAC GCT GAC GAG

ACT GCT ACT ATT GTT GAG TTC TTG AAC AGA

TGG ATT ACT TTC TGT CAA TCT ATT ATC TCT

ACT TTG ACT
```

The above sequence codes for the following human IL-2 amino acid sequence (without signal peptide):

```
                                          (SEQ ID NO: 3)
APTSSSTKKTQLQLEHLLLDLQMILNGINNYKNPKLTRMLI FKFYMPKK

ATELKHLQCLEEELKPLEEVLNLAQSKNFHLRPRDLISNINIVLELKG

SETTFMCEYADETATIVEFLNRWITFCQSIISTLT
```

The following is an exemplary codon-optimized mouse IL-2 DNA sequence (without signal peptide):

```
                                          (SEQ ID NO: 4)
GCT CCA ACT TCT TCC TCT ACT TCT TCC TCT

ACT GCT GAG GCT CAA CAA CAA CAA CAA CAA

CAA CAA CAA CAA CAA CAA CAC TTG GAG CAA

TTG TTG ATG GAC TTG CAA GAG TTG TTG TCT

AGA ATG GAG AAC TAC AGA AAC TTG AAG TTG

CCA AGA ATG TTG ACT TTC AAG TTC TAC TTG

CCA AAG CAA GCT ACT GAG TTG AAG GAC TTG

CAA TGT TTG GAG GAC GAG TTG GGT CCA TTG

AGA CAC GTT TTG GAC TTG ACT CAA TCT AAG

TCT TTC CAA TTG GAG GAC GCT GAG AAC TTC

ATT TCT AAC ATT AGA GTT ACT GTT GTC AAG

TTG AAG GGT TCT GAC AAC ACT TTC GAG TGT

CAA TTC GAC GAC GAG TCT GCT ACT GTT GTC

GAC TTC TTG AGA AGA TGG ATT GCT TTC TGT

CAA TCT ATT ATC TCT ACT TCT CCA CAA
```

This encodes the following mouse IL-2 amino acid sequence (without signal peptide)

```
                                          (SEQ ID NO: 5)
APTSSSTSSS TAEAQQQQQQ QQQQQQHLEQ LLMDLQELLS

RMENYRNLKL PRMLTFKFYL PKQATELKDL QCLEDELGPL

RHVLDLTQSK SFQLEDAENF ISNIRVTVVK LKGSDNTFEC

QFDDESATVV DFLRRWIAFC QSIISTSPQ
```

Protein Production Methods

The methods for producing bivalent IL-2 fusion toxins described herein can be performed using protein production methods known in the art. For example, for scaled-up production, fermentation expression can be used.

Furthermore, although in a preferred embodiment the present methods use *P. pastoris* as a host organism, e.g., wild-type, X33, GS115 (his4), KM71, MC100-3, SMD1163, SMD1165, or SMD1168 strain, others can also be used. For example, in species in which the IL-2 sequence includes an N-glycosylation site, mutant strains of *P. pastoris* that have been altered to express proteins with more human-like glycosylation can be used (see, e.g., Bollok et al., Recent Patents on Biotechnology 2009, 3, 192-201; U.S. Pat. Nos. 7,029,872; 6,803,225; 7,449,308; 7,252,933; 7,326,681; 7,507,573; and references described therein); in such methods a mutated IL-2 sequence can be used. Other yeast, e.g., other methylotropic yeast, e.g., yeast of the genera *Candida*, *Hansenula* or *Torulopsis*, can also be used. Generally speaking, most *P. pastoris* expression strains are derivatives of NRRL-Y 11430 (Northern Regional Research Laboratories, Peoria, Ill.).

Vectors suitable for use in the present methods are known in the art, and generally include a promoter, e.g., an AOX1, a constitutive *P. Pastoris* promoter derived from the *P. pastoris* glyceraldehyde-3-phosphate dehydrogenase gene (GAP) promoter, typically followed immediately with a DNA sequence that encodes a secretion signal, e.g., the *S. cerevisiae* α factor prepro signal sequence, or the signal sequence derived from the *P. pastoris* acid phosphatase gene (PHO1).

The vectors can also include one or more yeast selectable markers that can be used to identify and/or select those cells that contain the vector can be used. Such markers can include drug resistance markers and pathways for synthesis of essential cellular components, e.g., nutrients. Drug resistance markers that can be used in yeast include chloramphenicol, kanamycin, methotrexate, G418 (geneticin), Zeocin, and the like. Markers in synthesis pathways can be used with available yeast strains having auxotrophic mutations in the corresponding gene; examples include the pathways for synthesizing leucine (LEU2), tryptophan (TRP1 and TRP2), proline (PROD, uracil (URA3, URA5, URA6), histidine (HIS3), lysine (LYS2), adenine (ADEJ or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al, J-Biol. Chem. 272:30061-30066 (1997)). A number of suitable integration sites include those enumerated in U.S. Pat. No. 7,479,389 and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135). Examples of insertion sites include, but are not limited to, *Pichia* ADE genes; *Pichia* TRP (including TRP J through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al, Gene 263:159-169 (2001) and U.S. Pat. No. 4,818,700, the HIS3 and TRP1 genes have been described in Cosano et al., Yeast 14:861-867 (1998), HIS4 has been described in GenBank Accession No. X5 180. See e.g., WO2011046855; Cregg, J. M. (2007) *Methods in Molecular Biology: Pichia Protocols*, Second Edition, Volume 389, Humana Press, Totowa, N.J.; Romanos et al., Yeast 8:423-488 (1992); Ilgen, et al., (2004) Chapter 7: *Pichia pastoris*. In: *Production of recombinant proteins: microbial and eukaryotic expression systems*. Gellissen, G. (ed.) Wiley-VCH Verlag, Weinheim, Germany, pp. 143-162; Cereghino and Cregg, FEMS Microbiology Reviews 24:45-66 (2000); and Cregg, "The *Pichia* System", available online at pichia.com/pichia_system.pdf. Exemplary vectors include pPIC3K, pPIC9K, pAO815 and the pPICZ vector series.

Purification

Methods known in the art can be used for nickel-based purification of the bivalent IL-2 fusion proteins. For example, although the present examples use a hexahistidine tag to facilitate purification, this may not be preferred for a pharmaceutical intended for in vivo use. Thus, other methods, including ammonium sulfate precipitation, reversed phase chromatography, hydrophobic interaction chromatography (HIC), size exclusion chromatography, ion exchange chromatography, affinity chromatography, metal binding, immunoaffinity chromatography, HPLC, or purification tags (e.g., as described above) may be used to directly capture the purified proteins. See, e.g., Deutscher, M. P. (1990) Guide to Protein Purification. In: *Methods in Enzymology* (J. N. Abelson and M. I. Simon, eds.) Academic Press, San Diego, Calif.; and *The Recombinant Protein Handbook, Protein Amplification and Simple Purification*, Amersham Biosciences, available online at 130.15.90.245/methods/handbooks%20and%20manuals/the%20recombinant%20protein%20handbook.pdf.

After purification, the protein can optionally be concentrated, e.g., by lyophilization or ultrafiltration.

Methods of Use

While Tregs function advantageously in development of transplantation tolerance and prevention of autoimmunity, their down regulation of immune responses may impede the body's ability to clear tumorigenic cell populations. Tumor progression induces proliferation of two T cell populations: those that target cancer cells; and those that down-regulate the targeting population, allowing the cancer to progress. The immune modulating cell populations are a major obstruction to treatments designed to activate and expand cells capable of targeting tumor cells. Treg suppress immune responses to tumors, therefore, methods that target and deplete this cell population in vivo could prove to be useful in improving cancer immunotherapy.

The bivalent IL-2 fusion toxins described herein can be used in the treatment or study of certain disorders, e.g., induction of transplant tolerance; autoimmune diseases; as well as cancer. For example, this fusion toxin can be used to target tumor cells that express CD25 on the surface, like B-cell neoplasms (e.g., CD15+ B-cell lymphoma), some acute nonlymphocytic leukemias, neuroblastomas, tumor infiltrating lymphocytes, and cutaneous T cell lymphoma. Methods known in the art can be used to identify subjects who have cancers that express CD25. In a preferred embodiment, the methods are used to treat subjects who have cutaneous T cell lymphoma. In some embodiments, the methods include administering one or more additional therapeutic agents, e.g., one or more of Vorinostat, Bexarotene and Romidepsin.

In another embodiment, the fusion proteins described herein can also be used to target and deplete Treg cells that express CD25, which are known to suppress the immune response to cancer (Menetrier-Caux et al., Targ Oncol (2012)7:15-28). Generally, the methods include administering a therapeutically effective amount of the IL-2 fusion toxins as described herein, alone or in combination with another active agent, to a subject who is in need of, or who has been determined to be in need of, such treatment. In some embodiments, the methods also include administering one or more immunotherapies for cancer, e.g., one or more therapies that promote anti-cancer immunity, including administering one or more of: dendritic cells or peptides with adjuvant, immune checkpoint inhibitors, DNA-based vaccines, cytokines (e.g., IL-2), cyclophosphamide, agonists of OX40 (OX40; CD134), anti-interleukin-2R immunotoxins, and/or antibodies such as anti-CD137, anti-PD1, or anti-CTLA-4; see, e.g., Krüger et al., Histol Histopathol. 2007 June; 22(6):687-96; Eggermont et al., Semin Oncol. 2010 October; 37(5):455-9; Klinke D J 2nd, Mol Cancer. 2010 Sep. 15; 9:242; Alexandrescu et al., J Immunother. 2010 July-August; 33(6):570-90; Moschella et al., Ann N Y Acad Sci. 2010 April; 1194:169-78; Ganesan and Bakhshi, Natl Med J India. 2010 January-February; 23(1):21-7; Golovina and Vonderheide, Cancer J. 2010 July-August; 16(4):342-7; Hodi et al., The New England journal of medicine 2010 363:711-723; Pentcheva-Hoang et al., Immunological Reviews 2009 229:67-87; Brahmer et al., Journal of Clinical Oncology 2010 28:3167-3175; Lynch et al., Journal of Clinical Oncology 2012 30(17):2046; Weber, Current Opinion in Oncology 2011 23:163-169; Weber, Seminars in Oncology 2010 37:430-439; Topalian et al., 2012. The New England Journal of Medicine 366:2443-2454; and Higano et al., Cancer 2009 115:3670-3679.

In some embodiments, the methods include administering a composition comprising tumor-pulsed dendritic cells, e.g., as described in WO2009/114547 and references cited therein. Additional examples of immunotherapies include virus-based anti-cancer vaccines (e.g., adenovirus), formulations of Toll-like Receptor or RIG-I-like receptor ligands, Adoptive T cell therapy or other cell types. In some embodiments the immunotherapy is selected from the group consisting of BiovaxID (an autologous vaccine containing tumor-specific idiotype proteins from individual patient's lymphoma cells conjugated to keyhole limpet hemocyanin (KLH)); Provenge sipuleucel-T (an FDA-approved example of the use of autologous dendritic cells); Yervoy (a mAb against CTLA-4 (CD152), approved in 2011 for metastatic melanoma); tremelimumab (formerly ticilimumab, an anti-CTLA-4 mAb); IMA901 (a vaccine containing 10 tumor-associated peptides (TUMAPs)), alone or in combination with Sutent (a small molecule VEGF receptor tyrosine kinase inhibitor); GV1001 (a peptide vaccine with the sequence of human telomerase reverse transcriptase (hTERT), from Kael-Gemvax); Lucanix belagenpumatecel-L (four NSCLC cell lines carrying antisense oligonucleotides against transforming growth factor beta 2 (TGFB2)); Stimuvax (a liposomal vaccine containing a synthetic 25-amino acid peptide sequence from mucin 1 (MUC1; CD227)); Allovectin velimogene aliplasmid (a DNA plasmid encoding major histocompatibility complex (MHC) class I B7 (HLA-B7) complexed with lipid); BMS-936558 (ONO-4538) (a human mAb against PD-1); BMS-936559 (formerly MDX-1105) (a human mAb against PD-L1); Zelboraf (vemurafenib, an oral small molecule inhibitor of the oncogenic BRAF V600E mutation); Votrient (pazopanib, a small molecule VEGF receptor tyrosine kinase inhibitor); ISF35 or Lucatumumab (HCD122) (mAbs against CD40); GVAX (an allogeneic cancer vaccine engineered to secrete granulocyte macrophage-colony stimulating factor (GM-CSF)). See, e.g., Flanagan, "Immune Springboard," Biocentury, Jun. 18, 2012 A5-A10 (2012), available at biocentury.com. In some embodiments, the immunotherapy comprises administration of an agent that effects CTLA4 blockade (e.g., Ipilumumab BMS), PD1-blockade (e.g., BMS-936558, BMS; CT-011, Curetech; MK-3475, Merck), CD137 activation (e.g., BMS-663513, BMS), PD-L1 blockade (e.g., BMS-936559, BMS), CD40 activation (e.g., CP-870893, Pfizer) and autologous dendritic cells (e.g., Provenge).

An additional application of these proteins is use as a research tool, e.g., to study the role of Treg in immune regulation and transplant rejection. Experimental and clinical data demonstrated that Treg, characterized as CD4+CD25+Foxp3+, have significantly reduced suppression function in animal models and patients with autoimmune diseases such as rheumatoid arthritis, multiple sclerosis and type I diabetes (Viglietta et al., J Exp Med 199, 971 (2004); Lindley et al., Diabetes 54, 92 (2005); Ehrenstein et al., J Exp Med 200, 277 (2004); Sakaguchi et al., Cell 133, 775 (2008)). A reagent capable of depleting Treg in vivo could offer a useful tool for researchers studying autoimmune diseases in animal models.

Treg are also extensively studied in transplantation in an effort to understand the immunological mechanisms behind tolerance and rejection of allogeneic and xenogeneic organs. Increased levels of CD4+CD25hiFoxp3+ Treg have been detected in donor kidneys of tolerant recipients in experimental animal models and clinical patients (Miyajima et al., 2011). It is unclear, however, what role Treg play in the induction and maintenance of tolerance of these allografts. Efficient targeting and depletion of Treg in vivo may aid in determining the mechanisms of how Treg facilitate the initiation of and subsequently sustain tolerance to transplanted organs.

Thus the methods can include administering the fusion proteins or nucleic acids encoding the fusion proteins to an animal, e.g., an animal model of an autoimmune disease or of transplant rejection, and evaluating one or more symptoms or parameters of the disease in the animal.

Gene Therapy

The nucleic acids described herein can be incorporated into a gene construct to be used as a part of a gene therapy protocol. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid described herein in the tissue of a subject, e.g., in a tumor tissue. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21): 1867-74 (2000).

In clinical settings, the gene delivery systems for the therapeutic gene can be introduced into a subject by any of a number of methods, each of which is known in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded.

EXAMPLES

The invention is further described in the following examples, which do not limit the scope of the invention described in the claims.

Example 1

Porcine IL-2 Fusion Toxins

Example 1 describes the generation and testing of a porcine IL-2 fusion toxin.

Materials and Methods

The following materials and methods were used in Example 1 set forth below.

Plasmid Construction. As shown in FIG. 1, porcine IL-2 fusion toxins were built to contain two moieties using the codon-optimized nucleotide sequences; the first is DT390 (Woo et al., Protein Expr. Purif. 25, 270-282 (2002)) and the second is porcine IL-2. A strategy previously employed to construct A-dm-DT390biscFv (2-6-15) (Wang et al., Bioconjug Chem. 22, 2014-2020 (2011)) was applied to build these porcine IL-2 fusion toxins. The biscFv (2-6-15) moiety was replaced with the codon-optimized glycosylated or non-N-glycosylated porcine IL-2 (FIG. 2). A linker made up of three tandem chains each containing four glycine residues and a serine $(G_4S)_3$ was used to connect two porcine IL-2 proteins for building the bi-porcine IL-2 fusion toxins. Six histidines (6× His tag) were added to the C-terminus of each construct to facilitate later purification. The codon-optimized glycosylated porcine IL-2 DNA was synthesized by GenScript (Piscataway, N.J.) and the codon-optimized non-N-Glycosylated porcine IL-2 DNA was generated by site-directed mutagenesis with sense PCR primer pIL2-N91A For and anti-sense PCR primer pIL2-N91A Rev (Agilent technologies). To construct DT390-pIL-2-Gly or DT390-pIL-2-Non-N-Gly, the codon-optimized glycosylated or non-N-glycosylated porcine IL-2 DNA (FIG. 2) was amplified using PCR primers pIL2-X1 carrying XhoI and NcoI site+pIL2-E1 carrying an EcoRI site then cloned into pwPICZalpha (Peraino et al., Protein Expr Purif. 82, 270-278 (2012)) between XhoI and EcoRI sites for sequencing confirmation. The insert was then cut out with NcoI+EcoRI and cloned into pwPICZalpha-DT390 (Wang et al., Bioconjug Chem. 22, 2014-2020 (2011)) between NcoI and EcoRI sites yielding the final construct DT390-pIL-2-Gly or DT390-pIL-2-Non-N-Gly in pwPICZalpha. To construct DT390-bi-pIL-2-Gly or DT390-bi-pIL-2-Non-N-Gly, the first porcine IL-2-Gly or porcine IL-2-Non-N-Gly was amplified using PCR primers pIL2-X1 carrying XhoI and NcoI sites+pIL2-Bam1 carrying BamHI and EcoRI sites then cloned into pwPICZalpha between XhoI and EcoRI sites for sequencing confirmation. The insert was subsequently cut out with NcoI+BamHI as insert I. The second porcine IL-2-Gly or porcine IL-2-Non-N-Gly was PCR amplified using pIL2-Bam2 carrying XhoI and BamHI sites+pIL-2-E1 carrying an EcoRI site then cloned into pwPICZalpha between XhoI and EcoRI sites for sequencing confirmation. The insert was then cut out with BamHI+EcoRI as insert II. The insert I carrying NcoI and BamHI sites+insert II carrying BamHI and EcoRI sites (NcoI-pIL-2-BamHI/BamHI-pIL-2-EcoRI) were together cloned into pwPICZalpha-DT390 between NcoI and EcoRI yielding the final construct DT390-bi-pIL-2-Gly or DT390-bi-pIL-2-Non-N-Gly in pwPICZalpha. All PCR primers that were used are listed in Table 2.

TABLE 2

PCR primers used in this study

| PRIMER | SEQUENCE | SEQ ID NO: |
|---|---|---|
| pIl2-X1 | 5' CCG CTC GAG CCA TGG GCT CCA ACT TCT TCC TCT ACT 3' | 12 |
| pIL2-Bam1 | 5' CCG GAA TTC GGA TCC ACC ACC ACC AGA ACC ACC ACC ACC AGT CAA AGT AGA GTA AAT AGA TTG 3' | 13 |
| pIL2-Bam2 | 5' CCG CTC GAG GGA TCC GGT GGT GGT GGT TCT GCT CCA ACT TCT TCC TCT ACT 3' | 14 |
| pIl2-E1 | 5' CCG GAA TTC TTA GTG GTG GTG GTG GTG GTG AGT CAA AGT AGA GTA AAT AGA TTG 3' | 15 |
| pIL2-N91A For | 5' AAG GAG TCT ATG AAC AAC ATT GCT GTT ACT GTT TTG GAG TTG AAG 3' | 16 |
| pIL2-N91A Rev | 5' CTT CAA CTC CAA AAC AGT AAC AGC AAT GTT GTT CAT AGA CTC CTT 3' | 17 |

Protein expression and purification in *Pichia pastoris* were performed as previously described with the following modifications (Wang et al., (2011) supra; Peraino et al. 'Protein Expr Purif. 82, 270-278 (2012)). A Ni-Sepharose fast flow resin (GE healthcare) was used for the purification. Porcine IL-2 fusion toxins were eluted using 40 mM imidazole. Western blot analysis, FACS analysis, FACS competition/blocking analysis and $K_D$ determination were all performed as previously described (Peraino et al., Protein Expr Purif. 82, 270-278 (2012)) using LCL13271 cells (Cho et al., Blood 110, 3996-4004 (2007)).

Protein Synthesis Inhibition. Porcine IL-2 fusion toxins (DT390-pIL-2-Gly, DT390-pIL-2-Non-N-Gly, DT390-bi-pIL-2-Gly and DT390-bi-pIL-2-Non-N-Gly) were diluted in 1× leucine-free RPMI 1640 media supplemented with 12% fetal bovine serum, 10 mM hepes (N-2-hydroxyethylpiperazine-N-2-ethanesulfonic acid), 1× nonessential amino acids, 1 mM sodium pyruvate, 2 mM glutamine, and $2.5\times10^{-5}$M 2-mercaptoethanol. Target $CD25^+$ LCL13271 cells were washed twice by centrifugation at 1000 rpm, 20° C. for 5 minutes in 50 mL of leucine-free RPMI 1640 media described above. Cells were then diluted to $5.0\times10^5$ cells/mL in leucine-free RPMI 1640 media and 100 μL of cells was added to each well (three wells per fusion toxin dilution) in a 96-well flat bottom plate (Corning) to achieve a final cell concentration of $5.0\times10^4$ cells/well. Ten microliters of fusion toxin dilutions were added to each well containing LCL13271 cells. Six wells contained only cells, three of these remained without fusion toxin and served as the negative control and the other three were reserved for the positive control which was added later. Plates were then incubated at 37° C. with 5% $CO_2$ for 18 hours. Cycloheximide (Sigma) was diluted 1:8 and 10 μL of this dilution was added to each of three wells containing cells only then incubated for the last 15 min of the 18 hr. incubation. Cells were pulsed with 1 μCi/well of $^3$H-Leucine then incubated at 37° C. with 5% $CO_2$ for 1 hour. Cells were harvested onto filter mats (Perkin-Elmer) using a cell harvester (Harvester 96® Mach II). The filters were allowed to dry at room temperature overnight then Cpm was measured on a microbeta counter.

In Vivo Functional Analysis. A breeding pair of NSG mice were purchased from Jackson laboratories and bred in our rodent barrier facilities for use in this study.

All NSG mice were given injections of 10 million porcine $CD25^+$ tumor cells (LCL13271) IV via the tail vein. Six mice were injected with 50 μg/kg of porcine IL-2 fusion toxin (Bi-Gly version) on day 0 and the drug was administered IP twice a day for 4 days and then once a day every 3 days for 9 days. Controls (n=13) received the tumor cells without the fusion toxin and an additional two mice were given the tumor cells and treated with the drug vehicle (PBS). Injected animals were then observed daily for signs and symptoms of illness and scored biweekly based on several parameters (Schenk et al manuscript in preparation): respiratory effort (0-3), weight loss/gain (0-2), fur integrity (0-3), provoked (0-3) and non-provoked activity (0-1), posture (0-3), abdominal distention (0-3), abdominal palpation (0-3) and body condition score (0-3). The highest score in each category represents the worst possible condition for that parameter. The highest possible score on the scoring system is a 24. Mice were humanely euthanized and necropsy was performed after a score of 12 or higher was achieved or when an animal lost more than 15% of its pre-injection body weight.

Example 1.1

Expression and Purification of Porcine IL-2 Fusion Toxins

Four versions of the porcine IL-2 fusion toxin were constructed in an effort to develop the most effective reagent: 1) Gly=monovalent glycosylated porcine IL-2 (DT390-pIL-2-Gly); 2) NonGly=monovalent non-N-glycosylated porcine IL-2 (DT390-pIL-2-Non-N-Gly); 3) Bi-Gly=glycosylated bivalent porcine IL-2 (DT390-bi-pIL-2-Gly) and 4) Bi-NonGly=non-N-glycosylated bivalent porcine IL-2 (DT390-bi-pIL-2-Non-N-Gly). The bivalent isoforms were joined by a $(G_4S)_3$ linker. FIG. 1 shows a schematic representation of the fusion toxins.

Each porcine IL-2 fusion toxin contains two domains; 1) the truncated diphtheria toxin DT390 and 2) porcine IL-2. The codon-optimized porcine IL-2 DNA (FIG. 2) was cloned into the C-terminus of DT390 between NcoI and EcoRI in the DT390-containing yeast *Pichia pastoris* expression vector pwPICZalpha-A-dmDT390 (Wang et al. (2011), supra). To facilitate the later purification we added a 6×His tag to the C-terminus of each fusion toxin.

The porcine IL-2 fusion toxins were expressed in yeast *Pichia pastoris* using shaker flasks as described in Experimental Procedures. Western blot analysis confirmed the expression using mouse anti-6×His monoclonal antibody (4A12E4, Invitrogen, data not shown). The secreted porcine IL-2 fusion toxin in the supernatant was purified using Ni-Sepharose fast flow resin (FIG. 3). The final purification yield was ~30 mg per liter of the original harvested supernatant for the monovalent porcine IL-2 fusion toxins and ~15 mg per liter for the bivalent porcine IL-2 fusion toxins.

Example 1.2

Figure 4:
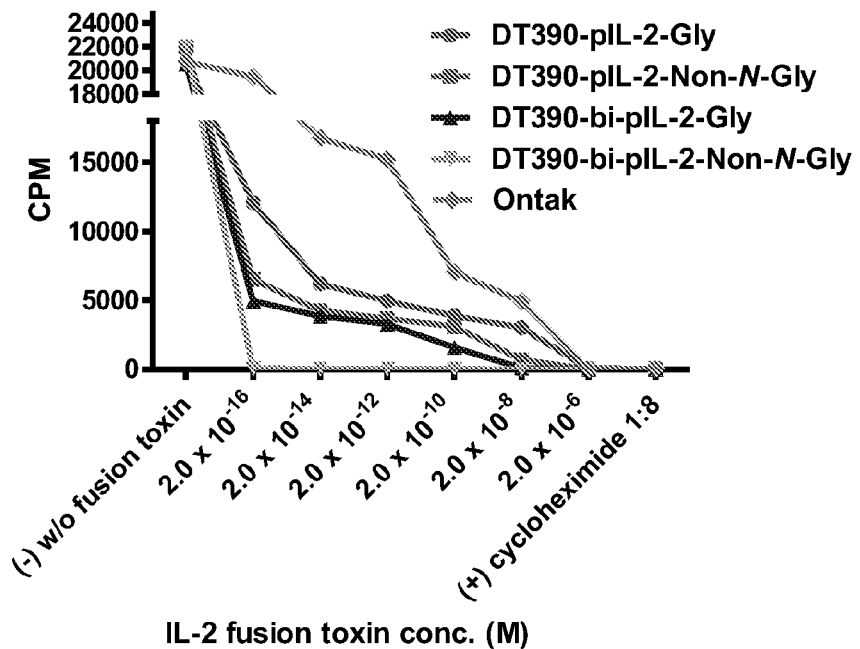
FIG. 4. In vitro Protein Synthesis Inhibition Analysis of the Four Porcine IL-2 Fusion Toxins as well as Ontak® using Porcine CD25+ B-cell Lymphoma Cell Line (LCL13271 Cells): 1) DT390-pIL-2-Gly; 2) DT390-pIL-2-Non-N-Gly; 3) DT390-bi-pIL-2-Gly; 4) DT390-bi-pIL-2-Non-N-Gly. 5) Ontak®. Y-axis: cpm value by incorporating the tritium-labeled leucine. X-axis: plated IL-2 fusion toxin concentration. Cyclohexmide (1:8) was used as a positive control. The negative control contained cells only without fusion toxin. Data are representative of multiple assays.
Figure 5A:
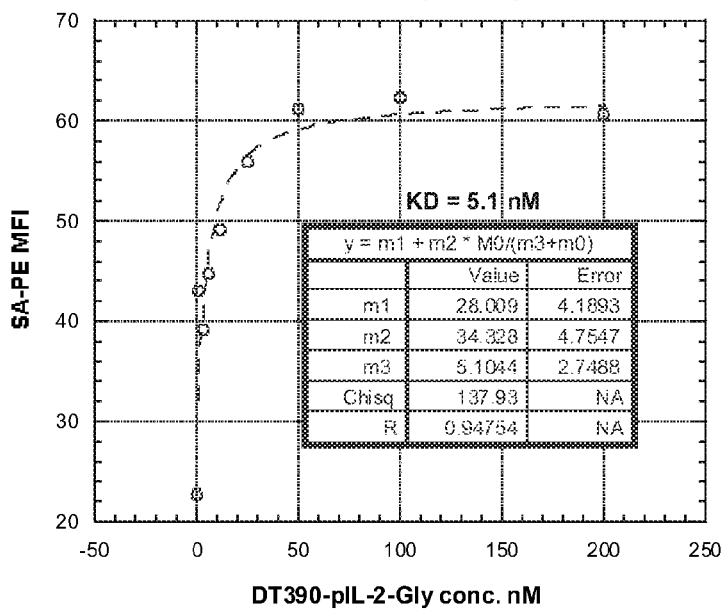
FIG. 5. $K_D$ Determination Using Flow Cytometry and Nonlinear Least Squares Fit. MFI was plotted over a wide range of concentrations of biotinylated A) DT390-pIL-2-Gly, B) DT390-pIL-2-Non-N-Gly, C) DT390-bi-pIL-2-Gly and D) DT390-bi-pIL-2-Non-N-Gly. The accompanying least-squares fits and parameters are shown based on the hyperbolic equation y=m1+m2*m0/(m3+m0) where y=MFI at the given biotinylated porcine IL-2 fusion toxin concentration, m0=biotinylated porcine IL-2 fusion toxin concentration, m1=MFI of zero biotinylated porcine IL-2 fusion toxin control, m2=MFI at saturation and m3=$K_D$. The inset table in A) shows a fitted $K_D$ of 5.1 nM for DT390-pIL-2-Gly. The inset table in B) shows a fitted $K_D$ of 1.94 nM for DT390-pIL-2-Non-N-Gly. The inset table in C) shows a fitted $K_D$ of 0.24 nM for DT390-bi-pIL-2-Gly. The inset table in D) shows a fitted $K_D$ of 0.06 nM for DT390-bi-pIL-2-Non-N-Gly.
Figure 5B:
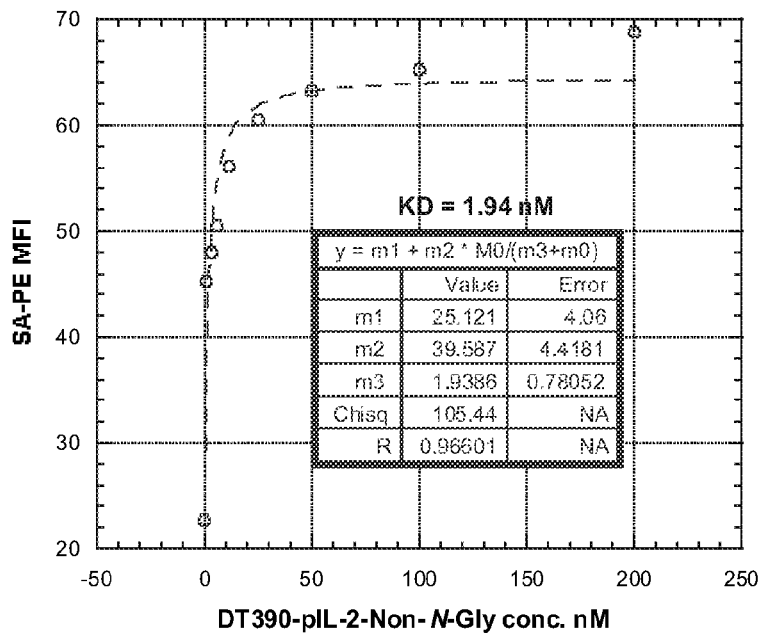
Figure 5C:
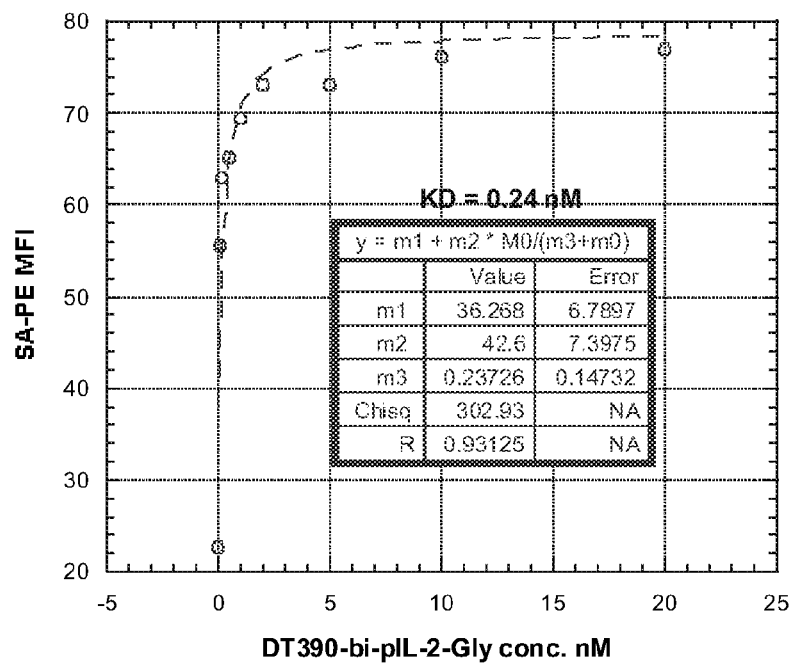
Figure 5D:
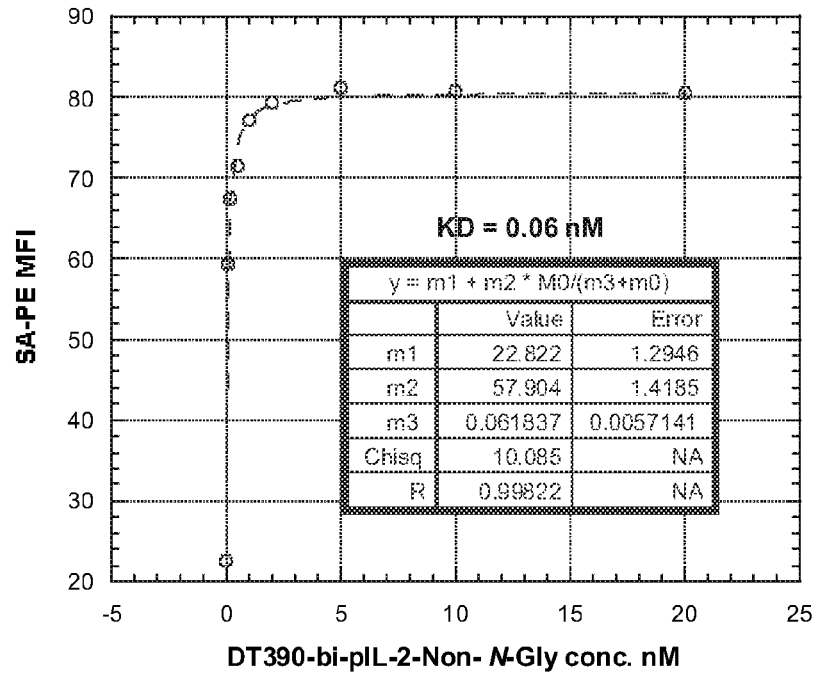

In Vitro Protein Synthesis Inhibition Analysis of the Porcine IL-2 Fusion Toxins FIG. 4 shows that all four porcine IL-2 fusion toxins are capable of inhibiting protein synthesis in vitro in LCL13271 cells. The same analysis also demonstrated that the Bi-NonGly fusion toxin (DT390-bi-pIL2-Non-N-Gly) is the most effective reagent. This Bi-NonGly fusion toxin can efficiently inhibit protein synthesis at relatively low concentrations ($2\times10^{-16}$ M), indicating its extreme potency. Surprisingly further analysis of the Bi-NonGly fusion toxin demonstrated that it can still efficiently inhibit the protein synthesis in vitro very well even at $2\times10^{-28}$ M (data not shown). To our knowledge it is the most potent fusion toxin/immunotoxin as analyzed by in vitro protein synthesis inhibition to date. In addition, the human IL-2 fusion toxin Ontak® (Eisai, Woodcliff Lake, N.J.) was also included as control in this protein synthesis inhibition assay. As shown in FIG. 4, all of the four porcine IL-2 fusion toxins are far more efficient than Ontak®. These results confirm significant species specificity and demonstrate that the porcine IL-2 fusion toxins are most optimal for use in pre-clinical swine models.

Example 1.3

$K_D$ Analysis of the Porcine IL-2 Fusion Toxins Binding to Porcine CD25

In order for these porcine IL-2 fusion toxins to be functional, they must first bind to the cell of interest via CD25 then internalize before inhibiting protein synthesis. Therefore, it was necessary to analyze the ability of these reagents to bind to CD25 on LCL13271 cells and determine if this strength in binding correlated with potency of in vitro protein synthesis inhibition. All four porcine IL-2 fusion toxins had relatively low dissociation constants ($K_D$) (all ≤5.1 nM, FIG. 5A-D) suggesting, that each of these fusion proteins has strong affinity for CD25 on LCL13271 cells. The Bi-NonGly fusion toxin has an extremely low $K_D$ value, 0.06 nM. This isoform was also by far the most potent reagent for inhibiting protein synthesis in vitro, thus these results show a definite correlation between binding and subsequent impeding of protein synthesis.

The binding specificity of porcine IL-2 fusion toxins were also analyzed using blocking/competition of porcine CD25 mAb (clone #231-3B2) to porcine CD25$^+$ LCL 13271 cells by flow cytometry. The blocking/competition assay demonstrated that all of the porcine IL-2 fusion toxins successfully blocked the binding of porcine CD25 mAb to LCL13271 cells and the Bi-NonGly construct is the best (data not shown).

Example 1.4

In Vivo Functional Analysis of the Porcine IL-2 Fusion Toxin Using a Tumor-Bearing NSG Mouse Model A porcine CD25$^+$ tumor (LCL13271)-bearing NSG mouse model was used to assess the in vivo function of the porcine IL-2 Bi-Gly fusion toxin, as follows. A breeding pair of NSG mice were purchased from Jackson laboratories and bred in our rodent barrier facilities for use in this study. All animal care procedures and experiments were approved by the Massachusetts General Hospital Subcommittee on Research Animal Care (SRAC). MGH is an Association for Assessment and Accreditation of Laboratory Animal Care (AAALAC) recognized research institution.

All NSG mice were given injections of 10 million porcine CD25+ tumor cells (LCL13271) IV via the tail vein. Six mice were injected with 50 μg/kg of porcine IL-2 fusion toxin (Bi-Gly version) on day 0 and the drug was administered IP twice a day for 4 days and then once a day every 3 days for 9 days. Controls (n=13) received the tumor cells without the fusion toxin and an additional two mice were given the tumor cells and treated with the drug vehicle (PBS). Injected animals were then observed daily for signs and symptoms of illness and scored biweekly based on several parameters (Schenk et al manuscript in preparation): respiratory effort (0-3), weight loss/gain (0-2), fur integrity (0-3), provoked (0-3) and non-provoked activity (0-1), posture (0-3), abdominal distention (0-3), abdominal palpation (0-3) and body condition score (0-3). The highest score in each category represents the worst possible condition for that parameter. The highest possible score on the scoring system is a 24. Mice were humanely euthanized and necropsy was performed after a score of 12 or higher was achieved or when an animal lost more than 15% of its pre-injection body weight.

Figure 6:
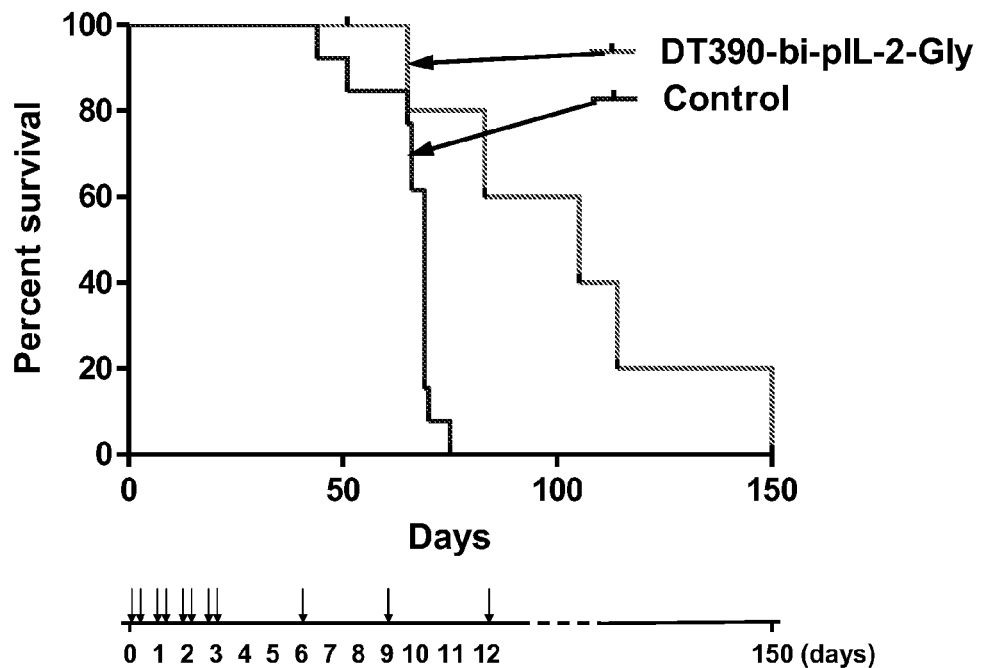
FIG. 6: In vivo Functional Analysis of the Porcine IL-2 Fusion Toxin. NSG mice were injected with porcine CD25+ B-cell lymphoma cells (LCL13271). The experimental group (n=6) treated with DT390-bi-pIL-2-Gly had a median survival time of 105 days (p=0.028) compared to 69 days in untreated controls that received no fusion toxin (n=13). The drug administration schedule was shown using vertical arrows.

NSG mice injected with LCL13271 tumor cells and the Bi-Gly fusion toxin demonstrated prolonged survival in comparison to the untreated mice from a median of 69 days to 105 days (p=0.028) (FIG. 6). Mice that received the Bi-Gly fusion toxin alone did not show any evidence of toxicity at the 50 µg/kg dose. All animals that were injected with LCL13271 cells succumbed to tumors, demonstrated by gross pathology and histopathology. Overall, prolonged survival was observed in mice that were treated with the porcine IL-2 Bi-Gly fusion toxin.

Example 1.5

Porcine Treg Depletion In Vivo by a Non-N-Glycosylated Bivalent Porcine IL-2 Fusion Toxin An in vivo study was performed using an 8 kg MGH MHC-defined miniature swine. All animal care and procedures were in compliance with "Principles of Animal Care" formulated by the National Society for Medical Research and the "Guide for the Care and Use of Laboratory Animals," prepared by the Institute of Laboratory Animal Resources and published by the National Institutes of Health. The animal underwent central line insertion on day 0. The central line insertion was performed as follows. Under general anesthesia, two indwelling silastic catheters were placed in bilateral external jugular veins. Both catheters were used for drug administration and to obtain blood for clinical monitoring and in vitro assays.

The animal was then treated with the non-N-glycosylated bivalent porcine IL-2 fusion toxin at 50 ug/kg, IV, BID given as a bolus for four days. 10 mL of venous blood was collected daily for the first week and then twice a week thereafter for assays.

Peripheral blood mononuclear cells (PBMCs) and whole blood were analyzed by flow cytometry via cell surface staining using mAbs directed against the following antigens: CD25, CD4, CD8, CD3, CD16, CD172, CD5, CD2, CD21; isotype-matched control mAbs were also used. To assess intracellular protein expression of Foxp3, PBMCs were permeabilized using Fixation/Permeabilization solution (eBioscience, San Diego, Calif.) following the manufacturer's instructions. Flow cytometry was performed on a FACS Calibur and data was analyzed using Winlist software.

Figure 7:
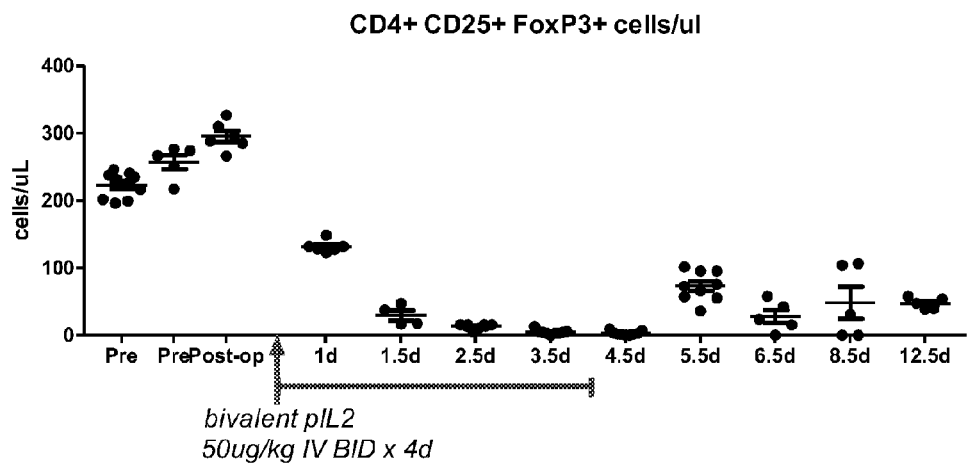
FIG. 7. In vivo porcine Treg (CD4+CD25+Foxp3+) depletion profile using bivalent porcine IL-2 fusion toxin. The animal was treated at 50 ug/kg, IV, BID for 4 days. Porcine Tregs were monitored before, during, and after the treatment.
Figure 8:
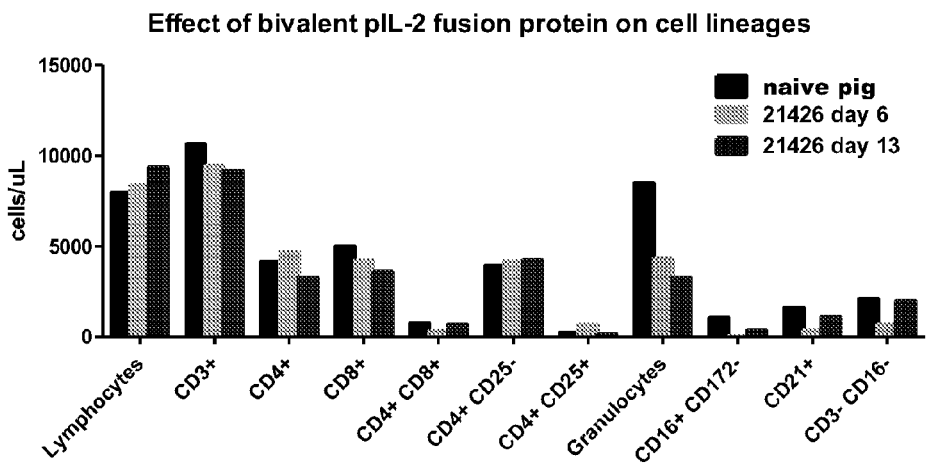
FIG. 8. Depletion specificity of bivalent porcine IL-2 fusion toxin on cell lineages. The effect of bivalent porcine IL-2 fusion toxin on different cell lineages was compared to a naïve, untreated swine (black). The bivalent porcine IL-2 fusion toxin depleted B cells (CD21+ or CD3−CD16−) and NK cells (CD16+ CD172−) as measured on day 6 (brown) and day 13 (blue) after starting treatment.

As shown in FIG. 7, porcine Tregs were effectively depleted for more than 94% after only three dose treatment (1.5 days). The Treg level remained very low (~13% of before depletion) for the duration of the study, i.e., for at least 12.5 days. This fusion toxin specifically depletes Treg without depleting CD4+ and CD8+ T cells (FIG. 8), and also leads to the depletion of NK cells (CD16+ CD172−) and B cells (CD21+ or CD3−CD16−) (FIG. 8).

These results indicate that when administered to a living animal, this reagent can relieve the immune suppression associated with CD25+ Tregs, and thus can be used to enhance the anti-tumor immune response, e.g., alone or in combination with an immunotherapy.

Example 2

Murine IL-2 Fusion Toxin

Example 2 describes the generation and testing of diphtheria toxin based monovalent and bivalent murine IL-2 fusion toxins for depleting murine CD25+ cells in vivo. Their potencies were assessed by in vitro protein synthesis inhibition and cell proliferation inhibition assays using a murine CD25+ CTLL-2 cell line. Surprisingly, in contrast to other recombinant fusion toxins, the monovalent isoform (DT390-mIL-2) is approximately one log more potent than its bivalent counterpart (DT390-bi-mIL-2). Binding analysis by flow cytometry demonstrated that the monovalent isoform bound stronger than the bivalent version. In order to examine the binding specificity, murine IL-2 fusion toxins were used as inhibitor to block the binding of biotinylated murine IL-2 to murine CD25+ CTLL-2 cells using flow cytometry; and murine IL-2 was used as inhibitor to block protein synthesis inhibition and cell proliferation inhibition of the murine IL-2 fusion toxins to murine CD25+ CTLL-2 cells. Those blocking data confirmed that the murine IL-2 fusion toxins specifically bind to the murine IL-2 receptor. In vivo murine Treg depletion was performed using C57BL/6J (B6) mice for the monovalent murine IL-2 fusion toxin. Spleen Treg was significantly depleted maximal to ~70% and the spleen Treg depletion was detectable as early as 12 hours after the treatment. The spleen Treg numbers were reduced until day 3 and returned to control levels by day 7. The levels of other leukocyte populations, including CD4+, CD8+, CD19+ (B cells) and NK-1.1+ (NK cells) cells remained unchanged. This monovalent murine IL-2 fusion toxin is a species-specific and effective in vivo murine Treg depleter.

Materials and Methods

The following materials and methods were used in Example 2 set forth below.

Plasmid Construction

Figure 9:
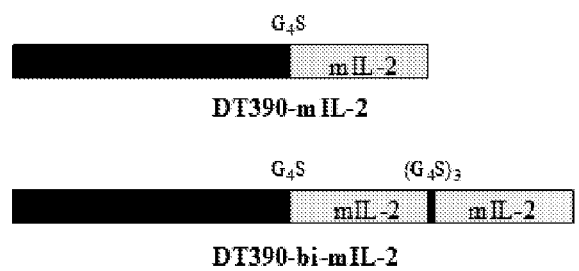
FIG. 9. Schematic Representation of exemplary murine IL-2 fusion toxins.

As shown in FIG. 9, murine IL-2 fusion toxins were built to contain two moieties using the codon-optimized nucleotide sequences; the first is DT390 (Woo et al., 2002) and the second is murine IL-2 (FIG. 10). A strategy previously employed to construct A-dm-DT390biscFv (2-6-15) (Wang et al., 2011) was applied to build these murine IL-2 fusion toxins. The biscFv (2-6-15) moiety was replaced with the codon-optimized murine IL-2. DT390 and murine IL-2 portions were linked by a ($G_4S$) linker made up of four glycine residues and a serine. The two murine IL-2 proteins were linked by a ($G_4S$)$_3$ linker made up of three tandem chains each containing four glycine residues and a serine for building the bi-murine IL-2 fusion toxin. Six histidines (6× His tag) were added to the C-terminus of each construct to facilitate later purification. The codon-optimized murine IL-2 DNA (FIG. 10) was synthesized by GenScript (Piscataway, N.J.). To construct DT390-mIL-2, the codon-optimized murine IL-2 DNA was amplified using PCR primers mIL2-X1 carrying XhoI and NcoI site+mIL2-E1 carrying an EcoRI site then cloned into pwPICZalpha (Peraino et al., Protein Expr Purif. 82, 270-278 (2012)) between XhoI and EcoRI sites for sequencing confirmation. The insert was then cut out with NcoI+EcoRI and cloned into pwPICZalpha-DT390 (Wang et al., 2011) between NcoI and EcoRI sites yielding the final construct DT390-mIL-2 in pwPICZalpha.

To construct DT390-bi-mIL-2, the first murine IL-2 was amplified using PCR primers mIL2-X1 carrying XhoI and NcoI sites+mIL2-Bam1 carrying BamHI and EcoRI sites then cloned into pwPICZalpha between XhoI and EcoRI sites for sequencing confirmation. The insert was subsequently cut out with NcoI+BamHI as insert I. The second murine IL-2 was PCR amplified using mIL2-Bam2 carrying XhoI and BamHI sites+mIL2-E1 carrying an EcoRI site then cloned into pwPICZalpha between XhoI and EcoRI sites for sequencing confirmation. The insert was then cut out with BamHI+EcoRI as insert II. The insert I carrying NcoI and BamHI sites+insert II carrying BamHI and EcoRI sites (NcoI-mIL-2-BamHI/BamHI-mIL-2-EcoRI) were together cloned into pwPICZalpha-DT390 between NcoI and EcoRI yielding the final construct DT390-bi-mIL-2 in pwPICZalpha. All PCR primers that were used are listed in Table 3.

TABLE 3

PCR primers used in this study

| Primer | Sequence | SEQ ID NO: |
|---|---|---|
| mIL2-X1 | CCG<u>CTCGAG</u>CC<u>ATG</u>GGGTGGTGGTGGTTCTGCTCC<br>    XhoI    NcoI<br>AACTTCTTCCTCTACT3' | 18 |
| mIL2-Bam1 | CCG<u>GAATTC</u>CGCCGC<u>GGATCC</u>ACCACCACCAGAAC<br>    EcoRI      BamHI<br>CACCACCACCTTGTGGAGAAGTAGAGATAAT | 19 |
| AGA3' | 5'CCG<u>CTCGAG</u>CGGCGC<u>GGATCC</u>GGTGGTGGTGGT<br>    XhoI      BamHI<br>TCTGCTCCAACTTCTTCCTCTACT3' | 20 |
| mIL2-E1 | 5'CCG<u>GAATTC</u>TTAGTGGTGGTGGTGGTGTTG<br>    EcoRI<br>TGGAGAAGTAGAGATAATAGA3' | 21 |

The sequence of the monovalent murine IL-2 fusion toxin (DT390-mIL-2-6× His) was as follows: (61.11 kDa)

(SEQ ID NO: 28)
AGADDVVDSSKSFVMENFASYHGTKPGYVDSIQKGIQKPKSGTQGNYDD
DWKGFYSTDNKYDAAGYSVDNENPLSGKAGGVVKVTYPGLTKVLALKVD
NAETIKKELGLSLTEPLMEQVGTEEFIKRFGDGASRVVLSLPFAEGSSS
VEYINNWEQAKALSVELEINFETRGKRGQDAMYEYMAQACAGNRVRRSV
GSSLSCINLDWDVIRDKTKTKIESLKEHGPIKNKMSESPAKTVSEEKAK
QYLEEFHQTALEHPELSELKTVTGTNPVFAGANYAAWAVNVAQVIDSET
ADNLEKTTAALSILPGIGSVMGIADGAVHHNTEEIVAQSIALSSLMVAQ
AIPLVGELVDIGFAAYNFVESIINLFQVVHNSYNRPAYSPGHKTQPFLP
WGGGGSAPTSSSTSSSTAEAQQQQQQQQQQQQHLEQLLMDLQELLSRME
NYRNLKLPRMLTFKFYLPKQATELKDLQCLEDELGPLRHVIDLTQSKSF
QLEDAENFISNIRVTVVKLKGSDNTFECQFDDESATVVDFLRRWIAFCQ
SIISTSPQHHHHHH

The sequence of the bivalent murine IL-2 fusion toxin (DT390-bi-mIL-2-6×His) was as follows: 79.27 kDa (SEQ ID NO: 29)
AGADDVVDSSKSFVMENFASYHGTKPGYVDSIQKGIQKPKSGTQGNYD
DDWKGFYSTDNKYDAAGYSVDNENPLSGKAGGVVKVTYPGLTKVLALK
VDNAETIKKELGLSLTEPLMEQVGTEEFIKRFGDGASRVVLSLPFAEG
SSSVEYINNWEQAKALSVELEINFETRGKRGQDAMYEYMAQACAGNRV
RRSVGSSLSCINLDWDVIRDKTKTKIESLKEHGPIKNKMSESPAKTVS
EEKAKQYLEEFHQTALEHPELSELKTVTGTNPVFAGANYAAWAVNVAQ
VIDSETADNLEKTTAALSILPGIGSVMGIADGAVHHNTEEIVAQSIAL
SSLMVAQAIPLVGELVDIGFAAYNEVESIINLFQVVHNSYNRPAYSPG
HKTQPFLPWGGGGSAPTSSSTSSSTAEAQQQQQQQQQQQQHLEQLLMD
LQELLSRMENYRNLKLPRMLTFKFYLPKQATELKDLQCLEDELGPLRH
VLDLTQSKSFQLEDAENFISNIRVTVVKLKGSDNTFECQFDDESATVV
DFLRRWIAFCQSIISTSPQGGGGSGGGGSGGGGSAPTSSSTSSSTAEA
QQQQQQQQQQQQHLEQLLMDLQELLSRMENYRNLKLPRMLTFKFYLPK
QATELKDLQCLEDELGPLRHVLDLTQSKSFQLEDAENFISNIRVTVVK
LKGSDNTFECQFDDESATVVDFLRRWIAFCQSIISTSPQHHHHHH

Protein expression and purification in *Pichia pastoris* were performed as previously described (Wang et al., 2011; Peraino et al., J Immunol Methods 391, 103 (2013)). Western blot analysis, FACS analysis and FACS competition/blocking analysis were all performed as previously described (Peraino et al., Protein Expr Purif. 82, 270-278 (2012)) using murine $CD25^+$ CTLL-2 cell line. The DT390 alone, murine IL-2 alone, Ontak-Like® monovalent human IL-2 fusion toxin (DT390-hIL-2) (see Example 3) and bivalent human IL-2 fusion toxin (DT390-bi-hIL-2) (see Example 3) were used as controls for our in vitro assay. These products were also expressed and purified in the yeast *Pichia Pastoris* system.

Protein Synthesis Inhibition

Murine CTLL-2 cells were cultured in RPMI 1640 media supplemented with 6% fetal bovine serum, 10 mM hepes (N-2-hydroxyethylpiperazine-N-2-ethanesulfonic acid), 1x nonessential amino acids, 1 mM sodium pyruvate, 2 mM glutamine, and $2.5 \times 10^{-5}$M 2-mercaptoethanol. Cells were washed twice with 50 mL of the above media containing leucine-free RPMI by centrifugation at 1000 rpm, 20° C. for 5 minutes. CTLL-2 cells were then diluted to $5.0 \times 10^5$ cells/mL and each murine IL-2 fusion toxin was serially diluted in the above culture media with leucine-free RPMI. One hundred microliters of cells ($5.0 \times 10^4$ cells) was added to each well in a 96-well flat bottom plate (Corning) with 10 μL of fusion toxin dilution and incubated at 37° C. with 5% $CO_2$ for 18 hours. Each fusion toxin dilution was analyzed in triplicate. Plates were pulsed with 1 μCi/well of $^3$H-leucine for 1 hour then harvested onto filter mats (Perkin-Elmer) using a Harvester 96® Mach II cell harvester and allowed to dry at room temperature overnight. Beta emission was determined in counts per million (cpm) read using a microbeta counter. The negative control for this assay was murine CTLL-2 cells plated without fusion toxin and the positive control was murine CTLL-2 cells plated with cycloheximide (1:8) for 15 minutes at 37° C. with 5% $CO_2$. Both controls were analyzed in triplicate for each assay.

The blocking assays follow the protocol above with a 1-hour incubation of 10 μL of the murine IL-2 as inhibitor ($10^{-9}$ M as the final concentration) with the murine CTLL-2 cells prior to addition of the fusion toxins. The inhibition assays were then pulsed, harvested and read as described above.

Cellular Proliferation Inhibition

Murine CD25+ CTLL-2 cells were cultured in RPMI 1640 media supplemented with 6% fetal bovine serum, 10 mM hepes (N-2-hydroxyethylpiperazine-N-2-ethanesulfonic acid), 1× nonessential amino acids, 1 mM sodium pyruvate, 2 mM glutamine, and $2.5 \times 10^{-5}$ M 2-mercaptoethanol. Cells were washed twice with 50 mL of the above media by centrifugation at 1000 rpm, 20° C. for 5 minutes. Murine CTLL-2 cells were then diluted to $5.0 \times 10^5$ cells/mL and each murine IL-2 fusion toxin was serially diluted in the above culture media. One hundred microliters of cells ($5.0 \times 10^4$ cells) was added to each well in a 96-well flat bottom plate (Corning) with 10 µL of fusion toxin dilution and incubated at 37° C. with 5% $CO_2$ for 24 hours. Each fusion toxin dilution was analyzed in triplicate. Plates were pulsed with 1 µCi/well of $^3$H-thymidine for 24 hours then harvested onto filter mats (Perkin-Elmer) using a Harvester 96® Mach II cell harvester and allowed to dry at room temperature overnight. Beta emission was determined in counts per million (cpm) read using a microbeta counter. The negative control for this assay was murine CTLL-2 cells plated without fusion toxin and the positive control was murine CTLL-2 cells plated with cycloheximide (1:8) for 1 hour at 37° C. with 5% $CO_2$. Both controls were analyzed in triplicate. The inhibition assays follow the protocol above with a 1-hour incubation of 10 µL of the murine IL-2 as inhibitor ($10^{-9}$ M as the final concentration) with the murine CTLL-2 cells prior to addition of the fusion toxins. Inhibition assays were then pulsed, harvested and read as described above.

In Vivo Treg Depletion

Spleen cells were extracted and analyzed using the following antibodies: APC/Cy7-anti-mouse CD4 (RM4-5) purchased form BioLegend, PE/Cy7-anti-mouse CD8 (53-6.7) purchased form BioLegend, PE-anti-rat CD19 (1D3) purchased form BD Biosciences, FITC Rat anti-mouse CD25 (7D4), anti-mouse/rat Foxp3 (FJK-16s) and PerCP/Cy5.5-anti-mouse NK1.1 (PK136). Flow cytometry was performed on a FACSverse and data were analyzed with FlowJo software.

Example 2.1

Expression and Purification of Murine IL-2 Fusion Toxins in Yeast *Pichia Pastoris*

As shown in FIG. 9, both monovalent and bivalent murine IL-2 fusion toxins were constructed so as to find the best isoform for in vivo murine Treg depletion. The codon-optimized murine IL-2 (FIG. 10) was cloned into a DT-390-containing yeast *Pichia Pastoris* expression vector pwPIC-Zalpha-DT390 between NcoI and EcoRI (Wang et al., 2011). A $G_4S$ linker was used to link the DT390 domain to the murine IL-2 domain. A $(G_4S)_3$ linker was used to connect between two murine IL-2 domains to generate the bivalent murine IL-2 fusion toxin. A 6×His tag was added to the C-terminus of the murine IL-2 fusion toxins to facilitate the downstream purification. The murine IL-2 fusion toxins were expressed using diphtheria-toxin resistant yeast *Pichia pastoris* strain (Liu et al., 2007) in shaking flasks. The expressed murine IL-2 fusion toxins in the supernatant was captured using Ni-Sepharose fast flow resin and further purified using a strong anion-exchange resin Poros 50 HQ. The final production level is ~4 mg/L of the original harvested supernatant for the monovalent and bivalent murine IL-2 fusion toxins. The purified murine IL-2 fusion toxins were analyzed using SDS PAGE (FIG. 11A) and Western blotting with anti-6×His tag mAb (FIG. 11B) and anti-diphtheria toxin mAb (FIG. 11C).

Example 2.2

Protein Synthesis Inhibition Analysis of the Murine IL-2 Fusion Toxins

Figure 12:
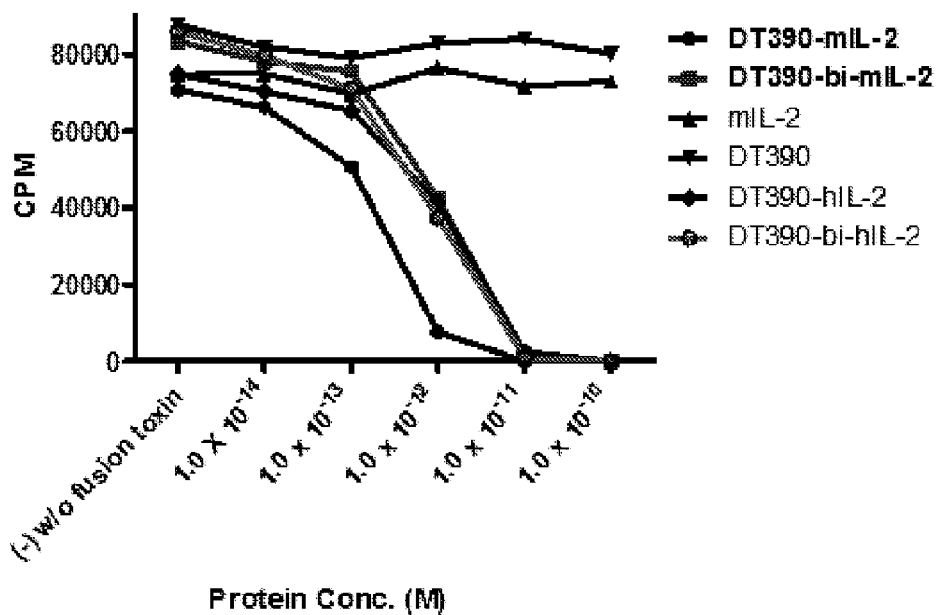
FIG. 12. In vitro protein synthesis inhibition analysis of the murine IL-2 fusion toxins using murine CD25+ CTLL-2 cells: 1) Monovalent murine IL-2 fusion toxin (DT390-mIL-2, red line); 2) Bivalent murine IL-2 fusion toxin (DT390-bi-mIL-2, green line); 3) murine IL-2 alone (blue line); 4) DT390 alone (black line); 5) Ontak®-like monovalent human IL-2 fusion toxin as control (DT390-hIL-2, pink line); 6) Bivalent human IL-2 fusion toxin as control (DT390-bi-hIL-2, brown line). Y-axis: cpm value measuring incorporation of tritiated leucine. X-axis: plated IL-2 fusion toxin concentration. Cycloheximide (1:8) was used as a positive control. The negative control contained cells without fusion toxin. Data are representative of multiple individual assays.

The potency of the murine IL-2 fusion toxins was assessed by in vitro protein synthesis inhibition assay using the murine CD25+ CTLL-2 cell line through incorporation of the tritiated leucine. As shown in FIG. 12, the monovalent murine IL-2 fusion toxin (DT390-mIL-2) is approximately one log more potent than the bivalent murine IL-2 fusion toxin (DT390-bi-mIL-2). DT390 alone, murine IL-2 alone, monovalent human IL-2 fusion toxin (DT390-hIL-2) and bivalent human IL-2 fusion toxin (DT390-bi-hIL-2) were included as controls. The monovalent murine IL-2 fusion toxin was more potent than both monovalent and bivalent human IL-2 fusion toxins. It was hypothesized that the bivalent murine IL-2 fusion toxin might be more potent than the monovalent isoform as we previously observed with other bivalent immunotoxins (Woo et al., 2002; Kim et al., Protein Eng. Des. Sel. 20, 425 (2007); Wang et al., 2011). Surprisingly the monovalent murine IL-2 fusion toxin is more potent than its bivalent counterpart. It is possible that the conformation of the bivalent isoform is not optimal for its binding to murine CD25.

Example 2.3

Cell Proliferation Inhibition Analysis of the Murine IL-2 Fusion Toxins

Figure 13:
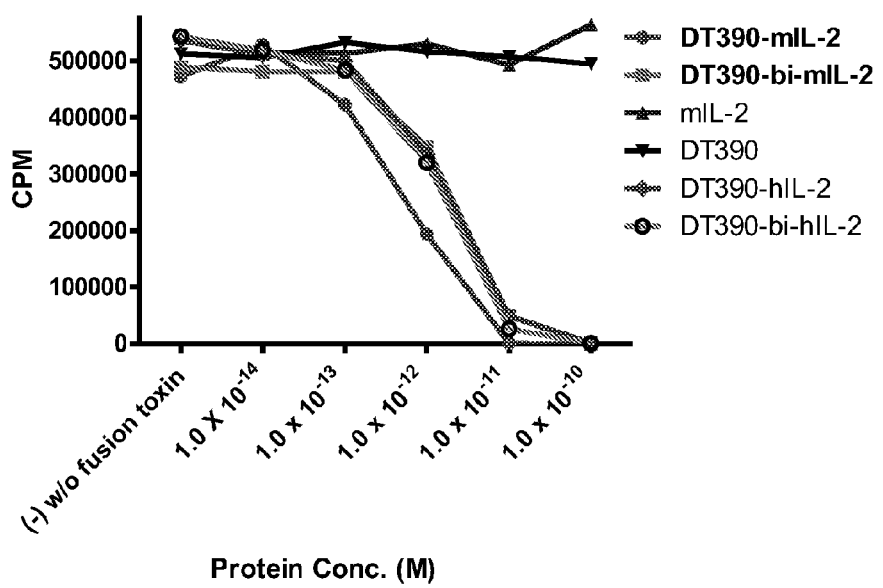
FIG. 13. In vitro cell proliferation inhibition analysis of the murine IL-2 fusion toxins using murine CD25+ CTLL-2 cells: 1) Monovalent murine IL-2 fusion toxin (DT390-mIL-2, red line); 2) Bivalent murine IL-2 fusion toxin (DT390-bi-mIL-2, green line); 3) Murine IL-2 alone (blue line); 4) DT390 alone (black line); 5) Ontak®-like monovalent human IL-2 fusion toxin as control (DT390-hIL-2, pink line); 6) Bivalent human IL-2 fusion toxin as control (DT390-bi-hIL-2, brown line). Y-axis: cpm value measuring incorporation of tritiated thymidine. X-axis: plated IL-2 fusion toxin concentration. Cycloheximide (1:8) was used as a positive control. The negative control contained cells without fusion toxin. Data are representative of multiple assays.

To double assess the potency of the murine IL-2 fusion toxins, an in vitro cell proliferation inhibition assay was performed using murine CD25+ CTLL-2 cell line through incorporation of tritiated thymidine. As shown in FIG. 13, the cell proliferation inhibition analysis demonstrated that the monovalent murine IL-2 fusion toxin is more potent than the bivalent counterpart which is consistent with the previously described protein synthesis inhibition analysis. DT390 alone, soluble murine IL-2 alone, DT390-hIL-2 and DT390-bi-hIL-2 were also included as controls. The monovalent murine IL-2 fusion toxin is more potent than both monovalent and bivalent human IL-2 fusion toxins in this cell proliferation inhibition assay.

Example 2.4

Flow Cytometry Binding Analysis of the Murine IL-2 Fusion Toxins

Figure 14:
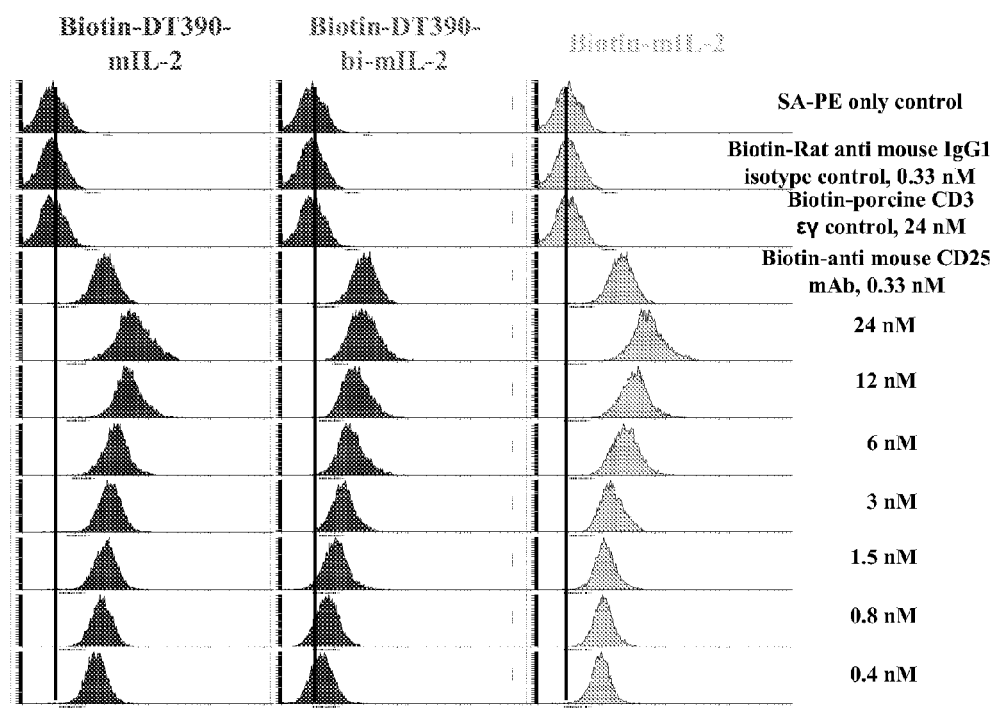
FIG. 14. Flow cytometry binding analysis of the murine IL-2 fusion toxins to the murine CD25+ CTLL-2 cells. 1) DT390-mIL-2 (left panel); 2) DT390-bi-mIL-2 (middle panel); 3) Positive control murine IL-2 (right panel). Only second staining control (PE-conjugated streptavidin), biotinylated rat anti-mouse IgG1 isotype control, biotinylated porcine CD3εγ control (Peraino et al., 2012b) and biotinylated rat-anti-mouse CD25 mAb as positive control were also included. The data are representative of multiple individual experiments.

In order to inhibit the target cell protein synthesis, the fusion toxin must bind to the target cell receptor and then be internalized into the cytosol through endocytosis. Therefore, binding to the cell surface is the first critical step in inhibiting protein synthesis. The murine IL-2 fusion toxins were designed to bind to cells expressing the high affinity murine IL-2 receptor consisting of IL-2Rα (CD25), IL-2Rβ (CD122) and common cytokine receptor $\gamma_c$ (CD132) subunits. The binding affinity of the murine IL-2 fusion toxins to the murine IL-2 receptor were analyzed by flow cytometry using a murine CD25+ CTLL-2 cell line. As shown in FIG. 14, the monovalent fusion toxin (left panel) bound to the murine CD25+ IL-2 receptor stronger than the bivalent isoform (middle panel) which correlated well with the protein synthesis inhibition and cell proliferation inhibition analysis described previously.

Example 2.5

Binding Specificity Analysis of the Murine IL-2 Fusion Toxins

Figure 15:
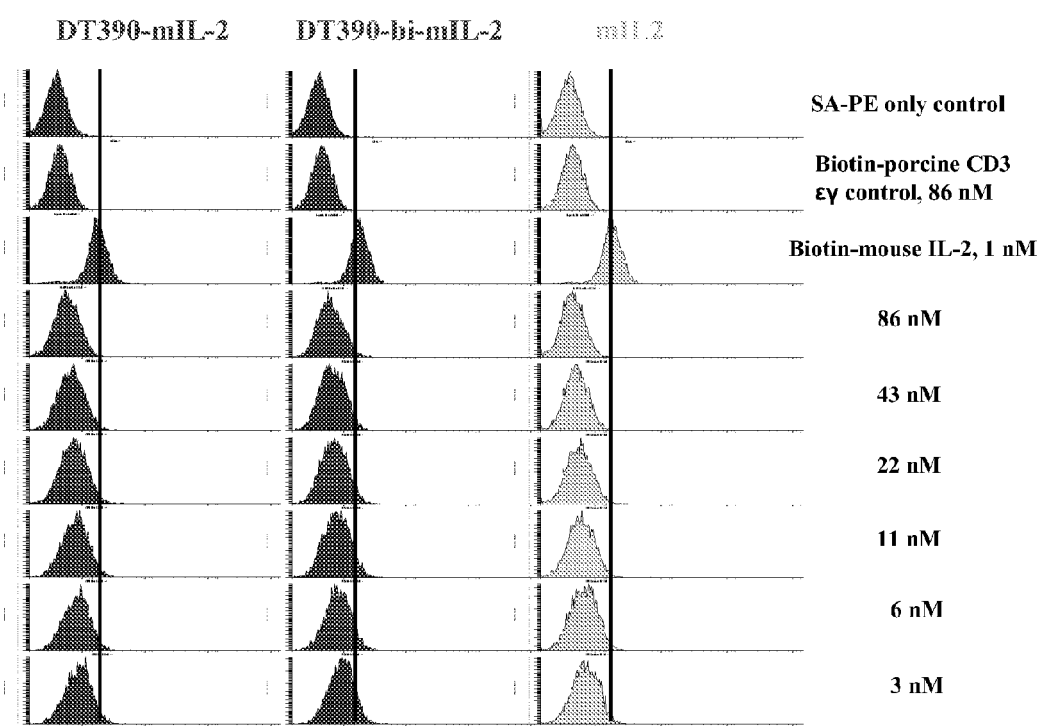
FIG. 15. Binding specificity of the murine IL-2 fusion toxins for the murine IL-2 receptor on murine CD25+ CTLL-2 cells. Unlabeled murine IL-2 fusion toxins as well as the positive control murine IL-2 were each incubated with murine CD25+ CTLL-2 cells at a range of concentrations for 15 minutes at 4° C. in the dark. Subsequently, without washing the cells, biotin-labeled murine IL-2 was added to each tube containing cells in the presence of the unlabeled murine IL-2 fusion toxin. Binding specificity of the murine IL-2 fusion toxin or murine IL-2 to the IL-2 receptor on murine CD25+ CTLL-2 cells was measured by a decrease in biotin-labeled murine IL-2 staining in the presence of increasing concentrations of the unlabeled inhibitor proteins. Biotin-labeled porcine CD3-εγ was included as a negative control for background due to protein biotinylation.
Figure 16A:
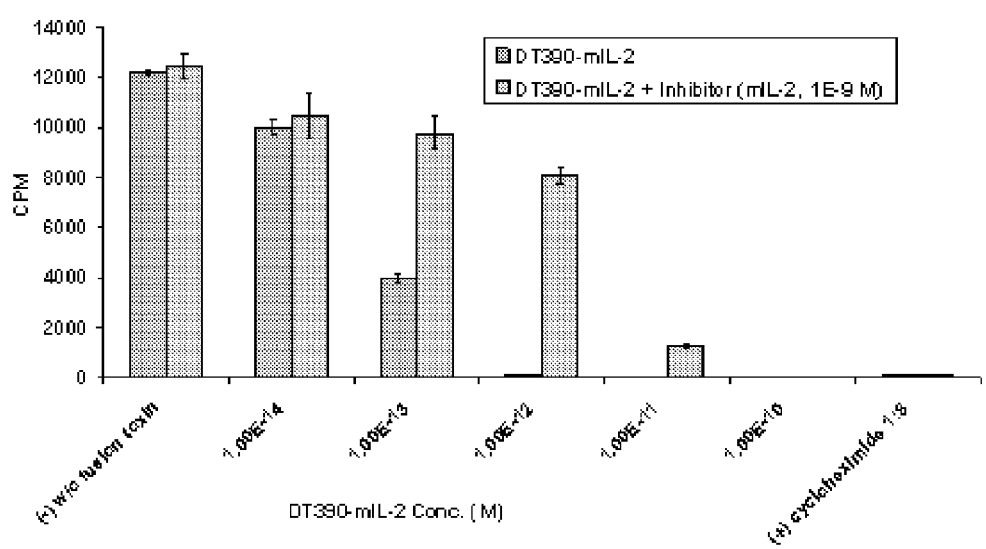
FIGS. 16A-B. Binding specificity analysis of the murine IL-2 fusion toxins to the target murine CD25$^+$ CTLL-2 cells in the in vitro protein synthesis inhibition assay using murine IL-2 as inhibitor: A) Monovalent murine IL-2 fusion toxin (DT390-mIL-2) with (green) or without (orange) inhibitor, murine IL-2; B) bivalent murine IL-2 fusion toxin (DT390-bi-mIL-2) with (pink) or without (blue) inhibitor, murine IL-2. Y-axis: cpm value measuring incorporation of tritiated leucine. X-axis: plated murine IL-2 fusion toxin concentration. Wells containing the murine IL-2 as inhibitor were incubated for 1 hr at 37° C. before addition of fusion toxin. Cycloheximide (1:8) was used as a positive control. Cells without fusion toxin served as the negative control. Data are representative of multiple assays.
Figure 16B:
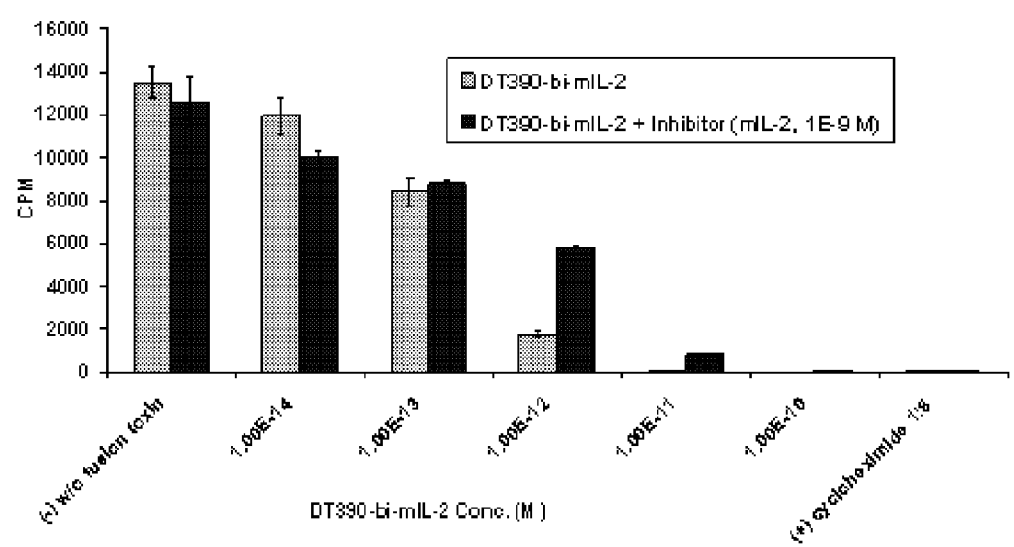
Figure 16C:
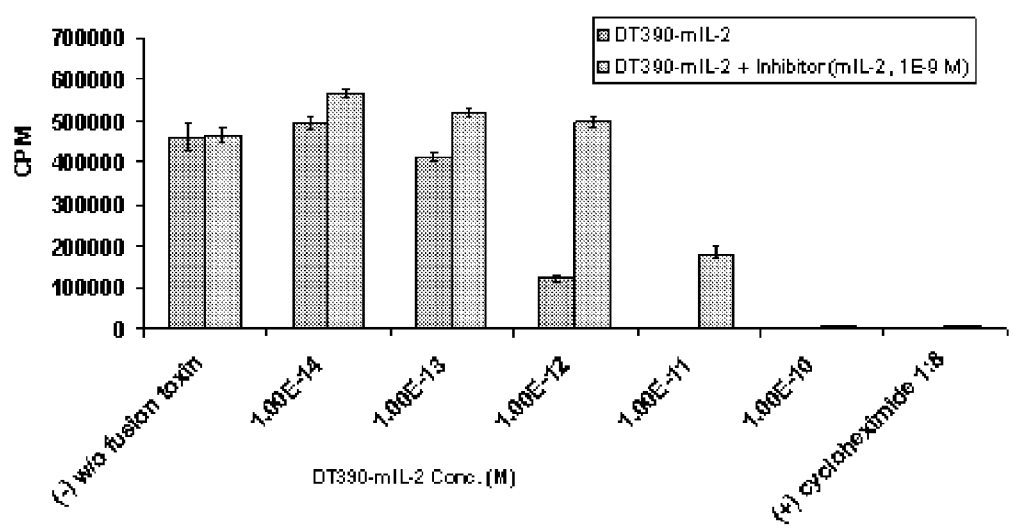
FIGS. 16C-D. Binding specificity analysis of the murine IL-2 fusion toxins to the target murine CD25$^+$ CTLL-2 cells during the in vitro cellular proliferation inhibition assay using murine IL-2 as inhibitor; C) Monovalent murine IL-2 fusion (DT390-mIL-2) toxin with (green) and without (orange) inhibitor, murine IL-2; D) bivalent murine IL-2 fusion toxin (DT390-bi-mIL-2) with (pink) and without (blue) inhibitor, murine IL-2. Y-axis: cpm value measuring cellular incorporation of tritiated thymidine. X-axis: plated murine IL-2 fusion toxin concentration. Wells containing the inhibitor, murine IL-2 were incubated for 1 hr at 37° C. before addition of the fusion toxin. Cycloheximide (1:8) was used as a positive control. Cells without fusion toxin served as the negative control. Data are representative of multiple assays.
Figure 16D:
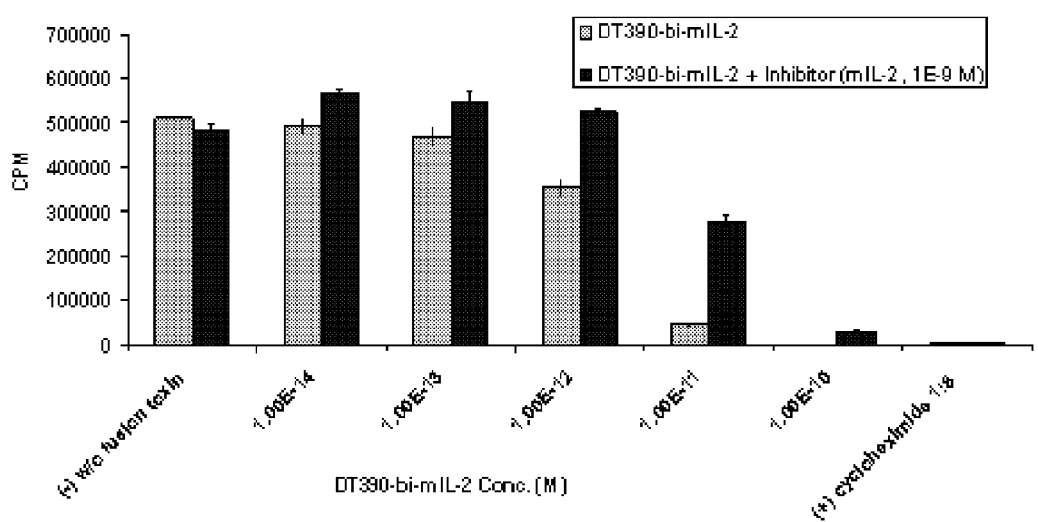

To examine the binding specificity of the murine IL-2 fusion toxins, two blocking assays were performed. 1) Unlabeled murine IL-2 fusion toxins were used as inhibitor to block the binding of biotinylated murine IL-2 to the murine CD25+ CTLL-2 cells. As shown in FIG. 15, both unlabeled monovalent (left panel) and bivalent (middle panel) murine IL-2 fusion toxins blocked the binding of biotinylated murine IL-2 to murine CD25+ CTLL-2 cells in a dose dependent manner similar as the murine IL-2 alone does (right panel). 2) Murine IL-2 was used as inhibitor to block protein synthesis inhibition and cell proliferation inhibition of the murine IL-2 fusion toxins. As shown in FIGS. 16A-D, murine IL-2 blocked the protein synthesis inhibition and cell proliferation inhibition of both monovalent and bivalent murine IL-2 fusion toxins in a dose dependent manner. These blocking assay data confirmed that the murine IL-2 fusion toxins bind specifically to the murine IL-2 receptor on the CTLL-2 cell surface. In addition, these blocking assays also demonstrated that the monovalent murine IL-2 fusion toxin is more potent than the bivalent isoform.

Example 2.6

In Vivo Treg Depletion Using the Monovalent Murine IL-2 Fusion Toxin

Figure 17:
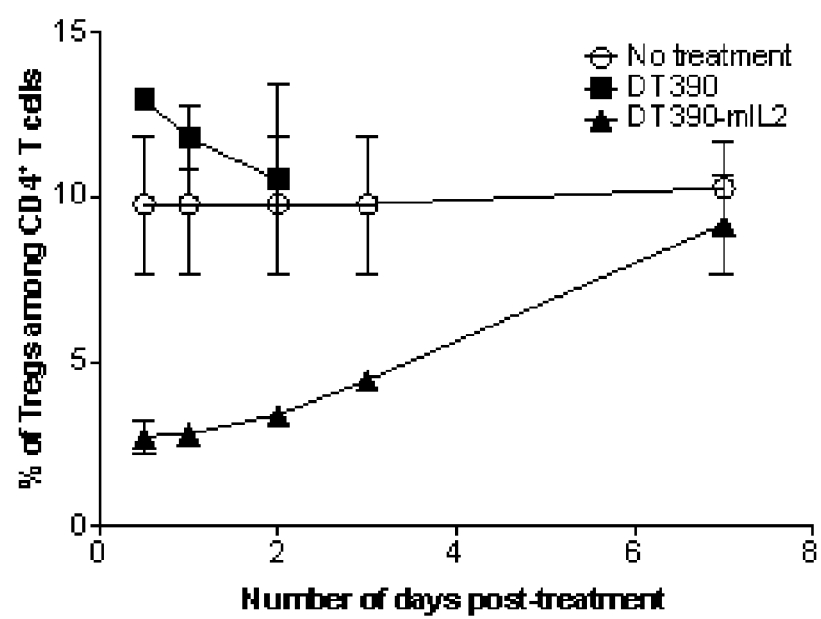
FIG. 17. Kinetics of depletion of CD4$^+$CD25$^+$FoxP3$^+$ T cells (Tregs) after administration of DT390-mIL-2. C57BL/6J (B6) mice were injected intraperitoneally with 5 ug/mouse/day of DT390-mIL-2 or control DT390 for 4 consecutive days. The frequencies of CD4$^+$CD25$^+$FoxP3$^+$ T cells (Tregs) were monitored in each group (n=3 per group) at different time points following the last injection of DT390 or DT390-mIL-2 Also, at each time point both groups were compared with untreated C57BL/6J female mice. The results are expressed as percentage of Tregs among CD4$^+$ T cells±SD.

C57BL/6J (B6) mice were injected intraperitoneally with 5 ug/mouse/day of DT390-mIL-2 or control DT390 for 4 consecutive days. The levels of CD4+CD25+FoxP3+ T cells (Tregs) among spleen cells were monitored by FACS at day 0.5, 1, 2, 3 and 7 after the last injection of control DT390 or DT390-mIL2. As shown in FIG. 17, a significant decrease in Treg frequencies was observed in the group treated with DT390-mIL-2 detectable as early as 12 hours after treatment. Treg cell numbers were reduced until day 3 and returned to control levels by day 7. In contrast, injection of control DT390 compound did not result in a decrease of Tregs numbers and even induced a slight and transient increase in Tregs frequencies, presumably due to some pro-inflammatory effects of the toxin. On the other hand, the levels of other leukocyte populations, including CD4+, CD8+, CD19+ (B cells) and NK-1.1+ (NK cells) cells remained unchanged upon the administration of DT390 or DT390-mIL-2 (data not shown).

Example 3

Human IL-2 Fusion Toxin

Example 3 describes the generation and testing of a human IL-2 fusion toxin. In this study both monovalent and bivalent human IL-2 fusion toxins were expressed using a yeast *Pichia pastoris* expression system and assessed their functions in vitro using protein synthesis inhibition and cellular proliferation inhibition assays. The binding affinity of these recombinant fusion toxins to human CD25 was analyzed using flow cytometry. Binding specificity was determined using the human IL-2 fusion toxins as inhibitors to block the binding of biotinylated human IL-2 to human CD25+ cells by flow cytometry and utilizing human IL-2 as an inhibitor to block the ability of the human IL-2 fusion toxins to inhibit protein synthesis and cellular proliferation in human CD25+ cells in vitro.

Materials and Methods

The following materials and methods were used in Example 3 set forth below.

Plasmid Construction

As shown in FIG. 18, human IL-2 fusion toxins were constructed using the codon-optimized nucleotide sequences and contain two moieties; DT390 (Woo et al., 2002) and human IL-2 (FIG. 19). A strategy previously employed to generate A-dm-DT390biscFv (2-6-15) (Wang et al., 2011) was applied to construct these human IL-2 fusion toxins, substituting codon-optimized human IL-2 for the biscFv (2-6-15) moiety. DT390 and human IL-2 domains are connected by a linker consisting of four glycines and a serine residue ($G_4S$). The two human IL-2 domains of the bivalent fusion toxin are joined by three tandem $G_4S$ linkers $(G_4S)_3$. Six histidines (6× His tag) were added to the C-terminus of each construct to facilitate protein purification. The codon-optimized human IL-2 DNA (FIG. 19) was synthesized by PCR amplification as described previously (Hermanrud et al., 2011). To construct DT390-hIL-2, the codon-optimized human IL-2 DNA was amplified using PCR primers hIL2-X1 carrying XhoI and NcoI site+hIL2 Rev carrying an EcoRI site then cloned into pwPICZalpha (Peraino et al., Protein Expr Purif. 82, 270-278 (2012)) between XhoI and EcoRI sites for sequencing confirmation. The insert was then cut out with NcoI+EcoRI and cloned into pwPICZalpha-DT390 (Wang et al., 2011) between NcoI and EcoRI sites yielding the final construct DT390-hIL-2 in pwPICZalpha. To construct DT390-bi-hIL-2, the first human IL-2 was amplified using PCR primers hIL2-X1 carrying XhoI and NcoI sites+hIL2-Bam1 carrying BamHI and EcoRI sites then cloned into pwPICZalpha between XhoI and EcoRI sites for sequencing confirmation. The insert was subsequently cut out with NcoI+BamHI as insert I. The second human IL-2 was PCR amplified using hIL2-Bam2 carrying XhoI and BamHI sites+hIL-2 Rev carrying an EcoRI site then cloned into pwPICZalpha between XhoI and EcoRI sites for sequencing confirmation. The insert was then cut out with BamHI+EcoRI as insert II. The insert I carrying NcoI and BamHI sites+insert II carrying BamHI and EcoRI sites (NcoI-hIL-2-BamHI/BamHI-hIL-2-EcoRI) were together cloned into pwPICZalpha-DT390 between NcoI and EcoRI yielding the final construct DT390-bi-hIL-2 in pwPICZalpha. All PCR primers that were used are listed in Table 4.

| Primer | Sequence | SEQ ID NO: |
|---|---|---|
| hIL2-X1 | 5' CCG CTC GAG CCA TGG GGT GGT<br>       XhoI      NcoI<br>GGT GGT TCT GCT CCA ACT TCT TCT<br>TCT ACT 3' | 22 |

| Primer | Sequence | SEQ ID NO: |
|---|---|---|
| hIL2-Bam1 | 5' CCG GAA TTC CGC CGC GGA TCC ACC ACC ACC AGA ACC ACC ACC AGT CAA AGT AGA GAT AAT AGA TTG 3'<br>     EcoRI        BamHI | 23 |
| hIL2 Bam2 | 5' CCG CTC GAG CGG GCG GGA TCC GGT GGT GGT GGT TCT GCT CCA ACT TCT TCT TCT ACT 3'<br>     XhoI        BamHI | 24 |
| hIL2 Rev | 5' CCG GAA TTC TTA GTG GTG GTG GTG GTG GTG AGT CAA AGT AGA GAT AAT AGA TTG 3'<br>     EcoRI | 25 |

The sequence of the monovalent human IL-2 fusion toxin (DT390-hIL-2-6×His) was as follows: 59.3 kDa (SEQ ID NO: 30)
AGADDVVDSSKSFVMENFASYHGTKPGYVDSIQKGIQKPKSGTQGNYDD

DWKGFYSTDNKYDAAGYSVDNENPLSGKAGGVVKVTYPGLTKVLALKVD

NAETIKKELGLSLTEPLMEQVGTEEFIKRFGDGASRVVLSLPFAEGSSS

VEYINNWEQAKALSVELEINFETRGKRGQDAMYEYMAQACAGNRVRRSV

GSSLSCINLDWDVIRDKTKTKIESLKEHGPIKNKMSESPAKTVSEEKAK

QYLEEFHQTALEHPELSELKTVTGTNPVFAGANYAAWAVNVAQVIDSET

ADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLP

WGGGGSAPTSSSTKKTQLQLEHLLLDLQMILNGINNYKNPKLTRMLTFK

FYMPKKATELKHLQCLEEELKPLEEVLNLAQSKNFHLRPRDLISNINVI

VLELKGSETTFMCEYADETATIVEFLNRWITFCQSIISTLTHHHHHH

The sequence of the Bivalent human IL-2 fusion toxin (DT390-bi-hIL-2-6×His) was as follows: 75.6 kDa (SEQ ID NO: 31)
AGADDVVDSSKSFVMENFASYHGTKPGYVDSIQKGIQKPKSGTQGNYDD

DWKGFYSTDNKYDAAGYSVDNENPLSGKAGGVVKVTYPGLTKVLALKVD

NAETIKKELGLSLTEPLMEQVGTEEFIKRFGDGASRVVLSLPFAEGSSS

VEYINNWEQAKALSVELEINFETRGKRGQDAMYEYMAQACAGNRVRRSV

GSSLSCINLDWDVIRDKTKTKIESLKEHGPIKNKMSESPAKTVSEEKAK

QYLEEFHQTALEHPELSELKTVTGTNPVFAGANYAAWAVNVAQVIDSET

ADNLEKTTAALSILPGIGSVMGIADGAVHHNTEEIVAQSIALSSLMVAQ

AIPLVGELVDIGFAAYNFVESIINLFQVVHNSYNRPAYSPGHKTQPFLP

WGGGGSAPTSSSTKKTQLQLEHLLLDLQMILNGINNYKNPKLTRMLTFK

FYMPKKATELKHLQCLEEELKPLEEVLNLAQSKNFHLRPRDLISNINVI

VLELKGSETTFMCEYADETATIVEFLNRWITFCQSIISTLTGGGSGGG

GSGGGGSAPTSSSTKKTQLQLEHLLLDLQMILNGINNYKNPKLTRMLTF

KFYMPKKATELKHLQCLEEELKPLEEVLNLAQSKNFHLRPRDLISNINV

IVLELKGSETTFMCEYADETATIVEFLNRWITFCQSIISTLTHHHHHH

Protein expression in *Pichia pastoris* and subsequent purifications were performed as previously described (Wang et al., 2011; Example 1 and Peraino et al., J Immunol Methods 391, 103 (2013)). Western blot analysis, binding affinity and specificity analysis by flow cytometry and $K_d$ determination were all performed as previously described (Example 1 and Peraino et al., J Immunol Methods 391, 103 (2013)) using a human CD25+ T-cell lymphoma cell line HUT 102/6TG (William et al., 1990) (kindly provided by Dr. Robert Harrison, Anjin Group, Inc., Boston, Mass.). DT390 and human IL-2 were used as controls for all in vitro functional analysis. These products were also expressed in the yeast *Pichia Pastoris* system.

Protein Synthesis Inhibition

Human CD25+ T-cell lymphoma cells HUT 102/6TG were cultured in RPMI 1640 media supplemented with 12% fetal bovine serum, 10 mM hepes (N-2-hydroxyethylpiperazine-N-2-ethanesulfonic acid), 1x nonessential amino acids, 1 mM sodium pyruvate, 2 mM glutamine, and $2.5 \times 10^{-5}$ M 2-mercaptoethanol. Cells were washed twice with 50 mL of the above media containing leucine-free RPMI by centrifugation at 1000 rpm, 20° C. for 5 minutes. HUT 102/6TG cells were then diluted to $5.0 \times 10^5$ cells/mL and each human IL-2 fusion toxin was serially diluted in the above culture media with leucine-free RPMI. One hundred microliters of cells ($5.0 \times 10^4$ cells) was added to each well in a 96-well flat bottom plate (Corning) with 10 μL of fusion toxin dilution and incubated at 37° C. with 5% $CO_2$ for 18 hours. Each fusion toxin dilution was analyzed in triplicate. Plates were pulsed with 1 μCi/well of $^3$H-leucine for 1 hour and then centrifuged at 170×g for 5 min. at 4° C. The supernatant was discarded and the cells were lysed by adding 50 μL of potassium hydroxide (4 M) to each well for 10 min at room temperature. Proteins were precipitated by adding 150 μL of trichloroacetic acid (10% w/v) then plates were harvested onto filter mats (Perkin-Elmer) using a Harvester 96® Mach II cell harvester and allowed to dry at room temperature overnight. Beta emission was determined in counts per million (cpm) read using a microbeta counter. The negative control for this assay was HUT 102/6TG cells plated without fusion toxin and the positive control was HUT 102/6TG cells plated with cycloheximide (Sigma) (1:8) for 15 minutes at 37° C. with 5% $CO_2$. Both controls were analyzed in triplicate for each assay. The inhibition assays follow the protocol above with a 1-hour incubation of 10 μL of the human IL-2 inhibitor ($10^{-6}$ M as final concentration) with the HUT 102/6TG cells prior to addition of the fusion toxins Inhibition assays were then pulsed, harvested and read as described above.

Cellular proliferation inhibition analysis was performed exactly as the protein synthesis inhibition assays described previously except for the following two differences: 1) HUT 102/6TG cells were cultured, washed, diluted and incubated using RPMI 1640 media supplemented with 12% fetal bovine serum, 10 mM hepes (N-2-hydroxyethylpiperazine-N-2-ethanesulfonic acid), 1x nonessential amino acids, 1 mM sodium pyruvate, 2 mM glutamine, and $2.5 \times 10^{-5}$ M

Example 3.1

Expression and Purification of the Human IL-2 Fusion Toxins in Yeast *Pichia Pastoris*

Based on our experience in developing porcine IL-2 fusion toxins (Peraino et al., J Immunol Methods 398-399: 33-43 (2013)), we hypothesized that the bivalent human IL-2 fusion toxin would prove to be a more potent in vivo depletion agent of human CD25+ cells than the clinically-used monovalent human IL-2 fusion toxin (denileukin diftitox, Ontak®). FIG. 18 presents a schematic representation of the monovalent and bivalent human IL-2 fusion toxins we constructed in this study. The codon-optimized human IL-2 DNA (FIG. 19) was cloned into the C-terminus of the DT390-containing yeast *Pichia Pastoris* expression vector pwPlCZalpha-DT390 between NcoI and EcoRI (Wang et al., 2011). We added a 6× his tag to the C-terminus of each fusion toxin to aid in protein purification. The DT390 domain was genetically linked to the human IL-2 domain by a linker containing four glycine residues and a serine residue ($G_4S$). The two human IL-2 domains which make up the bivalent isoform were joined by three tandom $G_4S$ linkers $(G_4S)_3$.

The human IL-2 fusion toxins were expressed in a yeast *Pichia Pastoris* expression system using one liter Erlenmyer flasks. The human IL-2 fusion toxins were secreted into the extracellular supernatant then captured using a Ni-sepharose fast flow resin and further purified using strong anion exchange resin. The final purification yield was ~5 mg per liter of the original harvested supernatant for both monovalent and bivalent human IL-2 fusion toxins. The purified human IL-2 fusion toxins were analyzed by SDS-PAGE (FIG. 20A) and Western blot using a mouse anti-His monoclonal antibody (FIG. 20B) and a mouse anti-diphtheria toxin monoclonal antibody (FIG. 20C).

Example 3.2

Binding Affinity Analysis of the Human IL-2 Fusion Toxins for Human CD25

Figure 21A:
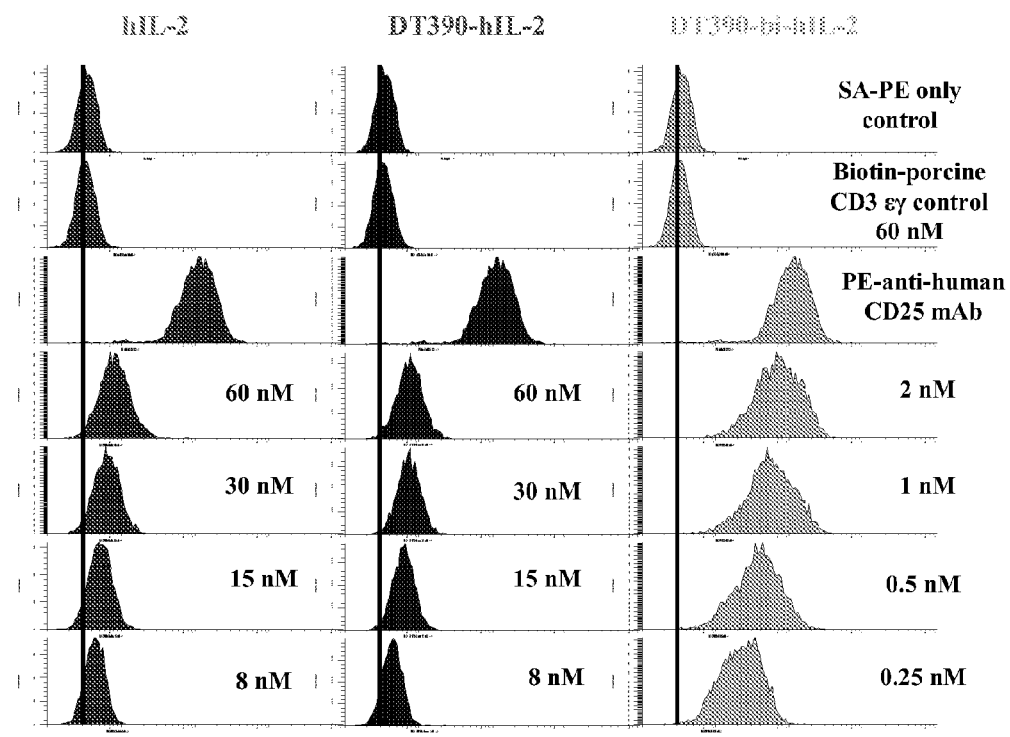
FIGS. 21A-C. Binding of the human IL-2 fusion toxins to human CD25$^+$ HUT 102/6TG cells. A) Histograms of the DT390-hIL-2 (middle panel), DT390-bi-hIL-2 (right panel) as well as positive control human IL-2 (left panel). Cells with only the secondary staining (PE-conjugated streptavidin) served as the negative control and PE-conjugated mouse anti-human CD25 mAb (clone # M-A251, BD Pharmingen, cat #555432) was used for the positive control. Biotin-labeled porcine CD3-εγ (Peraino et al., 2012b) was included as a negative control for background due to protein biotinylation. The data are representative of multiple individual experiments. B-C) Kd determination using flow cytometry and nonlinear least squares fit. MFI was plotted over a range of concentrations of biotinylated B) DT390-hIL-2, C) DT390-bi-hIL-2. The accompanying least-squares fit and parameters are shown based on the hyperbolic equation y=m1+m2*m0/(m3+m0) where y=MFI at the given biotinylated human IL-2 fusion toxin concentration, m0=biotinylated or human IL-2 fusion toxin concentration, m1=MFI of zero biotinylated human IL-2 fusion toxin, m2=MFI at saturation and m3=Kd. The inset table in B) shows a fitted Kd of 15.9 nM for DT390-hIL-2. The inset table in C) shows a fitted Kd of 0.21 nM for DT390-bi-hIL-2.
Figure 21B:
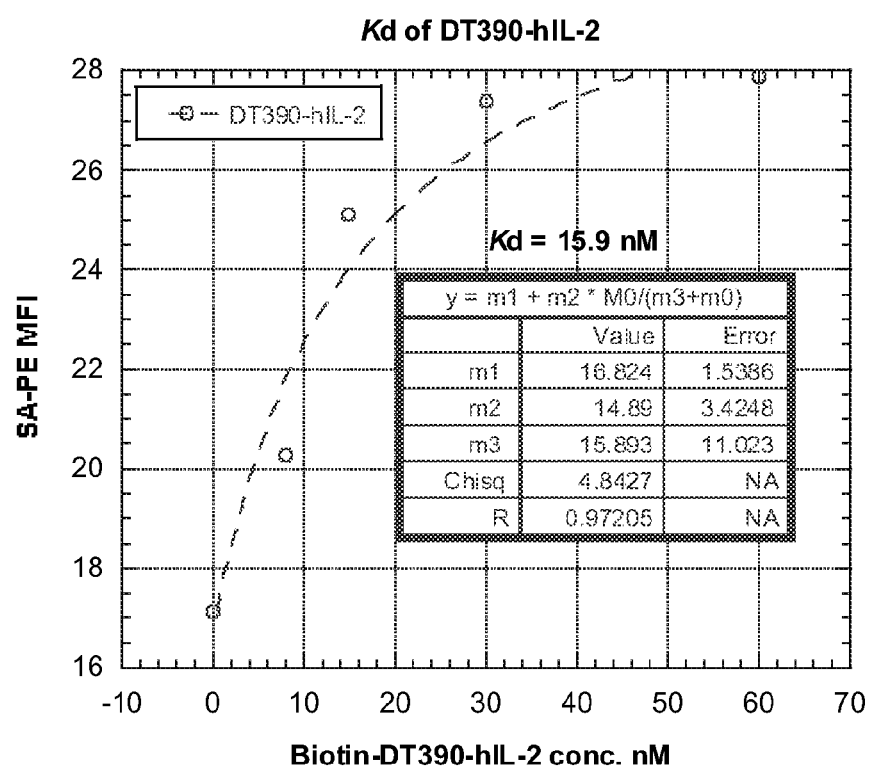
Figure 21C:
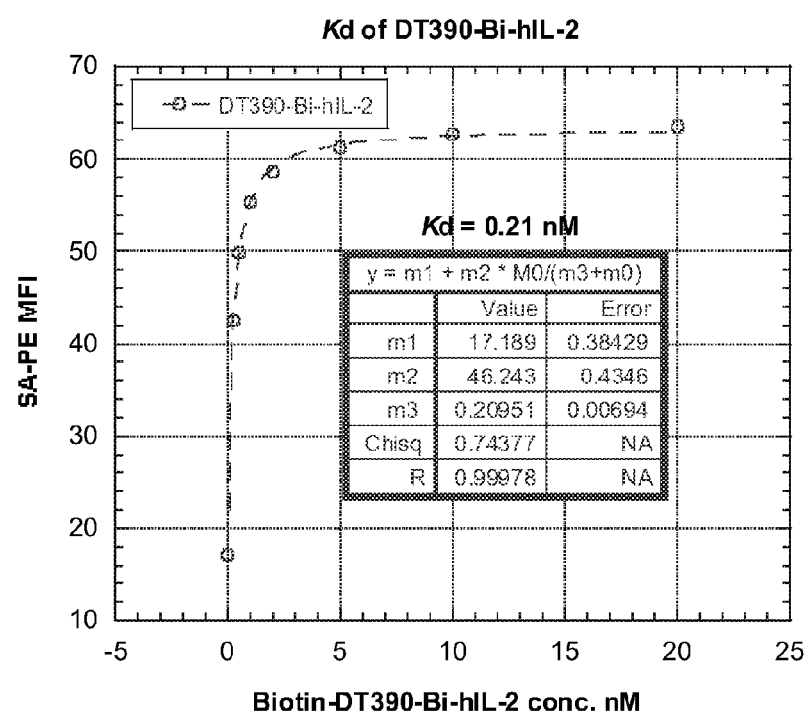

The diphtheria toxin-based human IL-2 fusion toxins target cells expressing the human IL-2 receptor via binding of the human IL-2 domain of the fusion toxins. Following cellular internalization, the DT390 domain functions to inhibit protein synthesis resulting in cell death (Murphy et al., 2011). Therefore, the first critical step in determining the functionality of the human IL-2 fusion toxins was to analyze their binding affinity for human CD25. Both bivalent and monovalent human IL-2 fusion toxins were labeled with sulfo-EZ-link NHS biotin (Thermo Scientific) for binding analysis using flow cytometry (FIG. 21A). Binding affinity was quantified by calculating the dissociation constant (Kd) for each human IL-2 fusion toxins from mean fluorescence intensity (MFI) (Peraino et al., J Immunol Methods 391, 103 (2013)). Consistent with previously developed recombinant fusion toxins/immunotoxins (Woo et al., 2002; Kim et al., Protein Eng. Des. Sel. 20, 425 (2007); Wang et al., 2011), the bivalent human IL-2 fusion toxin was found to have notably higher affinity, approximately two logs stronger, for human CD25 (Kd=0.21 nM) (FIG. 21C) compared to the monovalent isoform (Kd=15.9 nM) (FIG. 21B). Human IL-2 was also included as a control. All of the binding and potency assay results in this study were confirmed using a second human CD25+ lymphoma cell line, SR (ATCC CRL-2262).

Example 3.3

Figure 22:
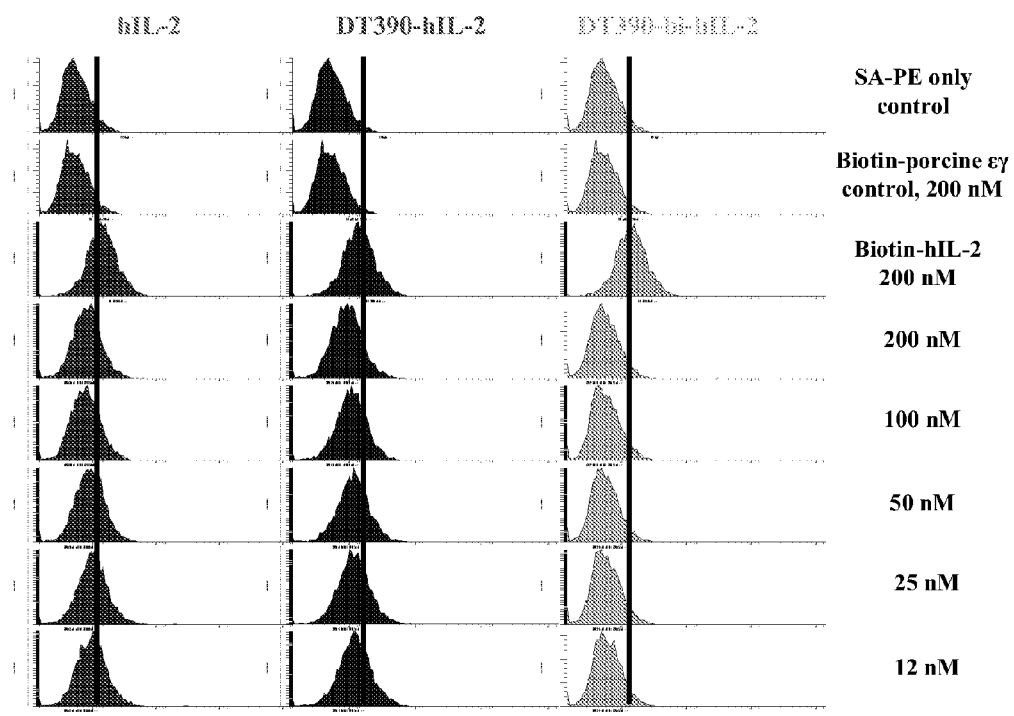
FIG. 22. Binding specificity of the human IL-2 fusion toxins for the human IL-2 receptor on human CD25$^+$ HUT 102/6TG cells. Unlabeled human IL-2 fusion toxins as well as the positive control human IL-2 were each incubated with HUT 102/6TG cells at a range of concentrations for 5 minutes at 4° C. in the dark. Subsequently, without washing the cells, biotin-labeled human IL-2 was added to each tube containing cells in the presence of the unlabeled fusion toxin or human IL-2. Binding specificity of the human IL-2 fusion toxin or human IL-2 to the IL-2 receptor on HUT 102/6TG cells was measured by a decrease in biotin-labeled human IL-2 staining in the presence of increasing concentrations of the unlabeled proteins. Biotin- IL-2 inhibitor; C) bivalent human IL-2 fusion toxin (DT390-bi-hIL-2) with (green) and without (orange) human IL-2 inhibitor. Y-axis: cpm value measuring cellular incorporation of tritiated thymidine. X-axis: plated human IL-2 fusion toxin concentration. Wells containing the human IL-2 inhibitor were incubated for 1 hr at 37° C. before addition of the fusion toxin. Cycloheximide (1:8) was used as a positive control. Cells without fusion toxin served as the negative control. Data are representative of multiple assays.

Binding Specificity of the Human IL-2 Fusion Toxins for the Human IL-2 Receptor In order to prove that the human IL-2 fusion toxins bind specifically to the human IL-2 receptor we analyzed the ability of the fusion toxins to block the binding of human IL-2 to its receptor on HUT 102/6TG cells. Both monovalent and bivalent human IL-2 fusion toxins proved capable of inhibiting the binding of biotinylated human IL-2 to the cells suggesting that the human IL-2 fusion toxins are binding specifically to the human IL-2 receptor (FIG. 22). Moreover, the same trend was observed with strength in inhibition as seen in the above binding analysis in that the bivalent isoform demonstrated stronger hindrance of human IL-2 binding compared to the monovalent human IL-2 fusion toxin. Human IL-2 was also included as positive control.

Example 3.4

In Vitro Potency of the Human IL-2 Fusion Toxins

Figure 23A:
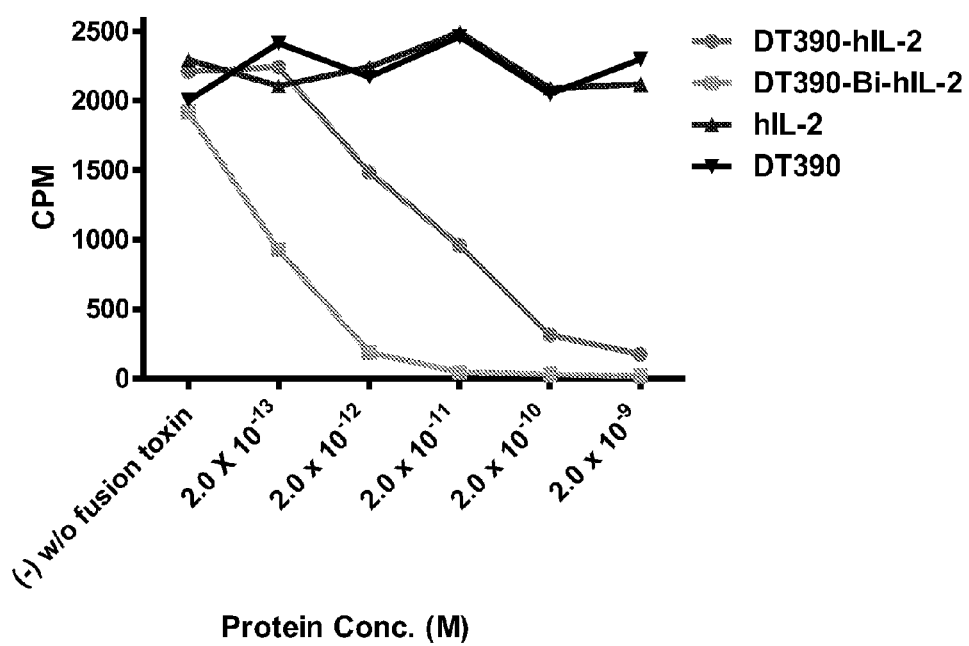

Following successful binding of the human IL-2 domain(s) of the fusion toxins to the cell surface human IL-2 receptor, the fusion toxin is internalized via endocytosis. Once inside the cell, the catalytic domain (A chain) of the DT390 is cleaved and deactivates elongation factor 2 (EF-2) thereby hindering the cell's ability to synthesize new proteins. The potency of protein synthesis inhibition of the human IL-2 fusion toxins was assessed in vitro and quantified by measuring the target cells' incorporation of tritiated leucine into newly synthesized proteins. While both monovalent and bivalent human IL-2 fusion toxins proved capable of impeding protein synthesis in HUT 102/6TG cells, the bivalent isoform displayed an increased potency ($IC_{50}=2\times10^{-13}$ M) of approximately 2 logs when compared with the Ontak®-like monovalent version ($IC_{50}=2\times10^{-11}$M) (FIG. 23A). The degree of protein synthesis inhibition was comparable between clinically used Ontak® and our Ontak®-like monovalent human IL-2 fusion toxin (data not shown). Human IL-2 and DT390 served as controls in this assay.

Figure 23B:
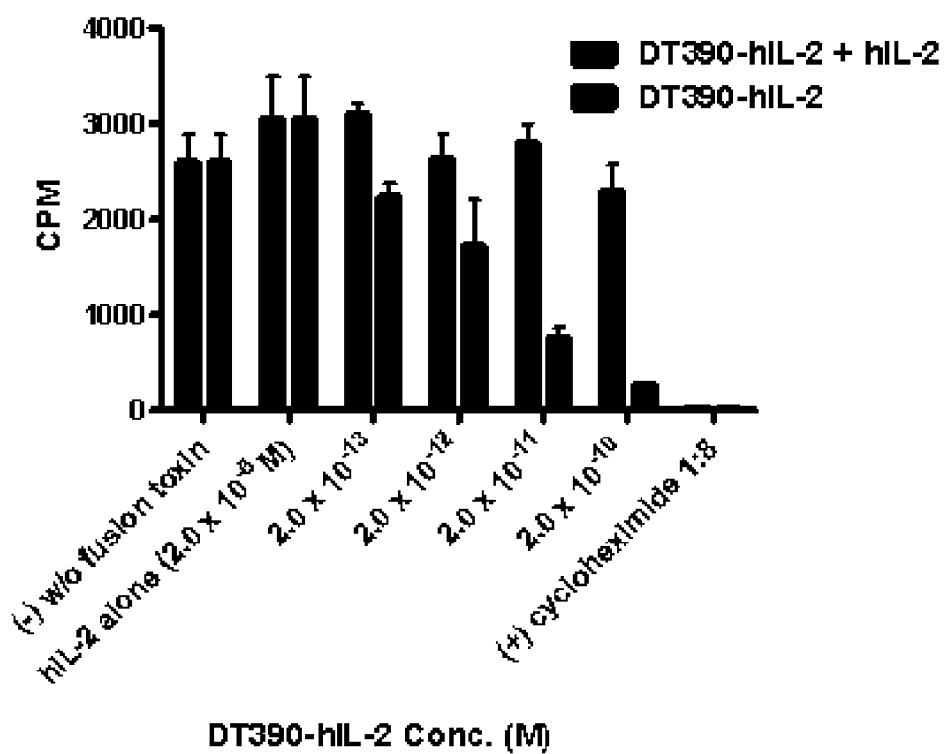
Figure 23C:
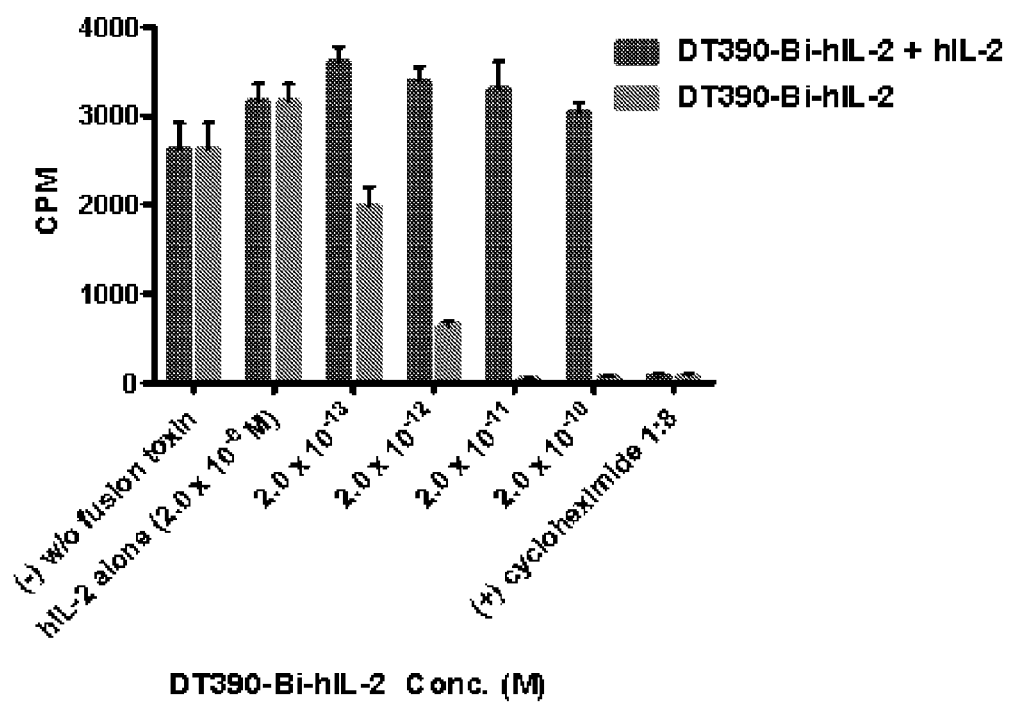

In an effort to demonstrate that the HUT 102/6TG cells are being targeted specifically through the interaction of the human IL-2 domain on the fusion toxin and the IL-2 receptor on the cell surface, we assessed the fusion toxins' ability to halt protein synthesis in the presence of human IL-2. Target cells that were incubated with fusion toxin in the presence of human IL-2 showed a marked increase in protein synthesis compared to cells which were cultured with the corresponding concentration of fusion toxin only. Human IL-2 acted as an inhibitor of fusion toxin as it prevented both the monovalent (FIG. 23B) and bivalent (FIG. 23C) fusion toxins from targeting the human CD25+ cells. Additionally, the bivalent isoform proved to be more potent than the Ontak®-like monovalent fusion toxin in inhibiting protein synthesis.

Figure 24A:
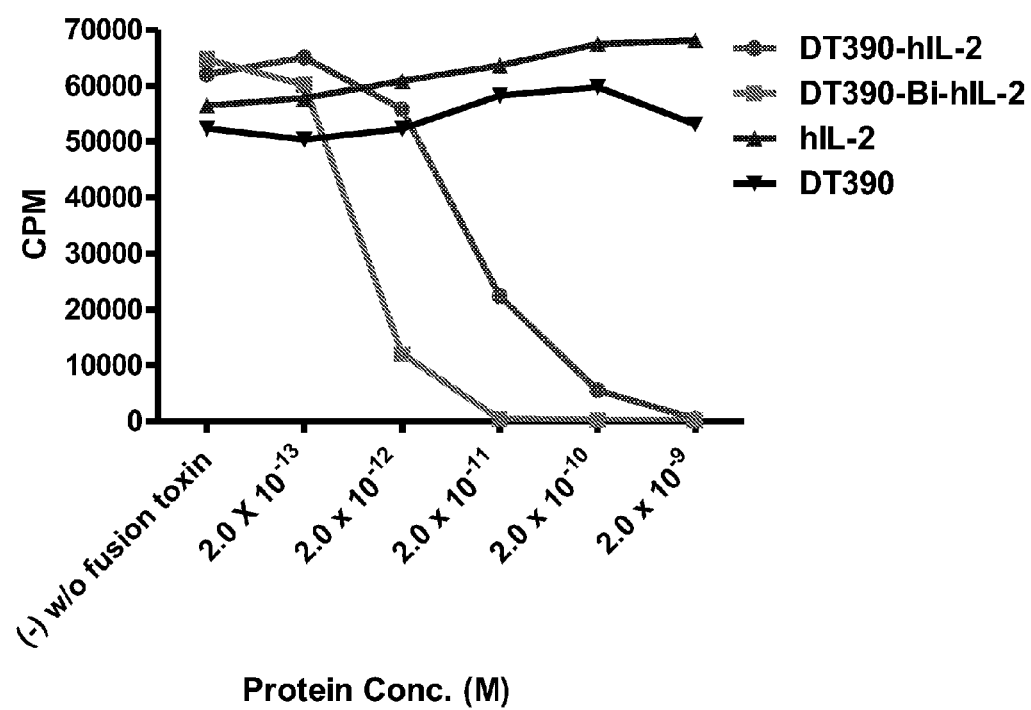

In order to confirm that the hindrance of protein synthesis in the human CD25+ target cells was specifically due to the human IL-2 fusion toxins and not because of the consequence of culturing the cells in leucine-free media, we assessed the functional ability of these fusion toxins to inhibit cellular proliferation in the same target cells using complete culture media. Cellular proliferation was quantified by measuring the incorporation of tritiated thymidine into newly synthesized DNA in target human CD25+ cells following incubation with the human IL-2 fusion toxins. The result was consistent with that of protein synthesis inhibition assays in that both fusion toxins obstructed cellular proliferation in the target cells. The bivalent isoform consistently demonstrated a potency of more than one log greater than the monovalent human IL-2 fusion toxin (FIG. 24A). As for the protein synthesis inhibition assays, human IL-2 and DT390 were included as controls.

Figure 24B:
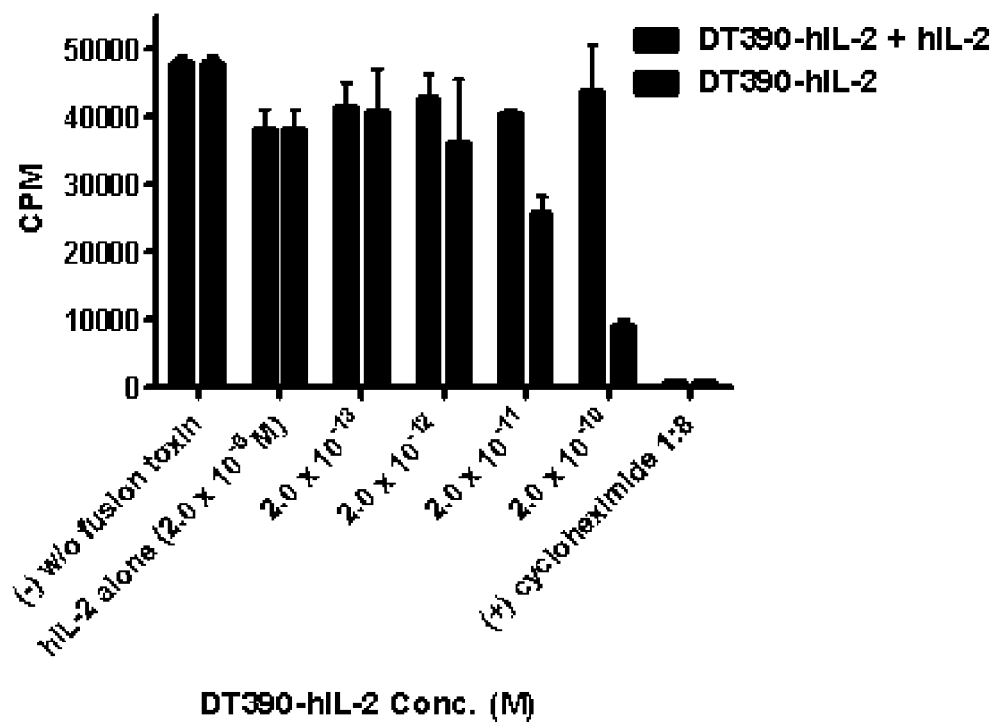
Figure 24C:
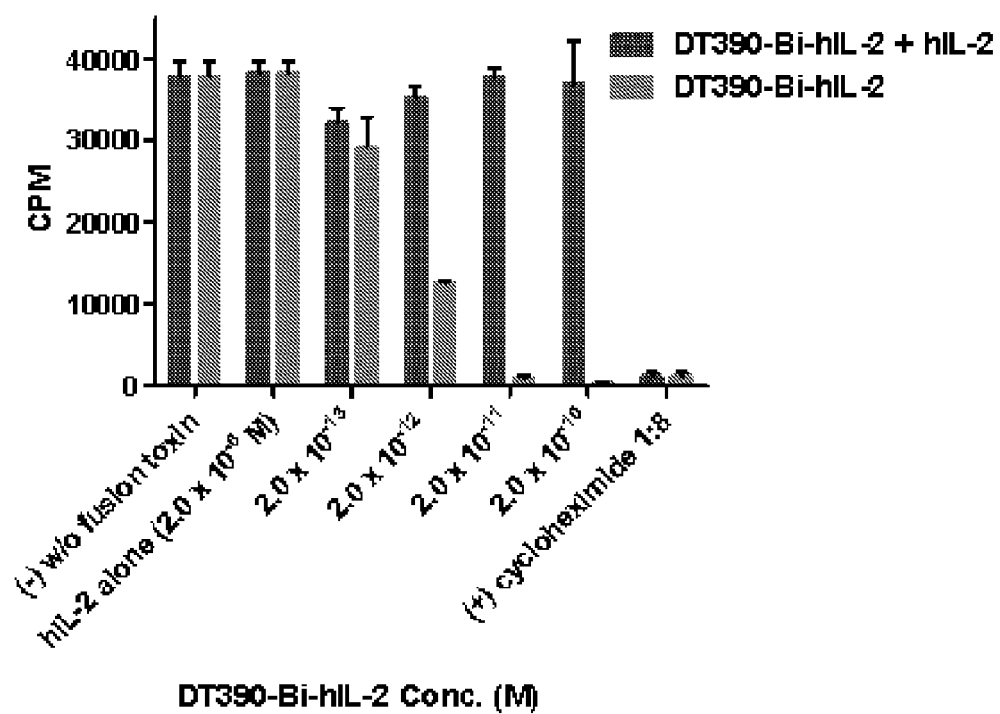

To confirm the fusion toxins bound to the target cells via interaction of the cell surface human IL-2 receptor with the human IL-2 domain of the fusion toxins in this cell proliferation inhibition assay, the ability of the human IL-2 fusion toxins to inhibit cellular proliferation was observed in the presence of an inhibitor, human IL-2. Consistently, human IL-2 drastically affected the ability of both fusion toxins to obstruct cellular proliferation in target cells, and the bivalent isoform (FIG. 24C), again, yielded a higher potency than the monovalent fusion toxin (FIG. 24B).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bivalent IL-2 fusion toxin comprising:
   a first part comprising a cytotoxic protein, and
   a second part comprising at least two Interleukin 2 (IL-2) sequences comprising amino acids 21-153 of SEQ ID NO:1, wherein the cytotoxic protein comprises diphtheria toxin, *Pseudomonas exotoxin*, or cytotoxic portions or variants thereof.

2. The fusion toxin of claim 1, wherein the cytotoxic protein comprises diphtheria toxin, or cytotoxic portions or variants thereof.

3. The fusion toxin of claim 1, further comprising a linker between the first and second parts.

4. The fusion toxin of claim 1, wherein fusion toxin comprises a linker between the two IL-2 sequences.

5. A codon-optimized nucleic acid molecule optimized for expression in a methylotropic yeast encoding the fusion toxin of claim 1.

6. A nucleic acid encoding the fusion toxin of claim 1.

7. A vector comprising the nucleic acid molecule of claim 6.

8. A host cell expressing the nucleic acid molecule of claim 5.

9. The host cell of claim 8, wherein the host cell is a methylotropic yeast.

10. The host cell of claim 8, wherein the host cell is a cell of the species *Pichia Pastoris*.

11. A pharmaceutical composition comprising the fusion toxin of claim 1, and a physiologically acceptable carrier.

12. A method of treating a subject who has a cancer, the method comprising administering to the subject a therapeutically effective amount of the fusion toxin of claim 1.

13. The method of claim 12, wherein the cancer comprises cancer cells that express CD25.

14. The method of claim 12, further comprising administering an immunotherapy to the subject.

15. The method of claim 14, wherein the immunotherapy comprises administration of one or more of: dendritic cells or peptides with adjuvant; DNA-based vaccines; cytokines; cyclophosphamide; anti-interleukin-2R immunotoxins; antibodies; virus-based vaccines ; formulations of Toll-like Receptor or RIG-I-like receptor ligands; or adoptive T cell therapy or other cell therapy.

16. The method of claim 12, wherein the cancer is selected from the group consisting of B-cell neoplasms, acute nonlymphocytic leukemias, neuroblastomas, tumor infiltrating lymphocytes, and cutaneous T cell lymphoma.

17. A method of depleting CD25-expressing regulatory T cells in a subject, the method comprising administering to the subject an effective amount of the fusion toxin of claim 1.

18. The method of claim 17, wherein the subject has cancer, or is an experimental model of autoimmune disease or transplant rejection.

19. A method of producing a bivalent IL-2 fusion toxin, the method comprising:
    expressing a codon-optimized nucleic acid molecule encoding the fusion toxin of claim 1 in a methylotropic yeast; and
    substantially purifying the fusion toxin,
    thereby producing the the fusion toxin.

20. The method of claim 19, wherein the methylotropic yeast is of the species *Pichia Pastoris*.

* * * * *

UNITED STATES PATENT AND TRADEMARK OFFICE
CERTIFICATE OF CORRECTION

PATENT NO. : 9,764,006 B2  
APPLICATION NO. : 14/650699  
DATED : September 19, 2017  
INVENTOR(S) : Zhirui Wang, Christene A. Huang and David H. Sachs It is certified that error appears in the above-identified patent and that said Letters Patent is hereby corrected as shown below:

On the Title Page

Item [75], Line 1, delete "Maiden, MA" and insert -- Malden, MA --,

In the Claims

Column 65, Line 17, Claim 5, delete "methylotropic" and insert -- methylotrophic --, Column 65, Line 25, Claim 9, delete "methylotropic" and insert -- methylotrophic --, Column 66, Line 9, Claim 15, delete "vaccines ;" and insert -- vaccines; --, Column 66, Line 26, Claim 19, delete "methylotropic" and insert -- methylotrophic --, Column 66, Line 29, Claim 19, delete "the the" and insert -- the --, Column 66, Line 30, Claim 20, delete "methylotropic" and insert -- methylotrophic --.

Signed and Sealed this  
Seventeenth Day of April, 2018

Andrei Iancu  
*Director of the United States Patent and Trademark Office*